United States Patent
Linderoth et al.

(10) Patent No.: US 10,689,429 B2
(45) Date of Patent: Jun. 23, 2020

(54) DOUBLE-ACYLATED GLP-1 COMPOUNDS

(71) Applicant: Novo Nordisk A/S, Bagsvaerd (DK)

(72) Inventors: Lars Linderoth, Alleroed (DK); Jacob Kofoed, Vaerloese (DK); Jesper Lau, Farum (DK); Paw Bloch, Jyllinge (DK); Patrick William Garibay, Holte (DK); Janos Tibor Kodra, Koebenhavn OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/301,960

(22) PCT Filed: Apr. 7, 2015

(86) PCT No.: PCT/EP2015/057442
§ 371 (c)(1),
(2) Date: Oct. 5, 2016

(87) PCT Pub. No.: WO2015/155151
PCT Pub. Date: Oct. 15, 2015

(65) Prior Publication Data
US 2017/0114116 A1   Apr. 27, 2017

(30) Foreign Application Priority Data
Apr. 7, 2014   (EP) ..................................... 14163697

(51) Int. Cl.
*C07K 14/605*   (2006.01)
*C07C 235/20*   (2006.01)
*A61K 38/00*   (2006.01)

(52) U.S. Cl.
CPC .......... *C07K 14/605* (2013.01); *C07C 235/20* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,291,594 B2 * | 11/2007 | Hayashi | A61K 38/26 514/11.7 |
| 2003/0078269 A1 * | 4/2003 | Pearson | A61K 31/16 514/251 |
| 2006/0194720 A1 | 8/2006 | Hayashi et al. | |
| 2006/0286129 A1 | 12/2006 | Sarubbi | |
| 2011/0166321 A1 | 7/2011 | Garibay et al. | |
| 2013/0053311 A1 * | 2/2013 | Kalthoff | A61K 38/00 514/7.2 |
| 2014/0004198 A1 | 1/2014 | Balschmidt et al. | |
| 2015/0366946 A1 * | 12/2015 | Vol | A61K 38/28 424/450 |

FOREIGN PATENT DOCUMENTS

| | | |
|---|---|---|
| WO | 9808871 A1 | 3/1998 |
| WO | 99/43706 A1 | 9/1999 |
| WO | 99/43708 A1 | 9/1999 |
| WO | 00/34331 | 6/2000 |
| WO | 01/35988 A1 | 5/2001 |
| WO | 06097537 A2 | 9/2006 |
| WO | 09030771 A1 | 3/2009 |
| WO | 2011/080102 A2 | 7/2011 |
| WO | 2011/080103 A1 | 7/2011 |
| WO | 2012062803 A1 | 5/2012 |
| WO | 2012062804 A1 | 5/2012 |
| WO | 2012140117 A1 | 10/2012 |
| WO | 2013/037690 A1 | 3/2013 |
| WO | 2013/167454 A1 | 11/2013 |
| WO | 2013/167455 A1 | 11/2013 |

OTHER PUBLICATIONS

Knudsen L. B. et al., Potent Derivatives of Glucagon-like Peptide-1 with Pharmacokinetic Properties Suitable for Once Daily Administration, Journal of Medicinal Chemistry, American Chemical Society, US, 2000, vol. 43, No. 9, pp. 1664-1669.

(Continued)

*Primary Examiner* — Lianko G Garyu
(74) *Attorney, Agent, or Firm* — Jianjie Hu

(57) ABSTRACT

The invention relates to a derivative of a GLP-1 peptide, which peptide comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and a maximum of seven amino acid changes as compared to GLP-1 (7-37) (SEQ ID NO: 1); which derivative comprises two protractors attached to said first and second Lys residue, respectively, each via a linker; wherein the protractor is selected from:

HOOC—$C_6H_4$—O—$(CH_2)_y$—CO—*, and   Chem. 1:

HOOC—$(CH_2)_x$—CO—*,   Chem. 2:

wherein y is an integer in the range of 8-11, and x is 12; and the linker comprises at least one of:

*—NH—CH(COOH)—$(CH_2)_2$—CO—*,   Chem. 3:

*—NH—CH($(CH_2)_2$—COOH)—CO—*, and/or   Chem. 4:

*—NH—$(CH_2)_2$—[O—$(CH_2)_2]_k$—O—$[CH_2]_n$—CO—*,   Chem. 5:

wherein k is an integer in the range of 1-5, and n is an integer in the range of 1-5; or a pharmaceutically acceptable salt, amide, or ester thereof. The invention also relates to the pharmaceutical uses thereof, such as for the treatment of diabetes and obesity, as well as to the GLP-1 peptides forming part of these derivatives which have Lys residues at positions 36 and 37 and no other Lys residues, and the GLP-1(9-37) fragments thereof. The invention furthermore relates to an intermediate product comprising 3-carboxyphenoxy-nonanoic acid with a protection group at the carboxy group of the nonanoic acid, optionally via a linker. The derivatives have a very good potency and a long half-life which makes them potentially useful for, e.g., oral administration.

11 Claims, No Drawings

Specification includes a Sequence Listing.

(56) References Cited

OTHER PUBLICATIONS

Tang W. et al., Discovery of histone deacetylase 8 selective inhibitors, Bioorganic and Medicinal Chemistry Letters, 2011, vol. 21, No. 9, pp. 2601-2605.

* cited by examiner

SEQUENCE LISTING

<160> NUMBER OF SEQ ID NOS: 8

<210> SEQ ID NO 1
<211> LENGTH: 31
<212> TYPE: PRT
<213> ORGANISM: Homo sapiens
<220> FEATURE:

```
<221> NAME/KEY: mat_peptide
<222> LOCATION: (1)..(31)
<223> OTHER INFORMATION: Native human GLP-1(7-37)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: mat_peptide
<222> LOCATION: (1)..(31)
<223> OTHER INFORMATION: GLP-1 analogue
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 2

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Lys
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: mat_peptide
<222> LOCATION: (1)..(31)
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 3

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Lys
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: mat_peptide
<222> LOCATION: (1)..(31)
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 4
```

```
His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Gln Gly Lys Lys
            20                  25                  30
```

<210> SEQ ID NO 5
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: mat_peptide
<222> LOCATION: (1)..(31)

<400> SEQUENCE: 5

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Lys
            20                  25                  30
```

<210> SEQ ID NO 6
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: mat_peptide
<222> LOCATION: (1)..(31)
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 6

```
His Xaa Glu Gly Thr Phe Thr Ser Asp Val Ser Ser Tyr Leu Glu Glu
1               5                   10                  15

Gln Ala Ala Arg Glu Phe Ile Glu Trp Leu Val Arg Gly Lys Lys
            20                  25                  30
```

<210> SEQ ID NO 7
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: L-histidine, (S)-2-Hydroxy-3-(1H-imidazol-4-
      yl)-propionic acid, D-histidine, desamino-histidine (desH), N?-
      acetyl-histidine, N?-formyl-histidine
<220> FEATURE:
<221> NAME/KEY: MISC_FEATURE
<222> LOCATION: (2)..(2)
<223> OTHER INFORMATION: Ala, Gly, Ser, Aib, (1-aminocyclopropyl)
      carboxylic acid, (1-aminocyclobutyl) carboxylic acid
<220> FEATURE:
<221> NAME/KEY: MISC_FEATURE
<222> LOCATION: (10)..(10)
<223> OTHER INFORMATION: Val or Leu
<220> FEATURE:
<221> NAME/KEY: MISC_FEATURE
<222> LOCATION: (12)..(12)
<223> OTHER INFORMATION: Ser or Arg
<220> FEATURE:
<221> NAME/KEY: MISC_FEATURE
<222> LOCATION: (13)..(13)
<223> OTHER INFORMATION: Tyr or Gln -continued

```
<220> FEATURE:
<221> NAME/KEY: MISC_FEATURE
<222> LOCATION: (14)..(14)
<223> OTHER INFORMATION: Leu or Met
<220> FEATURE:
<221> NAME/KEY: MISC_FEATURE
<222> LOCATION: (16)..(16)
<223> OTHER INFORMATION: Gly or Glu
<220> FEATURE:
<221> NAME/KEY: MISC_FEATURE
<222> LOCATION: (17)..(17)
<223> OTHER INFORMATION: Gln, Glu, or Arg
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Arg or Lys
<220> FEATURE:
<221> NAME/KEY: MISC_FEATURE
<222> LOCATION: (21)..(21)
<223> OTHER INFORMATION: Glu or Leu
<220> FEATURE:
<221> NAME/KEY: MISC_FEATURE
<222> LOCATION: (24)..(24)
<223> OTHER INFORMATION: Ala or Glu
<220> FEATURE:
<221> NAME/KEY: MISC_FEATURE
<222> LOCATION: (25)..(25)
<223> OTHER INFORMATION: Trp or His
<220> FEATURE:
<221> NAME/KEY: MISC_FEATURE
<222> LOCATION: (27)..(27)
<223> OTHER INFORMATION: Val or Arg
<220> FEATURE:
<221> NAME/KEY: MISC_FEATURE
<222> LOCATION: (28)..(28)
<223> OTHER INFORMATION: Arg, Lys, His, Asn, or Gln
<220> FEATURE:
<221> NAME/KEY: MISC_FEATURE
<222> LOCATION: (29)..(29)
<223> OTHER INFORMATION: Gly or Aib

<400> SEQUENCE: 7

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Lys Lys
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: L-histidine, (S)-2-Hydroxy-3-(1H-imidazol-4-
      yl)-propionic acid, D-histidine, desamino-histidine (desH), N?-
      acetyl-histidine, N?-formyl-histidine
<220> FEATURE:
<221> NAME/KEY: MISC_FEATURE
<222> LOCATION: (2)..(2)
<223> OTHER INFORMATION: Ala, Ser, Aib, (1-aminocyclopropyl) carboxylic
      acid, (1-aminocyclobutyl) carboxylic acid
<220> FEATURE:
<221> NAME/KEY: MISC_FEATURE
<222> LOCATION: (10)..(10)
<223> OTHER INFORMATION: Val or Leu
<220> FEATURE:
<221> NAME/KEY: MISC_FEATURE
<222> LOCATION: (12)..(12)
<223> OTHER INFORMATION: Ser or Arg
```

```
<220> FEATURE:
<221> NAME/KEY: MISC_FEATURE
<222> LOCATION: (13)..(13)
<223> OTHER INFORMATION: Tyr or Gln
<220> FEATURE:
<221> NAME/KEY: MISC_FEATURE
<222> LOCATION: (14)..(14)
<223> OTHER INFORMATION: Leu or Met
<220> FEATURE:
<221> NAME/KEY: MISC_FEATURE
<222> LOCATION: (16)..(16)
<223> OTHER INFORMATION: Gly or Glu
<220> FEATURE:
<221> NAME/KEY: MISC_FEATURE
<222> LOCATION: (17)..(17)
<223> OTHER INFORMATION: Gln, Glu, or Arg
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Arg or Lys
<220> FEATURE:
<221> NAME/KEY: MISC_FEATURE
<222> LOCATION: (21)..(21)
<223> OTHER INFORMATION: Glu or Leu
<220> FEATURE:
<221> NAME/KEY: MISC_FEATURE
<222> LOCATION: (24)..(24)
<223> OTHER INFORMATION: Ala or Glu
<220> FEATURE:
<221> NAME/KEY: MISC_FEATURE
<222> LOCATION: (25)..(25)
<223> OTHER INFORMATION: Trp or His
<220> FEATURE:
<221> NAME/KEY: MISC_FEATURE
<222> LOCATION: (27)..(27)
<223> OTHER INFORMATION: Val or Arg
<220> FEATURE:
<221> NAME/KEY: MISC_FEATURE
<222> LOCATION: (28)..(28)
<223> OTHER INFORMATION: Arg, Lys, His, Asn, or Gln
<220> FEATURE:
<221> NAME/KEY: MISC_FEATURE
<222> LOCATION: (29)..(29)
<223> OTHER INFORMATION: Gly or Aib

<400> SEQUENCE: 8

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Lys Lys
            20                  25                  30
```

DOUBLE-ACYLATED GLP-1 COMPOUNDS

CROSS-REFERENCE TO RELATED APPLICATIONS

This application is a 35 U.S.C. § 371 National Stage application of International Application PCT/EP2015/057442 (WO 2015/155151), filed Apr. 7, 2015, which claimed priority of European Patent Application 14163697.7, filed Apr. 7, 2014; the contents of which are incorporated herein by reference.

TECHNICAL FIELD

The present invention relates to derivatives of analogues of Glucagon-Like Peptide 1 (GLP-1), more in particular to double-acylated GLP-1 derivatives acylated at 36Lys and at 37Lys, and their pharmaceutical use. The invention also relates to GLP-1 analogues having 36Lys and 37Lys and no other Lys residues, as well as to an intermediate product comprising 3-carboxyphenoxy-nonanoic acid with a protection group at the carboxy group of the nonanoic acid, optionally via a linker.

INCORPORATION-BY-REFERENCE OF THE SEQUENCE LISTING

In accordance with 37 C.F.R. § 1.52(e)(5), Applicants enclose herewith the Sequence Listing for the above-captioned application entitled "130049US01_SeqList_ST25", created on Sep. 29, 2016. The Sequence Listing is made up of 3,356 bytes, and the information contained in the attached "130049US01_SeqList_ST25" is identical to the information in the specification as originally filed. No new matter is added.

BACKGROUND

WO 2011/080103, WO 2012/062803, WO 2012/062804, WO 2012/140117, WO 2013/037690, WO 2013/167455, and WO 2013/167454 disclose various double-acylated GLP-1 derivatives, and U.S. Pat. No. 7,291,594 B2 discloses various GLP-1 peptide analogues including some that have Lys residues at positions 36 and 37.

SUMMARY

The present invention relates to double-acylated GLP-1 derivatives.

Liraglutide is a mono-acylated GLP-1 derivative for once daily administration which is marketed by Novo Nordisk A/S under the trade name of VICTOZA®. This compound is disclosed in WO 98/08871 A1 (Example 37).

WO 06/097537 A2 discloses among other GLP-1 derivatives semaglutide (Example 4), which is a mono-acylated GLP-1 derivative for once weekly administration which is under clinical development by Novo Nordisk A/S.

The GLP-1 derivatives of the invention are double-acylated. More in particular the GLP-1 derivatives of the invention are GLP-1 peptides having two side chains covalently attached at two neighbouring positions, namely at positions corresponding to positions 36 and 37 of GLP-1(7-37) (SEQ ID NO: 1). Each side chain comprises a linker and a protractor. The protractor may be a radical of a fatty di-acid, or a radical of a fatty acid with a distal carboxy phenoxy group. The linker is a di-radical incorporating an *—NH group and a *—CO group. The *—NH group is at the left hand end of the molecule, and the *—CO group at the right hand end of the molecule, by reference to the line and structural formulas herein. Preferred linkers include one or more Glu residues, and/or one or more Ado residues (Ado is 8-amino-3,6-dioxaoctanoic acid). The protractor and the linker are interconnected via an amide bond. The linker is connected to the epsilon-amino group of 36Lys or 37Lys of the peptide, via an amide bond.

The GLP-1 peptide incorporated in the derivative of the invention is an analogue of GLP-1(7-37) (SEQ ID NO: 1), which analogue comprises a first Lys residue at a position corresponding to position 36 of GLP-1(7-37) (SEQ ID NO: 1) ("36Lys"), and a second Lys residue at a position corresponding to position 37 of GLP-1(7-37) (SEQ ID NO: 1) ("37Lys"). The GLP-1 peptide of the derivative of the invention may have up to seven amino acid changes in total as compared to GLP-1(7-37) (SEQ ID NO: 1), of which 36Lys and 37Lys count for two amino acid changes. The maximum five additional changes may be, independently, one or more extensions, one or more insertions, one or more deletions, and/or one or more substitutions.

More in particular the invention relates, in a first aspect, to a derivative of a GLP-1 peptide, which peptide comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and a maximum of seven amino acid changes as compared to GLP-1(7-37) (SEQ ID NO: 1); which derivative comprises two protractors attached to said first and second Lys residue, respectively, each via a linker; wherein the protractor is selected from:

| | |
|---|---|
| $HOOC-C_6H_4-O-(CH_2)_y-CO-*$, and | Chem. 1: |
| $HOOC-(CH_2)_x-CO-*$, | Chem. 2: | wherein y is an integer in the range of 8-11, and x is 12; and the linker comprises at least one of:

| | |
|---|---|
| $*-NH-CH(COOH)-(CH_2)_2-CO-*$, | Chem. 3: |
| $*-NH-CH((CH_2)_2-COOH)-CO-*$, and/or | Chem. 4: |
| $*-NH-(CH_2)_2-[O-(CH_2)_2]_k-O-[CH_2]_n-CO-*$, | Chem. 5: | wherein k is an integer in the range of 1-5, and n is an integer in the range of 1-5; or a pharmaceutically acceptable salt, amide, or ester thereof.

Preferred GLP-1 derivatives of the invention designated Chem. 21 to Chem. 48 are disclosed in the experimental section.

In a second aspect, the invention relates to a GLP-1 analogue comprising a first Lys residue at a position corresponding to position 36 of GLP-1(7-37) (SEQ ID NO: 1), a second Lys residue at a position corresponding to position 37 of GLP-1(7-37) (SEQ ID NO: 1), wherein the analogue either (i) incorporates no other Lys residues, and/or (ii) incorporates one or more of the amino acid changes (8Aib or 8Gly), 22Glu, 26Arg, 30Glu, and/or (34Arg or 34Gln). The invention also relates to the corresponding GLP-1(9-37) analogues, as well as the pharmaceutically acceptable salts, amides, or esters of these GLP-1 (7-37) and GLP-1(9-37) analogues.

More in particular the invention relates to a GLP-1 peptide of Formula I:

Xaa$_7$-Xaa$_8$-Glu-Gly-Thr-Phe-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Lys$_{36}$-Lys$_{37}$, wherein Xaa$_7$ is L-histidine, (S)-2-Hydroxy-3-(1H- imidazol-4-yl)-propionic acid, D-histidine, desamino-histidine (desH), N^α-acetyl-histidine, N^α-formyl-histidine; $Xaa_8$ is Ala, Gly, Ser, Aib, (1-aminocyclopropyl) carboxylic acid, (1-aminocyclobutyl) carboxylic acid; $Xaa_{16}$ is Val or Leu; $Xaa_{18}$ is Ser or Arg; $Xaa_{19}$ is Tyr or Gln; $Xaa_{20}$ is Leu or Met; $Xaa_{22}$ is Gly or Glu; $Xaa_{23}$ is Gln, Glu, or Arg; $Xaa_{25}$ is Ala or Val; $Xaa_{26}$ is Arg or Lys; $Xaa_{27}$ is Glu or Leu; $Xaa_{30}$ is Ala, or Glu; $Xaa_{31}$ is Trp or His; $Xaa_{33}$ is Val or Arg; $Xaa_{34}$ is Arg, Lys, His, Asn, or Gln; and $Xaa_{35}$ is Gly or Aib.

The invention also relates to a peptide as defined above, except that $Xaa_7$ and $Xaa_8$ are absent.

In a third aspect the invention relates to an intermediate product comprising 3-carboxyphenoxy-nonanoic acid with a protection group at the carboxy group of the nonanoic acid, optionally via a linker.

More in particular the invention relates to an intermediate product comprising a side chain moiety of Chem. 6:

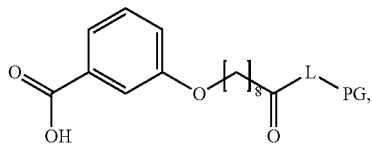

wherein L is an optional linker being a di-radical incorporating an *—NH group and a *—CO group, PG is a protection group, and the distal COOH group and/or any other COOH— group if present, is optionally also protected; or a pharmaceutically acceptable salt, amide or ester thereof.

In a fourth aspect the invention relates to the pharmaceutical use of the GLP-1 derivatives and analogues of the invention, for example for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

The derivatives of the invention are biologically active. For example they are very potent, and, also or alternatively, they bind very well to the GLP-1 receptor.

Also, or alternatively, they have a protracted pharmacokinetic profile. For example they have a very long terminal half-life when administered i.v. to mini pigs and/or dogs.

The particular combination of good potency/binding and long half-life is highly desirable.

Also, or alternatively, they have a high oral bioavailability. For example, when administered orally they may preferably exhibit a sufficiently high plasma-concentration for a desired period of time. Also, or alternatively, the plasma concentration may exhibit a desirable low variation (is relatively constant) in between successive administrations.

Also, or alternatively, they lead to a reduced food intake, which may be indicative of an effect on obesity and other eating disorders.

Also, or alternatively, the number of amino acid changes in the GLP-1 peptide is low.

These properties may be of importance in the development of next generation GLP-1 compounds for subcutaneous, intravenous, and/or in particular oral administration.

Also, or alternatively, it is surprising that GLP-1 analogues with two long side-chains attached to neighbouring amino acid residues in the peptide backbone are functional at all, and even more that they have an improved performance.

DESCRIPTION

In what follows, Greek letters may be represented by their symbol or the corresponding written name, for example: α=alpha; β=beta; ε=epsilon; γ=gamma; ω=omega; etc. Also, the Greek letter of μ may be represented by "u", e.g. in μl=ul, or in μM=uM.

An asterisk (*) in a chemical formula designates i) a point of attachment, ii) a radical, and/or iii) an unshared electron.

In a first aspect, the invention relates to A derivative of a GLP-1 peptide, which peptide comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and a maximum of seven amino acid changes as compared to GLP-1(7-37) (SEQ ID NO: 1); which derivative comprises two protractors attached to said first and second Lys residue, respectively, each via a linker; wherein the protractor is selected from:

HOOC—$C_6H_4$—O—$(CH_2)_y$—CO—*, and      Chem. 1:

HOOC—$(CH_2)_x$—CO—*,      Chem. 2:

wherein y is an integer in the range of 8-11, and x is 12; and the linker comprises at least one of:

*—NH—CH(COOH)—$(CH_2)_2$—CO—*,      Chem. 3:

*—NH—CH($(CH_2)_2$—COOH)—CO—*, and/or      Chem. 4:

*—NH—$(CH_2)_2$—[O—$(CH_2)_2$]$_k$—O—$[CH_2]_n$—CO—*,      Chem. 5:

wherein k is an integer in the range of 1-5, and n is an integer in the range of 1-5; or a pharmaceutically acceptable salt, amide, or ester thereof.

GLP-1 Peptides and Analogues

The GLP-1 peptide of the derivative of the invention may now and then be referred to as the "backbone" or the "peptide backbone" of the derivative.

The term "GLP-1 peptide" as used herein refers to an analogue or variant of the human Glucagon-Like Peptide-1 (GLP-1(7-37)), the sequence of which is included in the sequence listing as SEQ ID NO: 1. The peptide having the sequence of SEQ ID NO: 1 may also be designated "native" GLP-1.

In the sequence listing, the first amino acid residue of native GLP-1 of SEQ ID NO: 1 (histidine) is assigned no. 1. However, in what follows—according to established practice in the art—this histidine residue is referred to as no. 7, and subsequent amino acid residues are numbered accordingly, ending in native GLP-1 with glycine no. 37. Therefore, generally, any reference herein to an amino acid residue number or a position number in native GLP-1 is to the sequence starting with His at position 7 and ending with Gly at position 37.

This practice is followed herein also for the GLP-1 peptides of the invention, which may be described by reference to i) the number of the amino acid residue in native GLP-1(7-37) which corresponds to the amino acid residue which is changed (i.e., the corresponding position in native GLP-1), and to ii) the actual change.

For example, the GLP-1 peptide of the invention is defined so as to comprise a first Lys residue at a position corresponding to position 36 of GLP-1(7-37) (SEQ ID NO: 1), and a second Lys residue at a position corresponding to position 37 of GLP-1(7-37) (SEQ ID NO: 1). These two Lys residues of the GLP-1 peptide of the invention may be designated 36Lys and 37Lys, respectively. For example, a GLP-1 peptide of the invention which only has these two changes as compared to native GLP-1 may be referred to as 36Lys, 37Lys GLP-1(7-37) and/or as GLP-1(7-37) R36K, G37K. Also in these designations the position numbers 36 and 37, respectively, refer to the positions corresponding to position 36 and 37, respectively, in native GLP-1. In the latter expression the residue that is substituted with Lys (K) is also indicated (R and G, respectively, for positions 36 and 37).

The GLP-1 peptide of the invention may have additional amino acid changes as compared to GLP-1(7-37) (SEQ ID NO: 1), however limited to a maximum of seven amino acid changes. These changes are also as compared to native GLP-1(7-37) (SEQ ID NO: 1), and they may represent, independently, one or more amino acid substitutions, insertions, extensions, and/or deletions.

In a particular embodiment the amino acid changes are at one or more positions corresponding to one or more of positions 8, 22, 26, 30, 34, 36, and 37 of GLP-1(7-37) (SEQ ID NO: 1).

In another particular embodiment the GLP-1 peptide of the invention comprises 36Lys and 37Lys, and optionally one or more of the following further amino acid changes: (8Aib or 8Gly), 22Glu, 26Arg, 30Glu, and/or (34Arg or 34Gln). In this embodiment the reference to GLP-1(7-37) of SEQ ID NO: 1 is implied, and the position numbers refer, as explained above, to the positions which correspond to positions 36, 37, 8, 22, 26, 30, and 34, respectively, in native GLP-1. The expression (34Arg or 34Gln) means that the residue at the position corresponding to position 34 in native GLP-1 is either Arg or Gln.

Particular GLP-1 peptides of the invention, which are also incorporated in the particular derivatives of the invention disclosed in the experimental section, are SEQ ID NO: 2, SEQ ID NO: 3, SEQ ID NO: 4, SEQ ID NO: 5, and SEQ ID NO: 6 of the sequence listing.

A peptide "comprising" certain specified changes may comprise further changes, when compared to SEQ ID NO: 1.

As is apparent from the above examples, amino acid residues may be identified by their full name, their one-letter code, and/or their three-letter code. These three ways are fully equivalent.

The total number of amino acid changes, as well as the specific changes (at which position(s) and into what) as compared to native GLP-1 may be identified as is known in the art, e.g. by handwriting and eyeballing, and/or by a suitable program, preferably a Needleman-Wunsch alignment, such as "align". The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix such as BLOSUM62 and the default identity matrix may be used, and the penalty for the first residue in a gap may be set at −10, and the penalties for additional residues in a gap at −0.5.

An example of such alignment of SEQ ID NO: 1 and SEQ ID NO: 2 is inserted hereinbelow:

```
# Aligned sequences: 2

1: SEQ_ID_NO_1

2: SEQ_ID_NO_2

Matrix: EBLOSUM62

Gap_penalty: 10.0

Extend_penalty: 0.5

Length: 31

Identity:   25/31 (80.6%)

Similarity: 28/31 (90.3%)

Gaps:       0/31 (0.0%)

Score: 132.0

SEQ_ID_NO_1   1 HAEGTFTSDVSSYLEGQAAKEFIAWLVKGRG 31
                |.||||||||||||.|||:||||||:|:.
SEQ_ID_NO_2   1 HXEGTFTSDVSSYLEEQAAREFIAWLVRGKK 31
```

As can be inferred from the above alignment, in case of non-coded amino acids such as Aib being included in the sequence, these may, for alignment purposes, be replaced with X. If desired, X can later be manually corrected.

As can also be inferred from the above alignment, SEQ ID NO: 2 is the following analogue of native GLP-1 (SEQ ID NO: 1): 8Aib, 22Glu, 26Arg, 34Arg, 36Lys, 37Lys (where reference to GLP-1(7-37) is implied). In other words, this analogue has 6 amino acid changes as compared to native GLP-1, namely at positions corresponding to positions 8, 22, 26, 34, 36, and 37 of native GLP-1, and the amino acid changes are all substitutions, namely into Aib, Glu, Arg, Arg, Lys, and Lys, respectively.

The term "peptide" refers to a compound which comprises a series of amino acids interconnected by amide (or peptide) bonds.

The peptides of the invention comprise at least five constituent amino acids connected by peptide bonds. In particular embodiments the peptide comprises at least 10, preferably at least 15, more preferably at least 20, even more preferably at least 25, or most preferably at least 28 amino acids.

In particular embodiments, the peptide is composed of at least five constituent amino acids, preferably composed of at least 10, at least 15, at least 20, at least 25, or most preferably composed of at least 28 amino acids.

In additional particular embodiments, the peptide is a) composed of, or b) consists of, i) 28, ii) 29, iii) 30, iv) 31, v) 32, or vi) 33 amino acids.

In a still further particular embodiment the peptide consists of amino acids interconnected by peptide bonds.

An amino acid may be defined as a compound which comprises an amine group and a carboxylic acid group, and optionally one or more additional groups often referred to as a side chain. The amine group may, e.g., be a primary or secondary amino group.

An amino acid residue is a radical of an amino acid as incorporated into a peptide or protein.

In a particular embodiment the amino acids of the peptide of the invention are α-amino acids where the nitrogen atom of the primary or secondary amino group is bonded to the α-carbon atom.

In another particular embodiment the amino acids of the peptide of the invention are selected from coded amino acids and non-coded amino acids.

In still further particular embodiments at least 60%, preferably at least 70%, more preferably at least 80%, even more preferably at least 90%, still more preferably at least 95%, or most preferably at least 97% of the amino acids of the peptide of the invention are coded amino acids.

Coded amino acids may be defined as in Table 1 in section 3AA-1 of the Recommendations by IUPAC (INTERNATIONAL UNION OF PURE AND APPLIED CHEMISTRY; see http://www.chem.qmul.ac.uk/iupac/), where structure, trivial name, systematic name, one- and three-letter symbols for 20 coded amino acids is given.

The term "non-coded amino acids" refers to all other amino acids. Non-limiting examples of non-coded amino acids that may be incorporated in the peptide of the invention are: Aad (2-Aminoadipic acid (2-aminohexanedioic acid)), Abu (2-Aminobutanoic acid), Aca (2-Aminocapric acid (2-aminodecanoic acid)), Aib (α-Aminoisobutyric acid (α-methylalanine)), Apm (2-Aminopimelic acid (2-aminoheptanedioic acid)), Bal (β-Alanine), Bly (3,6-Diaminohexanoic acid (β-lysine)), Bux (4-Amino-3-hydroxybutanoic acid), Cha (3-Cyclohexylalanin), Cit (N5-Aminocarbonylornithine or citrulline), Cya (Cysteic acid, 3-Sulfoalanine), Dab (2,4-Diaminobutanoic acid), Dpm (Diaminopimelic acid), Dpr (2,3-Diaminopropanoic acid), Gla (γ-Carboxyglutamic acid), pGlu (Pyroglutamic acid), hArg (Homoarginine), hCys (Homocysteine), hHis (Homohistidine), hSer (Homoserine), Hyl (5-Hydroxylysine), Hyp (4-Hydroxyproline), Iva (Isovaline), Nal such as 1-Nal or 2-Nal (1-Naphthylalanine, and 2-Naphthylalanine, respectively), Nle (Norleucine), Nva (Norvaline), Orn (Ornithine, 2,5-Diaminohexanoic acid), Pen (Penicillamine (3-mercaptovaline)), Phg (2-Phenylglycine), pSer (Phosphoserine), pThr (Phosphothreonine), pTyr (Phosphotyrosine), Sar (Sarcosine (N-methylglycine)), Tle (3-Methylvaline), Tml (ε-N-Trimethyllysine), and Tza (3-Thiazolylalanine).

Additional non-limiting examples of non-coded amino acids are the D-isomers of the coded amino acids such as D-alanine and D-leucine. A preferred non-coded amino acid is Aib.

In an additional particular embodiment the N-terminal residue of the peptide of the invention may strictly speaking not be an amino acid. For example, it may be modified, intentionally or spontaneously, so that it is no longer an amino acid. Non-limiting examples of such modifications are substitutions of the N-terminal histidine with imidazopropionyl (deamino histidine), or with 2-hydroxy-deaminohistidine. Another example is the transformation of an N-terminal glutamic acid or glutamine into pyroglutamic acid (5-oxo-proline, pidolic acid) which may occur spontaneously.

In what follows, all specific amino acids for which the optical isomer is not stated is to be understood to mean the L-isomer (unless otherwise specified), e.g. when reference is made to the specific amino acid of glutamine, this is intended to refer to L-glutamine, unless otherwise is stated. On the other hand, where amino acids are described by more general formulas such as brutto formulas or structural formulas and when no stereo chemistry is shown, these formulas are intended to cover all stereo isomers.

According to general practice in the art the N-terminus of the GLP-1 peptides of the invention is shown to the left and the C-terminus to the right.

GLP-1 Derivatives

The term "derivative" as used herein in the context of a GLP-1 peptide or analogue means a chemically modified GLP-1 peptide or analogue, in which a well-defined number of substituents have been covalently attached to one or more specific amino acid residues of the peptide. The substituent(s) may be referred to as (a) side chain(s).

In a particular embodiment, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active pharmaceutical ingredient.

The side chain comprises a portion which is referred to herein as a protractor.

The protractor may be at, or near, the distant end of the side chain, relative to its point of attachment to the peptide.

In a still further particular embodiment the side chain comprises a portion in between the protractor and the point of attachment to the peptide, which portion may be referred to as a linker. The linker may consist of one or more linker elements.

In particular embodiments, the side chain and/or the protractor is lipophilic, and/or negatively charged at physiological pH (7.4).

The side chain may be covalently attached to a lysine residue of the GLP-1 peptide by acylation.

In a preferred embodiment, an active ester of the side chain is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

A derivative comprising two protractors attached to a first and a second K residue of a GLP-1 peptide (e.g., to 36Lys and 37Lys), each via a linker, may be referred to as a GLP-1 derivative which has been acylated twice, double-acylated, or dual acylated.

For the present purposes, the terms protractor, and linker may include the unreacted as well as the reacted forms of these molecules. Whether or not one or the other form is meant is clear from the context in which the term is used.

In one aspect, each protractor comprises, or consists of, a protractor selected from:

| | |
|---|---|
| HOOC—C$_6$H$_4$—O—(CH$_2$)$_y$—CO—*, and | Chem. 1: |
| HOOC—(CH$_2$)$_x$—CO—*, | Chem. 2: | wherein y is an integer in the range of 8-11, and x is 12.

In a particular embodiment, *—(CH$_2$)$_y$—* refers to straight alkylene in which y is an integer in the range of 9-11.

In another particular embodiment, *—(CH$_2$)$_x$—* refers to straight alkylene in which x is 12. This protractor may be briefly referred to as C14 diacid, i.e. a fatty α,ω dicarboxylic acid with 14 carbon atoms.

The term "fatty acid" generally refers to aliphatic monocarboxylic acids having from 4 to 28 carbon atoms, it is preferably unbranched, and/or even numbered, and it may be saturated or unsaturated.

The nomenclature is as is usual in the art, for example in the above formulas *—C$_6$H$_4$—* refers to phenylene; and *—CO—* to carbonyl (*—C(=O)—*). For example, in any formula (R—CO—*) herein (where R is as defined by each formula), R—CO—* refers to R—C(=O)—*. In a particular embodiment, the phenylene radical, may be para. In another particular embodiment the phenylene radical may be meta.

As explained above, the GLP-1 derivatives of the present invention are double-acylated, i.e. two side chains are covalently attached to the GLP-1 peptide.

In a particular embodiment, the two side chains are similar, preferably substantially identical, or, most preferably, identical.

In another particular embodiment, the two protractors are similar, preferably substantially identical, or, most preferably, identical.

In a still further particular embodiment, the two linkers are similar, preferably substantially identical, or, most preferably identical.

The term "substantially identical" includes differences from identity which are due to formation of one or more salts, esters, and/or amides; preferably formation of one or more salts, methyl esters, and simple amides; more preferably formation of no more than two salts, methyl esters, and/or simple amides; even more preferably formation of no more than one salt, methyl ester, and/or simple amide; or most preferably formation of no more than one salt.

In the context of chemical compounds such as the side chains, protractors, and linkers, similarity and/or identity may be determined using any suitable computer program and/or algorithm known in the art.

For example, the similarity of two protractors, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003). Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protractors, the two linkers, and/or the two side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b), or c) is used, the two protractors, the two linkers, and/or the two side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example 3. Chem. Inf. Model. 2008, 48, 542-549; J. Chem. Inf. Comput. Sci. 2004, 44, 170-178; 3. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

An example of a similarity calculation is inserted below, in which a known entire side chain of a known GLP-1 derivative was compared with a methyl ester thereof:

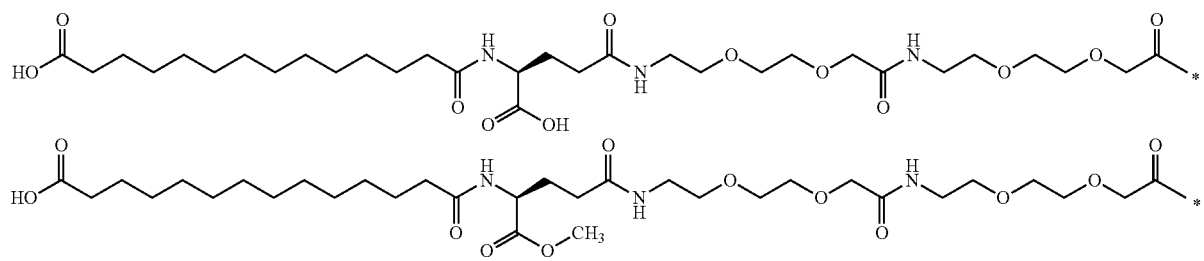

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

The linker of the derivative of the invention comprises at least one of the following linker elements:

Chem. 3:
*—NH—CH(COOH)—(CH$_2$)$_2$—CO—*,

Chem. 4:
*—NH—CH((CH$_2$)$_2$—COOH)—CO—*, and/or

Chem. 5:
*—NH—(CH$_2$)$_2$—[O—(CH$_2$)$_2$]$_k$—O—[CH$_2$]$_n$—CO—*, wherein k is an integer in the range of 1-5, and n is an integer in the range of 1-5.

The linker element of Chem. 3 may be briefly referred to as gGlu, gamma Glu, or γ-Glu. In gGlu it is the gamma carboxy group of the amino acid glutamic acid which is used for connection to another linker element, or to the epsilon-amino group of lysine.

The linker element of Chem. 4 may be briefly referred to as aGlu, alpha Glu, α-Glu, or, preferably, just Glu. In Glu it is the alpha carboxy group of the amino acid glutamic acid which is used for connection to another linker element, or to the epsilon-amino group of lysine.

In one particular embodiment the (each) gGlu linker element is in the L-form. In another particular embodiment the (each) Glu linker element is in the L-form.

In the linker element of Chem. 5, "k" and "n" may both vary between 1 and 5. When k=n=1 the structure of this linker element corresponds to Chem. 5b: Chem. 5b: *—NH—(CH$_2$)$_2$—O—(CH$_2$)$_2$—O—CH$_2$—CO—*. The linker element of Chem. 5b may be briefly referred to as Ado (8-amino-3,6-dioxaoctanoic acid) as it is a di-radical thereof.

The linker of the derivative of the invention may comprise one or more of these three different types of linker elements, and it may also comprise one or more of each individual linker element.

As a non-limiting example, the linker may consist of two Chem. 3 elements, and two Chem. 5b elements (2×Chem. 3-2×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.

Needless to say, just for the sake of good order: The phrase "in the sequence indicated" means, that the *—NH end of the first-mentioned linker element (here the first one of the two times Chem. 3) is connected to the CO—* end of the protractor, and the CO—* end of the last-mentioned linker element (here the last one of the two times Chem. 5b) is connected to the epsilon amino group of the K residue in question of the GLP-1 analogue.

The derivatives of the invention may exist in different stereo-isomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO09/030738 on p. 116-118. A preferred assay is the LOCI assay. The abbreviation LOCI refers to Luminescence Oxygen Channeling Immunoasssay, which is generally described for the determination of insulin by Poulsen and Jensen in Journal of Biomolecular Screening 2007, vol. 12, p. 240-247. In brief, donor beads are coated with streptavidin, while acceptor beads are conjugated with a monoclonal antibody recognising a mid-/C-terminal epitope of the peptide. Another monoclonal antibody, specific for the N-terminus, is biotinylated. The three reactants are combined with the analyte and forms a two-sited immuno-complex. Illumination of the complex releases singlet oxygen atoms from the donor beads, which are channeled into the acceptor beads and triggers chemiluminescence which is measured, e.g. in an Envision plate reader. The amount of light is proportional to the concentration of the compound.

Intermediate Products

The invention also relates to an intermediate product in the form of the novel backbone of the derivatives of the invention, viz. a GLP-1 peptide which comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and which has at least one of the following additional features, each as compared to GLP-1(7-37) (SEQ ID NO: 1):

i) it comprises no other Lys residues, and/or ii) it comprises at least one of (8Aib or 8Gly), 22Glu, 26Arg, 30Glu, and/or (34Arg or 34Gln); or a pharmaceutically acceptable salt, amide, or ester thereof.

Non-limiting examples of such GLP-1 peptides of the invention are the peptides of SEQ ID NOs: 2, 3, 4, 5, and 6.

The invention furthermore relates to an intermediate product in the form of a novel side chain derivative, which when attached to the peptide backbone leads to the GLP-1 derivatives of the invention. This intermediate product comprises 3-carboxyphenoxy-nonanoic acid with a protection group at the carboxy group of the nonanoic acid, optionally via a linker.

More in particular, the intermediate side chain product of the invention comprises Chem. 6:

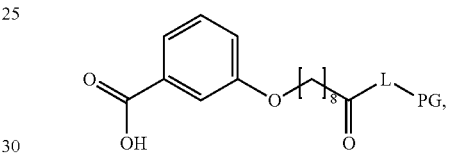

wherein L is an optional linker being a di-radical incorporating an *—NH group and a *—CO group (the *—NH group is at the left hand end of the molecule, and the *—CO group at the right hand end of the molecule), PG is a protection group; and the distal COOH group (in meta position on the aromatic ring) and/or any other COOH-group if present, is optionally also protected; or a pharmaceutically acceptable salt, amide or ester thereof.

In a particular embodiment, PG is a group that reversibly renders the compound unreactive, and that can be removed selectively.

Non-limiting examples of PG groups are —OH, or groups functionalised as an activated ester, for example, without limitation, OPfp, OPnp, and OSuc.

Other suitable activated esters may be selected, e.g., according to the teaching of M. Bodanszky, "Principles of Peptide Synthesis", 2nd ed., Springer Verlag, 1993.

Particular embodiments of the intermediate side chain product of the invention include Chem. 7 and Chem. 8:

Chem. 7

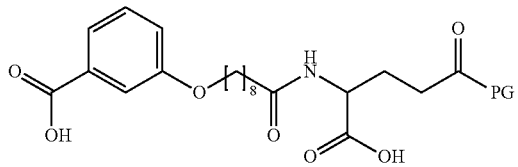

Chem. 8

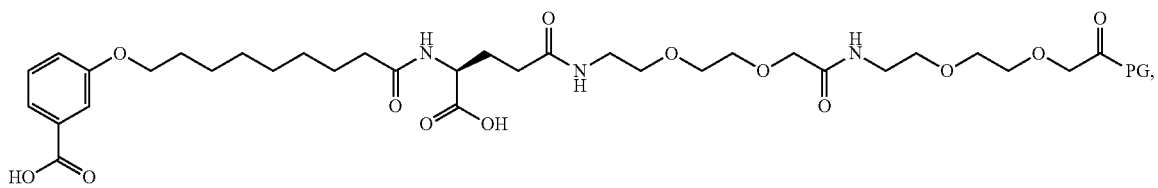

wherein i) none of the COOH groups, ii) the distal COOH group only, iii) the non-distal COOH group only, or iv) both COOH groups is/are protected; or a pharmaceutically acceptable salt, amide, or ester thereof.

The intermediate product of Chem 6. can be converted to Chem. 7, which in turn can be converted to Chem. 8 as follows:

Chem. 6 (without L, having an appropriate protecting group such as OBn at the carboxylic acid in meta position, and with an appropriate active ester CO-PG where PG derives from, e.g., N-hydroxy succinimide) can be converted to Chem. 7 by a reaction of the active ester with, e.g., H-Glu-OBn and conversion of the COOH group of Glu to an appropriate active ester such as an ester of N-hydroxy succinimide. Chem. 7 can be converted to Chem 8 by a reaction of the active ester with, e.g., H-Ado-Ado-OH and conversion of the COOH group of Ado to an appropriate active ester such as an ester of N-hydroxy succinimide.

Pharmaceutically Acceptable Salt, Amide, or Ester

The intermediate products, analogues and derivatives of the invention may be in the form of a pharmaceutically acceptable salt, amide, or ester.

Salts are e.g. formed by a chemical reaction between a base and an acid, e.g.: $2\ NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions that react with anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety.

The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group.

The ester formation may involve the free carboxylic group at the C-terminus of the peptide, and/or any free carboxylic group in the side chain.

The amide of the derivatives of the invention may, e.g., be formed by the reaction of an activated form of a free carboxylic acid group with an amine or a substituted amine, or by reaction of a free or substituted amino group with an activated form of a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

The derivatives of the invention are biologically active. For example they are very potent, and, also or alternatively, they bind very well to the GLP-1 receptor.

Also, or alternatively, they have a protracted pharmacokinetic profile. For example they have a very long terminal half-life when administered i.v. to mini pigs and/or dogs.

The particular combination of good potency/binding and long half-life is highly desirable.

Also, or alternatively, they have a high oral bioavailability. For example, when administered orally they may preferably exhibit a sufficiently high plasma-concentration for a desired period of time. Also, or alternatively, the plasma concentration may exhibit a desirable low variation (is relatively constant) in between successive administrations.

Also, or alternatively, they lead to a reduced food intake, which may be indicative of an effect on obesity and other eating disorders.

Also, or alternatively, the number of amino acid changes in the GLP-1 peptide is low.

These properties may be of importance in the development of next generation GLP-1 compounds for subcutaneous, intravenous, and/or in particular oral administration.

Also, or alternatively, it is surprising that GLP-1 analogues with two long side-chains attached to neighbouring amino acid residues in the peptide backbone are functional at all, and even more that they have an improved performance.

According to a first aspect, the derivatives and GLP-1 peptides of the invention have GLP-1 activity. For example, the derivatives of the invention have a surprisingly good potency, and/or a surprisingly good capability of binding to the human GLP-1 receptor.

In a first particular embodiment, potency and/or activity refer to in vitro potency, i.e. performance in a functional GLP-1 receptor assay, more in particular to the capability of activating the human GLP-1 receptor.

The in vitro potency may, e.g., be determined in a medium containing membranes expressing the human GLP-1 receptor, and/or in an assay with whole cells expressing the human GLP-1 receptor.

For example, the response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 29.

The $EC_{50}$ value is commonly used as a measure of potency of a drug. It refers to the concentration of the compound in question which induces a response halfway between the baseline and maximum, by reference to the dose-response curve. Popularly speaking $EC_{50}$ represents the concentration where 50% of the maximal effect is observed.

The in vitro potency of the derivatives of the invention may be determined as described above, and the $EC_{50}$ of the derivative in question determined. The lower the $EC_{50}$ value, the better the potency.

As a non-limiting example, the derivative of the invention has a potency corresponding to an $EC_{50}$ at 0% HSA of below 20 pM, preferably below 105 pM, more preferably below 5.0 pM, or even more preferably below 1.5 pM, (e.g. determined as described in Example 29).

In some embodiments, the derivatives of the invention are more potent in vitro at 0% HSA than liraglutide.

In some embodiments, the derivatives of the invention are more potent in vitro at 0% HSA than semaglutide.

In some embodiments, the in vitro potency $EC_{50}$ value of the derivative of the invention at 0% HSA is lower than 250% of that of semaglutide. An $EC_{50}$ value which is "lower than 250% of that of semaglutide" means an $EC_{50}$ value which is less than 2.5 times the $EC_{50}$ value of semaglutide, determined in the same way. This definition is applicable by analogy also for other percentage indications, as well as for similar percentage indications in relation to other parameters, such as GLP-1 receptor binding affinity ($IC_{50}$).

For these comparisons an in vitro potency test along the lines of the Example 29 test (0% HSA) is preferably used.

Also, or alternatively, the ability of the peptides and derivatives of the invention to bind to the GLP-1 receptor (receptor affinity) may be measured, and, if relevant, used as a measure of the GLP-1 activity. The receptor binding may, e.g., be measured in a competitive binding assay. In this type of assay a labelled ligand (such as $^{125}$I-GLP-1) is bound to the receptor. Each derivative is added in a series of concentrations to the human GLP-1 receptor (as e.g. contained in isolated membranes) and displacement of the labelled ligand is monitored. The receptor binding is reported as the $IC_{50}$ value, which is the concentration at which half of the labelled ligand is displaced from the receptor. This may be determined, e.g., as described in Example 30.

Generally, the binding to the GLP-1 receptor at low albumin concentration should be as good as possible, corresponding to a low $IC_{50}$ value.

As a non-limiting example, the derivative of the invention binds to the human GLP-1 receptor in vitro (at a very low concentration of albumin, such as max. 0.001% HSA) with an $IC_{50}$ value of 0.30 nM or below. For example, the derivatives of the invention are better at binding to the human GLP-1 receptor than liraglutide, where for these comparisons an in vitro receptor binding test along the lines of the Example 30 test (0.001% HSA) is preferably used.

In a second particular embodiment, potency and/or activity refer to in vivo potency. The peptides and derivatives of the invention are potent in vivo, which may be determined as is known in the art in any suitable animal model, as well as in clinical trials.

The diabetic db/db mouse is one example of a suitable animal model, and the blood glucose lowering effect, and/or the body weight lowering effect may be determined in such mice in vivo.

The LYD pig is another example of a suitable animal model, and the reduction in food intake may be determined in a PD study in such pigs in vivo. For example, when the derivatives of the invention are administered in a single dose s.c. to pigs as described in Example 34, they have the effect of reducing food intake (as compared to a vehicle-treated control group).

According to a second aspect, the derivatives of the invention are protracted. Protraction may be estimated in vitro, and/or determined from pharmacokinetic in vivo studies.

The ability of the derivatives of the invention to bind to the GLP-1 receptor in the presence of a low and a high concentration of albumin, respectively, may be determined as described in Example 30.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their residence in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

Also, or alternatively, the binding of the derivatives to albumin may be measured using the in vitro potency assay of Example 29, which may be performed in the absence of serum albumin as well as in the presence of serum albumin. An increase of the in vitro potency, $EC_{50}$ value, in the presence of serum albumin indicates an affinity to serum albumin and represents a method to predict a protracted pharmacokinetic profile of the test substance in animal models.

Protraction may be determined, e.g., as terminal half-life (t½) after i.v. administration to, e.g., mini pigs or dogs.

As a non-limiting example, the derivative of the invention has a terminal half-life after i.v. administration to mini pigs of at least 60 hours, more preferably at least 65 hours, or most preferably at least 70 hours (determined, e.g., as described in Example 31).

As another non-limiting example, the derivative of the invention has a terminal half-life after i.v. administration to beagle dogs of at least 60 hours, more preferably at least 65 hours, or most preferably at least 70 hours (determined, e.g., as described in Example 32).

For example, the derivatives of the invention have longer half-lives after i.v. administration to mini pigs and/or beagle dogs than liraglutide, and/or than semaglutide, where for these comparisons PK studies along the lines of those of Examples 31 and 32 are preferably used.

Increasing terminal half-life and/or decreasing of the clearance means that the compound in question is eliminated slower from the body. For the derivatives of the invention this entails an extended duration of pharmacological effect.

The pharmacokinetic properties of the derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the derivatives of the invention.

In such studies, animals are typically administered with a single dose of the drug, either intravenously, subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, $3^{rd}$ edition, 1995 Williams Wilkins).

The estimate of terminal half-life and/or clearance is relevant for evaluation of dosing regimens and an important parameter in drug development, in the evaluation of new drug compounds.

According to a third aspect, the derivatives of the invention are protracted and at the same time have a very good potency. The particular combination of good potency/binding and long half-life may be highly desirable. For example, when administered orally such compounds may exhibit a sufficiently high plasma-concentration for a desired period of time, and also, or alternatively, the plasma concentration may exhibit a desirable low variation (is relatively constant) in between successive administrations.

According to a fourth aspect, the derivatives of the invention have a high oral bioavailability.

Oral bioavailability (or p.o. bioavailability) may, e.g., be determined in Beagle dogs as described in Example 32. The oral tablets containing the GLP-1 derivative as the active pharmaceutical ingredient (API) may be prepared as described in Example 33.

As a non-limiting example, the derivative of the invention when administered p.o. to Beagle dogs in a tablet composition as described in Example 33 has an oral bioavailability which is higher than that of semaglutide when administered p.o. to Beagle dogs in a similar tablet formulation, where similar means identical except for the active pharmaceutical ingredient. In one embodiment, the oral bioavailability of the derivative of the invention corresponds to an F value of at least 1.5%.

Generally, the term bioavailability refers to the fraction of an administered dose of an active pharmaceutical ingredient (API), such as a derivative of the invention that reaches the systemic circulation unchanged. By definition, when an API is administered intravenously, its bioavailability is 100%. However, when it is administered via other routes (such as orally), its bioavailability decreases (due to degradation and/or incomplete absorption and first-pass metabolism). Knowledge about bioavailability is important when calculating dosages for non-intravenous routes of administration.

Absolute oral bioavailability compares the bioavailability (estimated as the area under the curve, or AUC) of the API in systemic circulation following oral administration, with the bioavailability of the same API following intravenous administration. It is the fraction of the API absorbed through non-intravenous administration compared with the corresponding intravenous administration of the same API. The comparison must be dose normalised if different doses are used; consequently, each AUC is corrected by dividing by the corresponding dose administered.

A plasma API concentration vs time plot is made after both oral and intravenous administration. The absolute bioavailability (F) is the dose-corrected AUC-oral divided by AUC-intravenous.

Before testing oral bioavailability the derivatives of the invention may suitably be formulated as is known in the art of oral formulations of insulinotropic compounds, e.g. using any one or more of the formulations described in WO 2008/145728, or, preferably, as described in Example 33 herein.

According to a fifth aspect, the derivatives of the invention have good biophysical properties. These properties include but are not limited to physical stability and/or solubility. These and other biophysical properties may be measured using standard methods known in the art of protein chemistry. In a particular embodiment, these properties are improved as compared to native GLP-1 (SEQ ID NO: 1). Changed oligomeric properties of the derivatives may be at least partly responsible for the improved biophysical properties.

Additional particular embodiments of the derivatives of the invention are described in the sections headed "PARTICULAR EMBODIMENTS" before the experimental section.

Production Processes

The production of peptides like GLP-1(7-37) and analogues thereof is well known in the art.

The GLP-1 peptides of the derivatives of the invention, viz. GLP-1(7-37) or an analogue thereof, may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli*, *Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 (7724) entitled "Semi-recombinant preparation of GLP-1 analogues". Specific examples of methods of preparing a number of the derivatives of the invention are included in the experimental part.

Pharmaceutical Compositions

Pharmaceutical compositions comprising a derivative of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. $19^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations, i.e. formulations comprising water. A liquid formulation may be a solution, or a suspension. An aqueous formulation typically comprises at least 50% w/w water, or at least 60%, 70%, 80%, or even at least 90% w/w of water.

Alternatively a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml.

A pharmaceutical composition may comprise an isotonic agent. The isotonic agent may e.g. be selected from the group consisting of a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the peptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the peptide is a polypeptide comprising at least one methionine residue susceptible to such oxidation. Any stereoisomer of methionine (L or D) or combinations thereof can be used.

A pharmaceutical composition may comprise a stabiliser selected from the group of high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants, for example a surfactant, at least one surfactant, or different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

In some embodiments the present invention relates to a pharmaceutical composition, e.g. in the form of a tablet, comprising a GLP-1 derivative of the present invention and an absorption enhancer selected from SNAC and sodium caprate. SNAC is the sodium salt of N-(8-(2-hydroxybenzoyl)amino)caprylic acid and may be prepared using the method described in e.g. WO96/030036.

An administered dose may contain from 0.01 mg-100 mg of the derivative, or from 0.01-50 mg, or from 0.01-20 mg, or from 0.01 mg-10 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. In a particular embodiment the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant. A composition may further be compounded in a drug carrier or drug delivery system, e.g. in order to improve stability, bioavailability, and/or solubility. A composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally. A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, LCMS, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), gastric inhibitory polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonists, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, gastric inhibitory polypeptide agonists or antagonists, gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention for use as a medicament.

In particular embodiments, the derivative of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as overweight and/or obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying (for more detailed embodiments, see Re (v), below);

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

Re (v):

In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight.

Body mass index (BMI) is a measure of body fat based on height and weight.

The formula for calculation is BMI=weight in kilograms/height in meters$^2$.

Obesity: In some embodiments the subject suffering from obesity is human, such as an adult human or a paediatric human (including infants, children, and adolescents). A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

Overweight: In some embodiments the invention relates to use of the derivatives of the invention for treatment or prevention of overweight, optionally in the presence of at least one weight-related comorbidity.

In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

Reduction of bodyweight: In some embodiments the invention relates to use of the derivatives of the invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, Type 1 diabetes, and/or eating disorders (such as, in particular, obesity, overweight, and reduction of bodyweight).

Particular Embodiments

The following are particular embodiments of the invention:

1. A derivative of a GLP-1 peptide, which peptide comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and a maximum of seven amino acid changes as compared to GLP-1 (7-37) (SEQ ID NO: 1);

which derivative comprises two protractors attached to said first and second Lys residue, respectively, each via a linker; wherein
the protractor is selected from:

HOOC—C$_6$H$_4$—O—(CH$_2$)$_y$—CO—*,  Chem. 1:

HOOC—(CH$_2$)$_x$—CO—*,  Chem. 2:

wherein y is an integer in the range of 8-11, and x is 12; and
the linker comprises at least one of:

*—NH—CH(COOH)—(CH$_2$)$_2$—CO—*,  Chem. 3:

*—NH—CH((CH$_2$)$_2$—COOH)—CO—*, and/or  Chem. 4:

*—NH—(CH$_2$)$_2$—[O—(CH$_2$)$_2$]$_k$—O—[CH$_2$]$_n$—CO—*,  Chem. 5:

wherein k is an integer in the range of 1-5, and n is an integer in the range of 1-5;
or a pharmaceutically acceptable salt, amide, or ester thereof.

2. The derivative of embodiment 1, wherein the protractor is Chem. 1.

3. The derivative of any of embodiments 1-2, wherein the protractor is selected from:

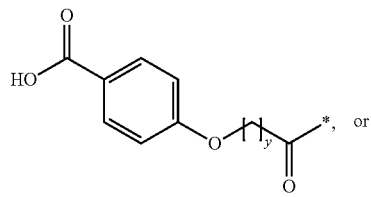

Chem. 1a

, or

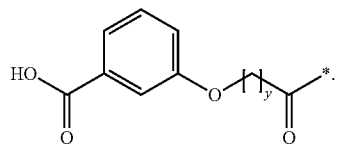

Chem. 1b

4. The derivative of any of embodiments 1-3, wherein the protractor is Chem. 1a:

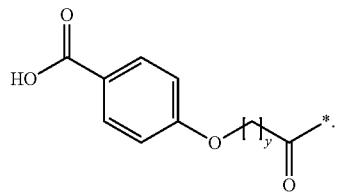

5. The derivative of any of embodiments 1-3, wherein the protractor is Chem. 1b:

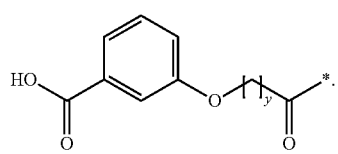

6. The derivative of any of embodiments 1-5, wherein y is 8, 9, 10, or 11.

7. The derivative of any of embodiments 1-6, wherein y is 8.

8. The derivative of any of embodiments 1-6, wherein y is 9.

9. The derivative of any of embodiments 1-6, wherein y is 10.

10. The derivative of any of embodiments 1-6, wherein y is 11.

11. The derivative of embodiment 1, wherein the protractor is Chem. 2.

12. The derivative of any of embodiments 1-11, wherein the linker comprises Chem. 5.

13. The derivative of any of embodiments 1-12, wherein the linker comprises Chem. 5a:

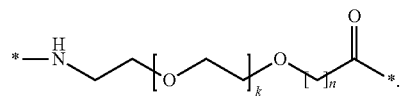

14. The derivative of any of embodiments 1-13, wherein k=n=1.

15. The derivative of any of embodiments 1-14, wherein the linker comprises

*—NH—(CH$_2$)$_2$—O—(CH$_2$)$_2$—O—CH—CO—*.  Chem. 5b:

16. The derivative of any of embodiments 1-15, wherein Chem. 5 is included one, two, three, or four times.

17. The derivative of any of embodiments 1-16, wherein Chem. 5 is included one time.

18. The derivative of any of embodiments 1-16, wherein Chem. 5 is included two times.

19. The derivative of any of embodiments 1-16, wherein Chem. 5 is included three times.

20. The derivative of any of embodiments 1-16, wherein Chem. 5 is included four times.

21. The derivative of any of embodiments 1-16, wherein Chem. 5a is included one, two, three, or four times.

22. The derivative of any of embodiments 1-16, or 21, wherein Chem. 5a is included one time.

23. The derivative of any of embodiments 1-16, or 21, wherein Chem. 5a is included two times.

24. The derivative of any of embodiments 1-16, or 21, wherein Chem. 5a is included three times.

25. The derivative of any of embodiments 1-16 or 21, wherein Chem. 5a is included four times.

26. The derivative of any of embodiments 1-16, wherein Chem. 5b is included one, two, three, or four times.

27. The derivative of any of embodiments 1-16, or 26, wherein Chem. 5b is included one time.

28. The derivative of any of embodiments 1-16, or 26, wherein Chem. 5b is included two times.

29. The derivative of any of embodiments 1-16, or 26, wherein Chem. 5b is included three times.

30. The derivative of any of embodiments 1-16, or 26, wherein Chem. 5b is included four times.

31. The derivative of any of embodiments 1-30, wherein the linker comprises Chem. 3.

32. The derivative of any of embodiments 1-31, wherein the linker comprises Chem. 3a:

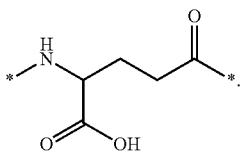

33. The derivative of any of embodiments 1-32 wherein Chem. 3 is not included, included one time, included two times, or included three times.
34. The derivative of any of embodiments 1-33, wherein Chem. 3 is not included.
35. The derivative of any of embodiments 1-33, wherein Chem. 3 is included one time.
36. The derivative of any of embodiments 1-33, wherein Chem. 3 is included two times.
37. The derivative of any of embodiments 1-33, wherein Chem. 3 is included three times.
38. The derivative of any of embodiments 1-37, wherein Chem. 3a is not included, included one time, included two times, or included three times.
39. The derivative of any of embodiments 1-33, or 38, wherein Chem. 3a is not included.
40. The derivative of any of embodiments 1-33, or 38, wherein Chem. 3a is included one time.
41. The derivative of any of embodiments 1-33, or 38, wherein Chem. 3a is included two times.
42. The derivative of any of embodiments 1-33, or 38, wherein Chem. 3a is included three times.
43. The derivative of any of embodiments 1-34, or 38-39, wherein the linker comprises Chem. 4.
44. The derivative of embodiment 43, wherein the linker comprises Chem. 4a:

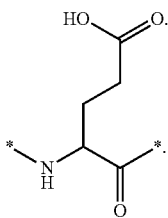

45. The derivative of any of embodiments 43-44, wherein Chem. 4 is not included, or included two times.
46. The derivative of any of embodiments 43-45, wherein Chem. 4 is not included.
47. The derivative of any of embodiments 43-45, wherein Chem. 4 is included two times.
48. The derivative of embodiment 44, wherein Chem. 4a is not included, or included two times.
49. The derivative of any of embodiments 44 or 48, wherein Chem. 4a is not included.
50. The derivative of any of embodiments 44 or 48, wherein Chem. 4a is included two times.
51. The derivative of any of embodiments 1-50, wherein the linker consists of two Chem. 3 elements, and two Chem. 5b elements (2×Chem. 3-2×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.
52. The derivative of any of embodiments 1-50, wherein the linker consists of two Chem. 3a elements, and two Chem. 5a elements where n=k=1 (2×Chem. 3a-2×Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.
53. The derivative of any of embodiments 1-50, wherein the linker consists of one Chem. 3 element, and two Chem. 5b elements (Chem. 3-2×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.
54. The derivative of any of embodiments 1-50, wherein the linker consists of one Chem. 3a element, and two Chem. 5a elements where n=k=1 (Chem. 3a-2×Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.
55. The derivative of any of embodiments 1-50, wherein the linker consists of one Chem. 3 element, and three Chem. 5b elements (Chem. 3-3×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.
56. The derivative of any of embodiments 1-50, wherein the linker consists of one Chem. 3a element, and three Chem. 5a elements where n=k=1 (Chem. 3a-3×Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.
57. The derivative of any of embodiments 1-50, wherein the linker consists of two Chem. 4 elements, and one Chem. 5b element (2×Chem. 4-Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.
58. The derivative of any of embodiments 1-50, wherein the linker consists of two Chem. 4a elements, and one Chem. 5a element where n=k=1 (2×Chem. 4a-Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.
59. The derivative of any of embodiments 1-50, wherein the linker consists of three Chem. 3 elements, and two Chem. 5b elements (3×Chem. 3-2×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.
60. The derivative of any of embodiments 1-50, wherein the linker consists of three Chem. 3a elements, and two Chem. 5a elements where n=k=1 (3×Chem. 3a-2×Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.
61. The derivative of any of embodiments 1-50, wherein the linker consists of one Chem. 3 element, and four Chem. 5b elements (Chem. 3-4×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.

62. The derivative of any of embodiments 1-50, wherein the linker consists of one Chem. 3a element, and four Chem. 5a elements where n=k=1 (Chem. 3a-4×Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.

63. The derivative of any of embodiments 1-62, wherein the linker and the protractor are interconnected via an amide bond.

64. The derivative of any of embodiments 1-63, wherein the linker and the GLP-1 peptide are interconnected via an amide bond.

65. The derivative of any of embodiments 1-64, wherein the CO—* end of the linker forms an amide bond with the epsilon-amino group of the first or the second Lys residue.

66. The derivative of any of embodiments 1-65, wherein the two protractors are substantially identical, preferably identical.

67. The derivative of any of embodiments 1-66, wherein the two protractors have a similarity of at least 0.5; preferably at least 0.6; more preferably at least 0.7, or at least 0.8; even more preferably at least 0.9; or most preferably at least 0.99, such as a similarity of 1.0.

68. The derivative of any of embodiments 1-677, wherein the two linkers are substantially identical, preferably identical.

69. The derivative of any of embodiments 1-688, wherein the two linkers have a similarity of at least 0.5; preferably at least 0.6; more preferably at least 0.7, or at least 0.8; even more preferably at least 0.9; or most preferably at least 0.99, such as a similarity of 1.0.

70. The derivative of any of embodiments 1-69, wherein the two side chains consisting of protractor and linker are substantially identical, preferably identical.

711. The derivative of any of embodiments 1-70, wherein the two side chains consisting of protractor and linker have a similarity of at least 0.5; preferably at least 0.6; more preferably at least 0.7, or at least 0.8; even more preferably at least 0.9; or most preferably at least 0.99, such as a similarity of 1.0.

72. The derivative of any of embodiments 66-711, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity of the two fingerprints.

73. The derivative of any of embodiments 1-72, wherein the first Lys residue is designated 36Lys.

74. The derivative of any of embodiments 1-73, wherein the second Lys residue is designated 37Lys.

75. The derivative of any of embodiments 1-74 wherein the position corresponding to position 36 of GLP-1(7-37) (SEQ ID NO: 1) is identified by handwriting and eyeballing.

76. The derivative of any of embodiments 1-66, wherein the position corresponding to position 37 of GLP-1(7-37) (SEQ ID NO: 1) is identified by handwriting and eyeballing.

77. The derivative of any of embodiments 1-76, wherein the total number of amino acid changes as compared to GLP-1(7-37) (SEQ ID NO: 1) are identified by handwriting and eyeballing.

78. The derivative of any of embodiments 1-77, wherein the position corresponding to position 36 of GLP-1(7-37) (SEQ ID NO: 1) is identified by use of a standard protein or peptide alignment program.

79. The derivative of any of embodiments 1-78, wherein the position corresponding to position 37 of GLP-1(7-37) (SEQ ID NO: 1) is identified by use of a standard protein or peptide alignment program.

80. The derivative of any of embodiments 1-79, wherein the number of amino acid changes as compared to GLP-1(7-37) (SEQ ID NO: 1) are identified by use of a standard protein or peptide alignment program.

81. The derivative of any of embodiments 78-80, wherein the alignment program is a Needleman-Wunsch alignment.

82. The derivative of any of embodiments 78-81, wherein the default scoring matrix and the default identity matrix is used.

83. The derivative of any of embodiments 78-82, wherein the scoring matrix is BLOSUM62.

84. The derivative of any of embodiments 78-83, wherein the penalty for the first residue in a gap is −10 (minus ten).

85. The derivative of any of embodiments 78-84, wherein the penalties for additional residues in a gap is −0.5 (minus point five).

86. The derivative of any of embodiments 1-85, wherein the GLP-1 peptide is an analogue of GLP-1(7-37) (SEQ ID NO: 1) that comprises at least the substitutions R36K and G37K.

87. The derivative of any of embodiments 1-86, wherein the GLP-1 peptide comprises no Lys residues other than 36Lys and 37Lys.

88. The derivative of any of embodiments 1-87, wherein the GLP-1 peptide has a maximum of five amino acid changes as compared to GLP-1(7-37) (SEQ ID NO: 1).

89. The derivative of any of embodiments 1-87, wherein the GLP-1 peptide has a maximum of six amino acid changes as compared to GLP-1(7-37) (SEQ ID NO: 1).

90. The derivative of any of embodiments 1-87, or 89, wherein the GLP-1 peptide has a minimum of five amino acid changes as compared to GLP-1(7-37) (SEQ ID NO: 1).

91. The derivative of any of embodiments 1-87, wherein the GLP-1 peptide has a minimum of six amino acid changes as compared to GLP-1(7-37) (SEQ ID NO: 1).

92. The derivative of any of embodiments 1-87, wherein the GLP-1 peptide has a minimum of seven amino acid changes as compared to GLP-1(7-37) (SEQ ID NO: 1).

93. The derivative of any of embodiments 1-87, wherein the GLP-1 peptide has five, six, or seven amino acid changes as compared to GLP-1(7-37) (SEQ ID NO: 1).

94. The derivative of any of embodiments 1-87, wherein the GLP-1 peptide has five amino acid changes as compared to GLP-1(7-37) (SEQ ID NO: 1).

95. The derivative of any of embodiments 1-87, wherein the GLP-1 peptide has six amino acid changes as compared to GLP-1(7-37) (SEQ ID NO: 1).

96. The derivative of any of embodiments 1-87, wherein the GLP-1 peptide has seven amino acid changes as compared to GLP-1(7-37) (SEQ ID NO: 1).

97. The derivative of any of embodiments 1-96, wherein the maximum number of amino acid changes, the minimum number of amino acid changes, and/or the number of amino acid changes includes the two amino acid changes into 36Lys and 37Lys.

98. The derivative of any of embodiments 1-97, wherein the amino acid changes are at one or more positions corresponding to one or more of positions 8, 22, 26, 30, 34, 36, and 37 of GLP-1(7-37) (SEQ ID NO: 1).

99. The derivative of any of embodiments 1-98, wherein the peptide comprises 36Lys and 37Lys, and optionally one or more of the following further amino acid changes: 8Gly, 8Aib, 22Glu, 26Arg, 30Glu, and/or (34Arg or 34Gln).

100. The derivative of any of embodiments 1-99, wherein the peptide comprises 8Aib.
101. The derivative of any of embodiments 1-99, wherein the peptide comprises 8Gly.
102. The derivative of any of embodiments 1-99, wherein the peptide does not comprise 8Gly.
103. The derivative of any of embodiments 1-102, wherein the peptide comprises 22Glu.
104. The derivative of any of embodiments 1-103, wherein the peptide comprises 26Arg.
105. The derivative of any of embodiments 1-104, wherein the peptide comprises 30Glu.
106. The derivative of any of embodiments 1-105, wherein the peptide comprises 34Arg.
107. The derivative of any of embodiments 1-105, wherein the peptide comprises 34Gln.
108. The derivative of any of embodiments 1-107, wherein, for determination of the changes in the peptide, the amino acid sequence of the peptide is compared to the amino acid sequence of native GLP-1(7-37) (SEQ ID NO: 1).
109. The derivative of any of embodiments 1-108, wherein, for determination of a position in a peptide which corresponds to a specified position in native GLP-1(7-37) (SEQ ID NO: 1), the amino acid sequence of the peptide is compared to the amino acid sequence of native GLP-1(7-37) (SEQ ID NO: 1).
110. The derivative of any of embodiments 1-109, wherein the comparison of the amino acid sequence of the peptide with that of GLP-1(7-37) (SEQ ID NO: 1) is done by handwriting and eyeballing.
111. The derivative of any of embodiments 1-110, wherein the comparison of the amino acid sequence of the peptide with that of GLP-1(7-37) (SEQ ID NO: 1) is done by use of a standard protein or peptide alignment program.
112. The derivative of embodiment 111, wherein the alignment program is a Needleman-Wunsch alignment.
113. The derivative of any of embodiments 111-112, wherein the default scoring matrix and the default identity matrix is used.
114. The derivative of any of embodiments 111-113, wherein the scoring matrix is BLOSUM62.
115. The derivative of any of embodiments 111-114, wherein the penalty for the first residue in a gap is −10 (minus ten).
116. The derivative of any of embodiments 111-115, wherein the penalties for additional residues in a gap is −0.5 (minus point five).
117. The derivative of any of embodiments 1-116, wherein the position corresponding to any of the indicated positions of GLP-1(7-37) (SEQ ID NO: 1) is identified by handwriting and eyeballing.
118. The derivative of any of embodiments 1-117, wherein the position corresponding to any of the indicated positions of GLP-1(7-37) (SEQ ID NO: 1) is identified as described for position 36 and position 37 in any of embodiments 78-85.
119. The derivative of any of embodiments 1-118, wherein the GLP-1 peptide a) comprises a GLP-1 compound of Formula I; and/or b) is a GLP-1 compound of Formula I:
Formula I: Xaa$_7$-Xaa$_8$-Glu-Gly-Thr-Phe-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Lys$_{36}$-Lys$_{37}$ (SEQ ID NO: 7), wherein
Xaa$_7$ is L-histidine, (S)-2-Hydroxy-3-(1H-imidazol-4-yl)-propionic acid, D-histidine, desamino-histidine (desH), N$^\alpha$-acetyl-histidine, N$^\alpha$-formyl-histidine;
Xaa$_8$ is Ala, Gly, Ser, Aib, (1-aminocyclopropyl) carboxylic acid, (1-aminocyclobutyl) carboxylic acid;
Xaa$_{16}$ is Val or Leu;
Xaa$_{18}$ is Ser or Arg;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg or Lys;
Xaa$_{27}$ is Glu or Leu;
Xaa$_{30}$ is Ala, or Glu;
Xaa$_{31}$ is Trp or His;
Xaa$_{33}$ is Val or Arg;
Xaa$_{34}$ is Arg, Lys, His, Asn, or Gln; and
Xaa$_{35}$ is Gly or Aib.
120. The derivative of embodiment 119, wherein Xaa$_7$ is His; Xaa$_8$ is Gly or Aib; Xaa$_{16}$ is Val; Xaa$_{18}$ is Ser; Xaa$_{19}$ is Tyr; Xaa$_{20}$ is Leu; Xaa$_{22}$ is Gly or Glu; Xaa$_{23}$ is Gln; Xaa$_{25}$ is Ala; Xaa$_{26}$ is Arg; Xaa$_{27}$ is Glu; Xaa$_{30}$ is Ala or Glu; Xaa$_{31}$ is Trp; Xaa$_{33}$ is Val; Xaa$_{34}$ is Arg or Gln; and Xaa$_{35}$ is Gly.
121. The derivative of any of embodiments 1-118, wherein the GLP-1 peptide a) comprises a GLP-1 compound of Formula II; and/or b) is a GLP-1 compound of Formula II:
Formula II: Xaa$_7$-Xaa$_8$-Glu-Gly-Thr-Phe-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Lys$_{36}$-Lys$_{37}$ (SEQ ID NO: 8), wherein
Xaa$_7$ is L-histidine, (S)-2-Hydroxy-3-(1H-imidazol-4-yl)-propionic acid, D-histidine, desamino-histidine (desH), N$^\alpha$-acetyl-histidine, N$^\alpha$-formyl-histidine;
Xaa$_8$ is Ala, Ser, Aib, (1-aminocyclopropyl) carboxylic acid, (1-aminocyclobutyl) carboxylic acid;
Xaa$_{16}$ is Val or Leu;
Xaa$_{18}$ is Ser or Arg;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg or Lys;
Xaa$_{27}$ is Glu or Leu;
Xaa$_{30}$ is Ala, or Glu;
Xaa$_{31}$ is Trp or His;
Xaa$_{33}$ is Val or Arg;
Xaa$_{34}$ is Arg, Lys, His, Asn, or Gln; and
Xaa$_{35}$ is Gly or Aib.
122. The derivative of embodiment 121, wherein Xaa$_7$ is His; Xaa$_8$ is Aib; Xaa$_{16}$ is Val; Xaa$_{18}$ is Ser; Xaa$_{19}$ is Tyr; Xaa$_{20}$ is Leu; Xaa$_{22}$ is Gly or Glu; Xaa$_{23}$ is Gln; Xaa$_{25}$ is Ala; Xaa$_{26}$ is Arg; Xaa$_{27}$ is Glu; Xaa$_{30}$ is Ala or Glu; Xaa$_{31}$ is Trp; Xaa$_{33}$ is Val; Xaa$_{34}$ is Arg or Gln; and Xaa$_{35}$ is Gly.
123. The derivative of any of embodiments 119-122, wherein the GLP-1 compound of Formula I, or the GLP-1 compound or Formula II, respectively, is an analogue of GLP-1(7-37) (SEQ ID NO: 1).
124. The derivative of any of embodiments 119-123, wherein Xaa$_7$ is His.
125. The derivative of any of embodiments 119-124, wherein Xaa$_8$ is Aib.
126. The derivative of any of embodiments 119-120, or 123-124, wherein Xaa$_8$ is Gly.
127. The derivative of any of embodiments 119-126, wherein Xaa$_{16}$ is Val.
128. The derivative of any of embodiments 119-126, wherein Xaa$_{18}$ is Ser.

129. The derivative of any of embodiments 119-128, wherein $Xaa_{19}$ is Tyr.
130. The derivative of any of embodiments 119-129, wherein $Xaa_{20}$ is Leu.
131. The derivative of any of embodiments 119-130, wherein $Xaa_{22}$ is Gly.
132. The derivative of any of embodiments 119-130, wherein $Xaa_{22}$ is Glu.
133. The derivative of any of embodiments 119-132, wherein $Xaa_{23}$ is Gln.
134. The derivative of any of embodiments 119-133, wherein $Xaa_{25}$ is Ala.
135. The derivative of any of embodiments 119-134, wherein $Xaa_{26}$ is Arg.
136. The derivative of any of embodiments 119-135, wherein $Xaa_{27}$ is Glu.
137. The derivative of any of embodiments 119-136, wherein $Xaa_{30}$ is Ala.
138. The derivative of any of embodiments 119-136, wherein $Xaa_{30}$ is Glu.
139. The derivative of any of embodiments 119-138, wherein $Xaa_{31}$ is Trp.
140. The derivative of any of embodiments 119-139, wherein $Xaa_{33}$ is Val.
141. The derivative of any of embodiments 119-140, wherein $Xaa_{34}$ is Arg.
142. The derivative of any of embodiments 119-140, wherein $Xaa_{34}$ is Gln.
143. The derivative of any of embodiments 119-142, wherein $Xaa_{35}$ is Gly.
144. The derivative of any of embodiments 1-143, wherein the peptide comprises the following amino acid changes, as compared to GLP-1(7-37) (SEQ ID NO: 1): (i) 8Aib, 22Glu, 26Arg, 34Arg, 36Lys, and 37Lys; (ii) 8Aib, 26Arg, 34Arg, 36Lys, and 37Lys; (iii) 8Aib, 22Glu, 26Arg, 34Gln, 36Lys, and 37Lys; (iv) 8Gly, 22Glu, 26Arg, 34Arg, 36Lys, 37Lys; or (v) 8Aib, 22Glu, 26Arg, 30Glu, 34Arg, 36Lys, 37Lys.
145. The derivative of any of embodiments 1-144, wherein the peptide has the following amino acid changes, as compared to GLP-1(7-37) (SEQ ID NO:1): (i) 8Aib, 22Glu, 26Arg, 34Arg, 36Lys, and 37Lys; (ii) 8Aib, 26Arg, 34Arg, 36Lys, and 37Lys; or (iii) 8Aib, 22Glu, 26Arg, 34Gln, 36Lys, and 37Lys; (iv) 8Gly, 22Glu, 26Arg, 34Arg, 36Lys, 37Lys; or (v) 8Aib, 22Glu, 26Arg, 30Glu, 34Arg, 36Lys, 37Lys.
146. The derivative of any of embodiments 1-145, wherein the peptide is SEQ ID NO: 2, SEQ ID NO: 3, SEQ ID NO: 4, SEQ ID NO: 5, or SEQ ID NO: 6.
147. A compound, preferably a GLP-1 derivative according to any of embodiments 1-146, selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, or Chem. 48; or a pharmaceutically acceptable salt, amide, or ester thereof.
148. A compound, preferably a compound of embodiment 147, characterised by its name, and selected from a listing of each of the names of the compounds of Examples 1-28 herein; or a pharmaceutically acceptable salt, amide, or ester thereof.
149. The derivative of any of embodiments 1-148, which has GLP-1 activity.
150. The derivative of embodiment 149, wherein GLP-1 activity refers to the capability of activating the human GLP-1 receptor.
151. The derivative of embodiment 150, wherein activation of the human GLP-1 receptor is measured in an in vitro assay, as the potency of cAMP production.
152. The derivative of any of embodiments 149-151, wherein activation of the human GLP-1 receptor is measured in an in vitro assay, in a reporter gene assay.
153. The derivative of any of embodiments 149-152, wherein the assay is performed in a stably transfected BHK cell line that expresses the human GLP-1 receptor and contains the DNA for the cAMP response element (CRE) coupled to a promoter and the gene for firefly luciferase (CRE luciferase).
154. The derivative of embodiment 153, wherein when assay incubation is completed luciferin is added and luminescence is measured.
155. The derivative of any of embodiments 149-154, wherein the assay is performed in the absence of serum albumin (0% HSA, final assay concentration).
156. The derivative of any of embodiments 149-155, wherein the assay is performed in the presence of serum albumin (1.0% HSA, final assay concentration).
157. The derivative of any of embodiments 149-156, wherein the cells are BHK cells with BHKTS13 as a parent cell line.
158. The derivative of any of embodiments 149-157, wherein the cells are derived from clone FCW467-12A.
159. The derivative of any of embodiments 149-158, wherein the cells are cultured at 5% $CO_2$ in Cell Culture Medium, aliquoted and stored in liquid nitrogen.
160. The derivative of embodiment 159, wherein the Cell Culture Medium is DMEM medium with 10% FBS (Fetal Bovine Serum), 1 mg/ml G418, 240 nM MTX (methotrexate) and 1% pen/strep (penicillin/streptomycin).
160. The derivative of any of embodiments 149-159, wherein before each assay a cell culture aliquot is taken up and washed twice in PBS before being suspended at the desired concentration in the assay specific buffer.
161. The derivative of any of embodiments 149-160, wherein for 96-well plates the suspension is made to give a final concentration of $5 \times 10^3$ cells/well.
162. The derivative of any of embodiments 160-161, wherein the assay specific buffer is 1% Assay Buffer, which consists of 2% ovalbumin, 0.2% Pluronic F-68 and 2% HSA in Assay Medium.
163. The derivative of any of embodiments 160-161, wherein the Assay Buffer is 0% Assay Buffer, which consists of 2% ovalbumin and 0.2% Pluronic F-68 in Assay Medium.
164. The derivative of any of embodiments 162-163, wherein Assay Medium consists of DMEM w/o phenol red, 10 mM Hepes and 1× Glutamax.
165. The derivative of any of embodiments 149-164, wherein the assay procedure comprises the following steps:
i) Cell stocks are thawed in a 37° C. water bath;
ii) cells are washed three times in PBS;
iii) the cells are counted and adjusted to $5 \times 10^3$ cells/50 µl ($1 \times 10^5$ cells/ml) in Assay Medium, and a 50 µl aliquot of cells is transferred to each well in the assay plate;
iv) stocks of the test compounds and reference compounds, if any, are diluted to a concentration of 0.2 µM in 0% Assay Buffer for the 0% HSA assay or 1% Assay Buffer for the 1% HSA assay; and compounds are diluted 10-fold to give a suitable range of concentrations (such as: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M, $2 \times 10^{-13}$ M, and $2 \times 10^{-14}$ M), and for each compound a blank assay buffer control is also included;
v) a 50 µl aliquot of compound or blank is transferred in triplicate from the dilution plate to the assay plate, and compounds are tested at suitable concentrations (such as the following final concentrations: $1\times10^{-7}$ M, $1\times10^{-8}$ M; $1\times10^{-9}$ M, $1\times10^{-10}$ M, $1\times10^{-11}$ M, $1\times10^{-12}$ M, $1\times10^{-13}$ M, and $1\times10^{-14}$ M);

vi) the assay plate is incubated for 3 h in a 5% $CO_2$ incubator at 37° C.;

vii) the assay plate is removed from the incubator and allowed to stand at room temperature for 15 min;

ixx) a 100 µl aliquot of luciferin (such as steadylite plus reagent) is added to each well of the assay plate;

ix) each assay plate is covered to protect it from light and shaken for 30 min at room temperature; and x) each assay plate is read, for example in a Packard TopCount NXT instrument.

166. The derivative of embodiment 165, wherein the data e.g. from the TopCount instrument are transferred to suitable software such as GraphPad Prism 5 for desired calculations.

167. The derivative of any of embodiments 149-166, wherein values for each triplicate is averaged, a non-linear regression performed, and the $EC_{50}$ values calculated.

168. The derivative of any of embodiments 131-167, wherein the regression is log(agonist) vs response.

169. The derivative of any of embodiments 149-151, wherein the potency is determined as described in any of embodiments 152-153.

170. The derivative of any of embodiments 149-169, wherein the potency is determined as described in Example 29.

171. The derivative of any of embodiments 1-170, which has a potency corresponding to an $EC_{50}$ at 0% HSA of
a) below 60 pM, preferably below 40 pM, more preferably below 20 pM, even more preferably below 15 pM, still more preferably below 10 pM, or most preferably below 8.0 pM;
b) below 7.0 pM, preferably below 6.0 pM, more preferably below 5.0 pM, even more preferably below 4.0 pM, or most preferably below 3.0 pM; or
c) below 2.5 pM, preferably below 2.0 pM, more preferably below 1.5 pM, even more preferably below 1.2 pM, or most preferably below 1.0 pM.

172. The derivative of any of embodiments 1-171, which has a potency corresponding to an $EC_{50}$ at 1.0% HSA of
a) below 600 pM, preferably below 500 pM, more preferably below 450 pM, even more preferably below 400 pM, or most preferably below 300 pM;
b) below 270 pM, preferably below 250 pM, more preferably below 200 pM, even more preferably below 150 pM, still more preferably below 100 pM, or most preferably below 50 pM; or
c) below 40 pM, preferably below 35 pM, more preferably below 30 pM, even more preferably below 25 pM, or most preferably below 20 pM.

173. The derivative of any of embodiments 1-172, the in vitro potency $EC_{50}$ value of which, at 0% HSA is lower than 250% of that of semaglutide.

174. The derivative of any of embodiments 1-173, the in vitro potency $EC_{50}$ value of which, at 0% HSA is lower than 200% of that of semaglutide.

175. The derivative of any of embodiments 1-174, the in vitro potency $EC_{50}$ value of which, at 0% HSA and/or 1.0% HSA, is lower than that of semaglutide.

176. The derivative of any of embodiments 1-175, the in vitro potency $EC_{50}$ value of which, at 0% HSA and/or 1.0% HSA, is at or below 50% of the $EC_{50}$ value of semaglutide.

177. The derivative of any of embodiments 1-176, the in vitro potency $EC_{50}$ value of which, at 0% HSA and/or 1.0% HSA, is at or below 30% of the $EC_{50}$ value of semaglutide.

178. The derivative of any of embodiments 1-177, the in vitro potency $EC_{50}$ value of which, at 0% HSA and/or 1.0% HSA, is at or below 20% of the $EC_{50}$ value of semaglutide.

179. The derivative of any of embodiments 1-178, the in vitro potency $EC_{50}$ value of which, at 0% HSA and/or 1.0% HSA, is at or below 10% of the $EC_{50}$ value of semaglutide.

180. The derivative of any of embodiments 1-1179, which is capable of binding to the human GLP-1 receptor.

181. The derivative of embodiment 180, where the receptor binding activity is determined in vitro.

182. The derivative of any of embodiments 180-181, where the receptor binding is measured in a competitive binding assay, where a labelled ligand such as $^{125}$I-GLP-1 is bound to the receptor, the derivative is added in a desired series of concentrations, and displacement of the labelled ligand is monitored, preferably using a SPA binding assay.

183. The derivative of embodiment 182, where the receptor binding is reported as the concentration at which half of the labelled ligand is displaced from the receptor (the $IC_{50}$ value).

184. The derivative of any of embodiments 180-183, wherein activation of the human GLP-1 receptor is measured as GLP-1 receptor binding affinity ($IC_{50}$) in a very low concentration of serum albumin (max. 0.001% HSA, final assay concentration), and/or in a high concentration of serum albumin (2.0% HSA, final assay concentration).

185. The derivative of any of embodiments 180-185, wherein isolated membranes containing the human GLP-1 receptor are used.

186. The derivative of embodiment 185, wherein the membranes are prepared from cells expressing the human GLP-1 receptor.

187. The derivative of embodiment 186, wherein the cells are BHK cells.

188. The derivative of embodiment 187, wherein the BHK cells have BHKTS13 as a parent cell line.

189. The derivative of embodiment 188, wherein the cells are BHK cells of clone FCW467-12A.

190. The derivative of any of embodiments 180-189, wherein the GLP-1 receptor binding affinity ($IC_{50}$) is determined as described in Example 30.

191. The derivative of any of embodiments 1-190, for which the GLP-1 receptor binding affinity ($IC_{50}$) in the presence of low albumin (approximately 0.001% HSA, final assay concentration) is
a) below 6.0 nM, preferably below 3.0 nM, more preferably below 2.1 nM, still more preferably below 1.0 nM, even more preferably below 0.8 nM, or most preferably below 0.60 nM; or
b) below 0.50 nM, preferably below 0.40 nM, even more preferably below 0.30 nM, or most preferably below 0.20 nM.

192. The derivative of any of embodiments 1-191, for which the GLP-1 receptor binding affinity ($IC_{50}$) in the presence of high albumin (2.0% HSA, final assay concentration) is
a) below 1000 nM, preferably below 600 nM, more preferably below 500 nM, or most preferably below 300 nM;
b) below 200 nM, preferably below 100 nM, more preferably below 80 nM; or
c) below 70 nM, preferably below 40 nM, or more preferably below 30 nM.

193. The derivative of any of embodiments 1-192, the GLP-1 receptor binding affinity ($IC_{50}$) of which, in the presence of low albumin (approximately 0.001% HSA, final assay concentration) is lower than 350% of that of semaglutide.

194. The derivative of any of embodiments 1-193, the GLP-1 receptor binding affinity ($IC_{50}$) of which, in the presence of low albumin (approximately 0.001% HSA, final assay concentration) is lower than 200% of that of semaglutide.
195. The derivative of any of embodiments 1-194, the GLP-1 receptor binding affinity ($IC_{50}$) of which, in the presence of low albumin (approximately 0.001% HSA, final assay concentration) and/or in the presence of high albumin (2.0% HSA, final assay concentration), is lower than 150% of that of semaglutide.
196. The derivative of any of embodiments 1-195, the GLP-1 receptor binding affinity ($IC_{50}$) of which, in the presence of low albumin (approximately 0.001% HSA, final assay concentration) and/or in the presence of high albumin (2.0% HSA, final assay concentration), is lower than that of semaglutide.
197. The derivative of any of embodiments 1-196, the GLP-1 receptor binding affinity ($IC_{50}$) of which, in the presence of low albumin (approximately 0.001% HSA, final assay concentration) and/or in the presence of high albumin (2.0% HSA, final assay concentration), is lower than 75% of that of semaglutide.
198. The derivative of any of embodiments 1-197, the GLP-1 receptor binding affinity ($IC_{50}$) of which, in the presence of low albumin (approximately 0.001% HSA, final assay concentration) and/or in the presence of high albumin (2.0% HSA, final assay concentration), is lower than 50% of that of semaglutide.
199. The derivative of any of embodiments 1-198, the GLP-1 receptor binding affinity ($IC_{50}$) of which, in the presence of low albumin (approximately 0.001% HSA, final assay concentration) and/or in the presence of high albumin (2.0% HSA, final assay concentration), is lower than 35% of that of semaglutide.
200. The derivative of any of embodiments 1-199, the GLP-1 receptor binding affinity ($IC_{50}$) of which, in the presence of high albumin (2.0% HSA, final assay concentration), is lower than 25% of that of semaglutide.
201. The derivative of any of embodiments 1-200, the GLP-1 receptor binding affinity ($IC_{50}$) of which, in the presence of high albumin (2.0% HSA, final assay concentration), is lower than 10% of that of semaglutide.
202. The derivative of any of embodiments 1-201, the GLP-1 receptor binding affinity ($IC_{50}$) of which, in the presence of high albumin (2.0% HSA, final assay concentration), is lower than 5% of that of semaglutide.
203. The derivative of any of embodiments 1-202, which has a more protracted profile of action than liraglutide and/or semaglutide.
204. The derivative of embodiment 203, wherein protracted profile of action refers to terminal half-life in vivo in a relevant animal species, such as db/db mice, rat, pig, and dog, preferably mini pig and/or beagle dog; wherein the derivative is administered i) s.c., and/or, ii) i.v.; preferably ii) i.v.
205. The derivative of any of embodiments 1-204, wherein the terminal half-life (t½) after i.v. administration to mini pigs is
a) at least 55 hours, preferably at least 60 hours, more preferably at least 70 hours, even more preferably at least 80 hours, or most preferably at least 85 hours;
b) at least 90 hours, preferably at least 95 hours, more preferably at least 100 hours, even more preferably at least 105 hours, or most preferably at least 110 hours; or
c) at least 115 hours, preferably at least 120 hours, more preferably at least 125 hours, still more preferably at least 130 hours, even more preferably at least 135 hours, or most preferably at least 140 hours.
206. The derivative of any of embodiments 1-176, wherein the terminal half-life (t½) after i.v. administration to mini pigs is
a) at least on par with that of semaglutide;
b) at least 25% higher than that of semaglutide;
c) at least 50% higher than that of semaglutide;
d) at least 80% higher than that of semaglutide;
e) at least 100% higher than that of semaglutide; or
f) at least 150% higher than that of semaglutide.
207. The derivative of any of embodiments 204-206, wherein the mini pigs are female, preferably obtained from Ellegaard Göttingen Minipigs.
208. The derivative of any of embodiments 204-207, wherein the mini pigs are approximately 5 months of age, and preferably weighing approximately 10 kg.
209. The derivative of any of embodiments 204-208, wherein the mini pigs are housed in pens with straw as bedding, four to six together in each pen and fed once or twice daily, preferably with Altromin 9023 mini pig diet.
210. The derivative of any of embodiments 204-209, wherein the derivative is dosed, i.v., after an acclimatisation period of 1 week.
211. The derivative of any of embodiments 204-210, wherein the GLP-1 derivative is dissolved in 50 mM sodium phosphate, 70 mM sodium chloride, 0.05% tween 80, pH 7.4 to a suitable concentration, such as 20 nmol/ml.
212. The derivative of any of embodiments 204-211, wherein intravenous injections of the derivative are given in a volume corresponding to, e.g., 2 nmol/kg.
213. The derivative of any of embodiments 204-212, wherein the terminal half-life (t½) is determined in in vivo pharmacokinetic studies in mini pig, for example as described in Example 31.
214. The derivative of any of embodiments 1-213, wherein the terminal half-life (t½) after i.v. administration to Beagle dogs is
a) at least 56 hours, preferably at least 60 hours, more preferably at least 65 hours, even more preferably at least 70 hours, or most preferably at least 75 hours; or
b) at least 80 hours, preferably at least 85 hours, more preferably at least 90 hours, still more preferably at least 100 hours, even more preferably at least 105 hours, or most preferably at least 115 hours.
215. The derivative of any of embodiments 1-214, wherein the terminal half-life (t½) after i.v. administration to Beagle dogs is
a) at least on par with that of semaglutide;
b) at least 10% higher than that of semaglutide;
c) at least 25% higher than that of semaglutide;
d) at least 40% higher than that of semaglutide;
e) at least 60% higher than that of semaglutide;
f) at least 80% higher than that of semaglutide;
g) at least 100% higher than that of semaglutide; or
h) at least 110% higher than that of semaglutide.
216. The derivative of any of embodiments 214-215, wherein the Beagle dogs are housed in social groups (12 hours light: 12 hours dark), and fed individually and restrictedly once daily.
217. The derivative of any of embodiments 214-216, wherein the derivative is dosed, i.v., after an appropriate acclimatisation period.
218. The derivative of any of embodiments 214-217, wherein the GLP-1 derivative is dissolved in 50 mM sodium phosphate, 70 mM sodium chloride, 70 ppm Polysorbate 20, pH 7.4 to a suitable concentration, such as 20 nmol/ml.

219. The derivative of any of embodiments 214-218, wherein intravenous injections of the derivative are given in a volume corresponding to, e.g., 2 nmol/kg.

220. The derivative of any of embodiments 214-219, wherein the terminal half-life (t½) is determined in in vivo pharmacokinetic studies in Beagle dogs, for example as described in Example 32.

221. The derivative of any of embodiments 1-220, wherein the p.o bioavailability of the derivative, after oral administration in a tablet composition as described in Example 33 to Beagle dogs, is
a) at least 1.5%, preferably at least 2.0%, or more preferably at least 2.4%; or
b) at least 3.0%, more preferably at least 3.2%, or more preferably at least 3.4%.

222. The derivative of any of embodiments 1-221, wherein the p.o. bioavailability (F) of the derivative, after oral administration in a tablet composition as described in Example 33 to Beagle dogs, is
a) at least on par with that of semaglutide;
b) at least 10% higher than that of semaglutide;
c) at least 25% higher than that of semaglutide;
d) at least 50% higher than that of semaglutide;
e) at least 75% higher than that of semaglutide;
f) at least 100% higher than that of semaglutide;
g) at least 150% higher than that of semaglutide; or
h) at least 200% higher than that of semaglutide.

223. The derivative of any of embodiments 221-222, wherein the tablet comprises i) a tablet core, a Pharmacoat sub-coat, and an 80:20 FS30D:L30D-55 enteric coating, or ii) a tablet core, an Opadry Clear sub-coat, and an 80:20 FS30D:L30D-55 enteric coating; and wherein the tablet contains 10 mg of the derivative.

224. The derivative of any of embodiments 221-223, wherein the tablet has a final composition as shown in i) Table 6, or ii) Table 7.

225. The derivative of any of embodiments 221-224, wherein the p.o. bioavailability is the absolute bioavailability (F).

226. The derivative of embodiment 225, wherein F is calculated as $AUC/D_{po}$ divided by $AUC/D_{iv}$, where $D_{po}$ is the expected oral dose per kg of the derivative, calculated based on the amount dosed, and $D_{iv}$ is the dose per kg of the derivative which was given intravenously.

227. The derivative of embodiment 226, wherein AUC represents the area under the plasma concentration versus time curve (unit=time×concentration), which is calculated after both oral administration and intravenous administration.

228. The derivative of embodiment 227, wherein the AUC is calculated for the time period until 240-288 hours post dosing, or until last measured concentration.

229. The derivative of any of embodiments 221-227, wherein the Beagle dogs are housed in social groups (12 hours light: 12 hours dark), and fed individually and restrictedly once daily.

230. The derivative of any of embodiments 221-229, wherein the derivative is also dosed, i.v., after an appropriate acclimatisation period.

231. The derivative of embodiment 230, wherein the GLP-1 derivative is dissolved in 50 mM sodium phosphate, 70 mM sodium chloride, 70 ppm Polysorbate 20, pH 7.4 to a suitable concentration, such as 20 nmol/ml.

232. The derivative of any of embodiments 230-231, wherein intravenous injections of the derivative are given in a volume corresponding to, e.g., 2 nmol/kg.

233. The derivative of any of embodiments 221-232, wherein the tablets containing the GLP-1 derivative are administered in the following manner: Gastric acid secretion is induced by subcutaneous administration in the neck of pentagastrin at a dose of approximately 4 μg/kg body weight (120 μg/mL) 20 minutes prior to oral administration of the tablet; the tablet is placed in the back of the mouth of the dog in order to prevent chewing; the mouth is closed; and 10 mL of tap water is given by a syringe to facilitate swallowing of the tablet.

234. The derivative of any of embodiments 221-233, wherein the p.o. bioavailability is determined essentially as described in Example 32.

235. The derivative of any of embodiments 1-234, which in a pharmacodynamic (PD) study in pigs and when administered as a single dose s.c. has the effect of reducing food intake as compared to a vehicle-treated control group.

236. The derivative of embodiment 235, wherein the pigs are female Landrace Yorkshire Duroc (LYD) pigs or Large White hybrid, approximately 3 months of age, and weighing approximately 30-35 kg (preferably n=3-4 per group).

237. The derivative of any of embodiments 235-236, wherein the pigs are housed in a group for approximately 1 week during acclimatisation to the animal facilities, and subsequently, during the experimental period, the animals are placed in individual pens at least 2 days before dosing and during the entire experiment for measurement of individual food intake.

238. The derivative of any of embodiments 235-237, wherein the pigs are fed ad libitum at all times, or fodder is offered in the morning each day, and availability for the full 24-hour period is ensured.

239. The derivative of any of embodiments 235-238, wherein the derivatives are dissolved in a phosphate buffer (50 mM sodium phosphate, 70 mM sodium chloride, 0.05% tween 80, pH 7.4) at concentrations of approximately 120 nmol/ml corresponding to doses of 3 nmol/kg.

240. The derivative of embodiment 239, wherein the phosphate buffer serves as vehicle.

241. The derivative of any of embodiments 235-240, wherein the pigs are dosed with a single subcutaneous dose of the GLP-1 derivative or vehicle (dose volume 0.025 ml/kg) on the morning of day 1, and food intake is measured for 2-4 days after dosing.

242. The derivative of any of embodiments 235-241, wherein food intake is calculated in 24 h intervals (0-24 h, 24-48 h, 48-72 h and 72-96 h), and the mean food intake calculated as percentage of the mean food intake of the vehicle group in the same time interval.

243. The derivative of any of embodiments 235-242, wherein the food intake is determined essentially as described in Example 34.

244. The derivative of any of embodiments 235-243, wherein the food intake for hours 0-24, as compared to the vehicle group, is
a) no more than 80%, preferably no more than 70%, more preferably no more than 60%, even more preferably no more than 60%, or most preferably no more than 50%; or
b) no more than 50%, preferably no more than 40%, more preferably no more than 30%, even more preferably no more than 20%, or most preferably no more than 10%.

245. The derivative of any of embodiments 235-244, wherein the food intake for hours 24-48, as compared to the vehicle group, is a) no more than 70%, preferably no more than 60%, more preferably no more than 50%, even more preferably no more than 40%, or most preferably no more than 30%; or b) no more than 25%, or preferably no more than 20%.

246. The derivative of any of embodiments 235-245, wherein the food intake for hours 48-72, as compared to the vehicle group, is no more than 70%, preferably no more than 65%.

247. A GLP-1 peptide which comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and no other Lys residues, or a pharmaceutically acceptable salt, amide, or ester thereof.

248. The peptide of embodiment 247 which has a maximum of seven amino acid changes as compared to GLP-1(7-37) (SEQ ID NO: 1), preferably a maximum of six amino acid changes, more preferably a maximum of five amino acid changes.

249. The peptide of embodiment 248 wherein the maximum five, six, or seven amino acid changes include 36Lys and 37Lys.

250. The peptide of any of embodiments 247-249 which is a GLP-1(7-37) peptide.

251. The peptide of any of embodiments 247-249 which is a GLP-1(9-37) peptide.

252. The peptide of embodiment 251, wherein the amino acid residues at the positions corresponding to positions 7 and 8 of GLP-1(7-37) (SEQ ID NO: 1) have been deleted.

253. The peptide of any of embodiments 247-252, which comprises one or more of the following further amino acid changes: (8Aib or 8Gly), 22Glu, 26Arg, 30Glu, and/or (34Arg or 34Gln).

254. The peptide of any of embodiments 247-253, which comprises the following amino acid changes, as compared to GLP-1(7-37) (SEQ ID NO: 1): (i) 8Aib, 22Glu, 26Arg, 34Arg, 36Lys, and 37Lys; (ii) 8Aib, 26Arg, 34Arg, 36Lys, and 37Lys; (iii) 8Aib, 22Glu, 26Arg, 34Gln, 36Lys, and 37Lys; (iv) 8Gly, 22Glu, 26Arg, 34Arg, 36Lys, 37Lys; or (v) 8Aib, 22Glu, 26Arg, 30Glu, 34Arg, 36Lys, 37Lys.

255. The peptide of any of embodiments 247-254, which has the following amino acid changes, as compared to GLP-1 (7-37) (SEQ ID NO:1):
(i) 8Aib, 22Glu, 26Arg, 34Arg, 36Lys, and 37Lys; (ii) 8Aib, 26Arg, 34Arg, 36Lys, and 37Lys; (iii) 8Aib, 22Glu, 26Arg, 34Gln, 36Lys, and 37Lys; (iv) 8Gly, 22Glu, 26Arg, 34Arg, 36Lys, 37Lys; or (v) 8Aib, 22Glu, 26Arg, 30Glu, 34Arg, 36Lys, 37Lys.

260. The peptide of any of embodiments 247-259 which is SEQ ID NO: 2, SEQ ID NO: 3, SEQ ID NO: 4, SEQ ID NO: 5, or SEQ ID NO: 6.

261. The peptide of any of embodiments 247-260, wherein the comparison with GLP-1(7-37) (SEQ ID NO: 1) is made by handwriting and eyeballing.

262. The peptide of any of embodiments 247-261, wherein the comparison with GLP-1(7-37) (SEQ ID NO: 1) is made by use of a standard protein or peptide alignment program.

263. The peptide of embodiment 262, wherein the alignment program is a Needleman-Wunsch alignment.

264. The peptide of any of embodiments 262-263, wherein the default scoring matrix and the default identity matrix is used.

265. The peptide of any of embodiments 262-264, wherein the scoring matrix is BLOSUM62.

266. The peptide of any of embodiments 262-265, wherein the penalty for the first residue in a gap is −10 (minus ten).

267. The peptide of any of embodiments 262-266, wherein the penalties for additional residues in a gap is −0.5 (minus point five).

268. A GLP-1 peptide of Formula I:
Formula I: $Xaa_7$-$Xaa_8$-Glu-Gly-Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Lys_{36}$-$Lys_{37}$ (SEQ ID NO: 7), wherein $Xaa_7$ is L-histidine, (S)-2-Hydroxy-3-(1H-imidazol-4-yl)-propionic acid, D-histidine, desamino-histidine (desH), $N^\alpha$-acetyl-histidine, $N^\alpha$-formyl-histidine;

$Xaa_8$ is Ala, Gly, Ser, Aib, (1-aminocyclopropyl) carboxylic acid, (1-aminocyclobutyl) carboxylic acid;

$Xaa_{16}$ is Val or Leu;
$Xaa_{18}$ is Ser or Arg;
$Xaa_{19}$ is Tyr or Gln;
$Xaa_{20}$ is Leu or Met;
$Xaa_{22}$ is Gly or Glu;
$Xaa_{23}$ is Gln, Glu, or Arg;
$Xaa_{25}$ is Ala or Val;
$Xaa_{26}$ is Arg or Lys;
$Xaa_{27}$ is Glu or Leu;
$Xaa_{30}$ is Ala, or Glu;
$Xaa_{31}$ is Trp or His;
$Xaa_{33}$ is Val or Arg;
$Xaa_{34}$ is Arg, Lys, His, Asn, or Gln; and
$Xaa_{35}$ is Gly or Aib.

269. The GLP-1 peptide of embodiment 268, wherein $Xaa_7$ is His; $Xaa_8$ is Gly or Aib; $Xaa_{16}$ is Val; $Xaa_{18}$ is Ser; $Xaa_{19}$ is Tyr; $Xaa_{20}$ is Leu; $Xaa_{22}$ is Gly or Glu; $Xaa_{23}$ is Gln; $Xaa_{25}$ is Ala; $Xaa_{26}$ is Arg; $Xaa_{27}$ is Glu; $Xaa_{30}$ is Ala or Glu; $Xaa_{31}$ is Trp; $Xaa_{33}$ is Val; $Xaa_{34}$ is Arg or Gln; and $Xaa_{35}$ is Gly.

270. A GLP-1 peptide of Formula II:
Formula II: $Xaa_7$-$Xaa_8$-Glu-Gly-Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Lys_{36}$-$Lys_{37}$ (SEQ ID NO: 8), wherein $Xaa_7$ is L-histidine, (S)-2-Hydroxy-3-(1H-imidazol-4-yl)-propionic acid, D-histidine, desamino-histidine (desH), $N^\alpha$-acetyl-histidine, $N^\alpha$-formyl-histidine;

$Xaa_8$ is Ala, Ser, Aib, (1-aminocyclopropyl) carboxylic acid, (1-aminocyclobutyl) carboxylic acid;

$Xaa_{16}$ is Val or Leu;
$Xaa_{18}$ is Ser or Arg;
$Xaa_{19}$ is Tyr or Gln;
$Xaa_{20}$ is Leu or Met;
$Xaa_{22}$ is Gly or Glu;
$Xaa_{23}$ is Gln, Glu, or Arg;
$Xaa_{25}$ is Ala or Val;
$Xaa_{26}$ is Arg or Lys;
$Xaa_{27}$ is Glu or Leu;
$Xaa_{30}$ is Ala, or Glu;
$Xaa_{31}$ is Trp or His;
$Xaa_{33}$ is Val or Arg;
$Xaa_{34}$ is Arg, Lys, His, Asn, or Gln; and
$Xaa_{35}$ is Gly or Aib.

271. The GLP-1 peptide of embodiment 270, wherein $Xaa_7$ is His; $Xaa_8$ is Aib; $Xaa_{16}$ is Val; $Xaa_{18}$ is Ser; $Xaa_{19}$ is Tyr; $Xaa_{20}$ is Leu; $Xaa_{22}$ is Gly or Glu; $Xaa_{23}$ is Gln; $Xaa_{25}$ is Ala; $Xaa_{26}$ is Arg; $Xaa_{27}$ is Glu; $Xaa_{30}$ is Ala or Glu; $Xaa_{31}$ is Trp; $Xaa_{33}$ is Val; $Xaa_{34}$ is Arg or Gln; and $Xaa_{35}$ is Gly.

272. A GLP-1 (9-37) peptide which is a peptide as defined in any of embodiments 268-271, except that $Xaa_7$ and $Xaa_8$ are absent.

273. The peptide of any of embodiments 247-272 which is an analogue of GLP-1(7-37) (SEQ ID NO: 1).

274. The peptide of any of embodiments 247-273 which has GLP-1 activity.

275. The peptide of embodiment 274, wherein the GLP-1 activity may be determined in any appropriate way, e.g. as described in any of embodiments 149-202.

276. An intermediate product comprising, or consisting of, a side chain moiety of Chem. 6:

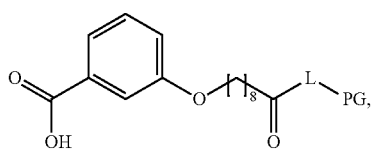
Chem. 6 wherein L is an optional linker being a di-radical incorporating an *—NH group and a *—CO group (the *—NH group is at the left hand end of the molecule, and the *—CO group at the right hand end of the molecule), PG is a protection group; and the distal COOH group (in meta position on the aromatic ring) and/or any other COOH-group if present, is optionally also protected;

or a pharmaceutically acceptable salt, amide or ester thereof.

277. The intermediate product of embodiment 276, wherein (when L is absent) CO-PG is, or (when L is present) L-PG includes a distal i) COOH group, or ii) activated ester.

278. The intermediate product of embodiment 277, wherein the activated ester is an ester of p-nitrophenol; 2,4,5-trichlorophenol; N-hydroxysuccinimide; N-hydroxysulfosuccinimide; 3,4-dihydro-3-hydroxy-1,2,3-benzotriazine-4-one; 5-chloro-8-hydroxyquinoline; N-hydroxy-5-norbornene-2,3-dicarboxylic acid imide; pentafluorophenol; p-sulfotetrafluorophenol; N-hydroxyphthalimide; 1-hydroxybenzotriazole; 1-hydroxy-7-azabenzotriazole; N-hydroxymaleimide; 4-hydroxy-3-nitrobenzene sulfonic acid; or any other activated ester known in the art.

279. The intermediate product of embodiment 278, wherein the activated ester is N-hydroxysuccinimide.

280. The intermediate product of any of embodiments 276-279, wherein the linker is absent.

281. The intermediate product of any of embodiments 276-279, wherein the linker comprises at least one of Chem. 3a, Chem. 4a, and Chem. 5a:

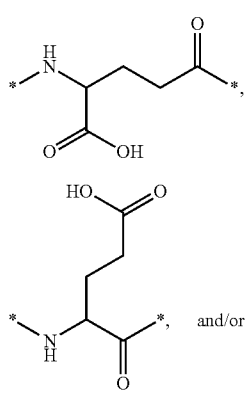

Chem. 3a

Chem. 4a and/or

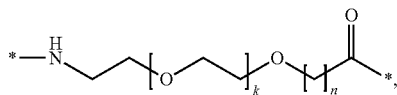
Chem. 5a wherein k is an integer in the range of 1-5, and n is an integer in the range of 1-5.

282. The intermediate product of any of embodiments 276-281, wherein the linker is as defined in any of embodiments 12-62.

283. The intermediate product of any of embodiments 276-282, wherein, optionally, the distal COOH group of Chem. 6, and/or the one or more additional COOH-groups, if present in the linker part (L) of Chem. 6, is/are also protected as is known in the art.

284. The intermediate product of any of embodiments 276-283, wherein, optionally, the distal COOH group of Chem. 6 and/or the one or more additional COOH-groups, if present in the linker part (L) of Chem. 6, is/are also protected by formation of a non-reactive ester.

285. The intermediate product of embodiment 284, wherein the non-reactive ester is i) an ester of an alcohol with a bulky side chain such as an aromatic group, or ii) an ester of an alcohol of branched alkyl, preferably lower branched alkyl.

286. The intermediate product of embodiment 284, wherein the non-reactive ester is a tert. butyl ester (OtBu), a benzoyl ester (OBz), or the like.

287. The intermediate product of embodiment 285, wherein the alcohol with a bulky aromatic group is benzyl alcohol.

288. The intermediate product of embodiment 285, wherein the alcohol of lower branched alkyl is tert. butyl alcohol.

289. An intermediate product, preferably according to any of embodiments 276-288, which is Chem. 7:

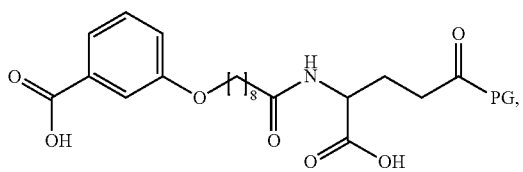
Chem. 7 wherein i) none of the COOH groups, ii) the distal COOH group only, iii) the non-distal COOH group only, or iv) both COOH groups is/are protected as described in any of embodiments 284-288;

or a pharmaceutically acceptable salt, amide, or ester thereof.

290. The intermediate product of embodiment 289, wherein none of the COOH groups is protected.

291. The intermediate product of embodiment 289, wherein each of the two COOH groups is protected as a tert. butyl ester.

292. The intermediate product of embodiment 289, wherein each of the two COOH groups is protected as a benzoyl ester.

293. An intermediate product, preferably according to any of embodiments 276-288, which is Chem. 8:

Chem. 8

[Chemical structure diagram showing a compound with a hydroxybenzoic acid group connected via an alkyl chain to an amide, glutamic acid residue, and PEG-like linker ending in PG]

wherein
i) none of the COOH groups, ii) the distal COOH group only, iii) the non-distal COOH group only, or iv) both COOH groups is/are protected as described in any of embodiments 284-288;
or a pharmaceutically acceptable salt, amide, or ester thereof.
294. The intermediate product of embodiment 293, wherein none of the COOH groups is protected.
295. The intermediate product of embodiment 293, wherein each of the two COOH groups is protected as a tert. butyl ester.
296. The intermediate product of embodiment 293, wherein each of the two COOH groups is protected as a benzoyl ester.
297. A derivative according to any of embodiments 1-246, or a peptide according to any of embodiments 247-275, for use as a medicament.
298. A derivative according to any of embodiments 1-246, or a peptide according to any of embodiments 247-275, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
299. Use of a derivative according to any of embodiments 1-246, or a peptide according to any of embodiments 247-275, in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
300. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments 1-246, or a peptide according to any of embodiments 247-275.

The invention also relates to a derivative of a GLP-1 peptide, which peptide comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and a maximum of seven amino acid changes as compared to GLP-1(7-37) (SEQ ID NO: 1), which derivative comprises a first and a second protractor attached to said first and second Lys residue, respectively, via a first and a second linker, respectively, wherein the first and the second protractor are selected from:

$$HOOC-C_6H_4-O-(CH_2)_y-CO-*, \text{ and} \qquad \text{Chem. 1:}$$

$$HOOC-(CH_2)_x-CO-*, \qquad \text{Chem. 2:}$$

wherein y is an integer in the range of 8-11, and x is 12; and the first and the second linker comprises at least one of:

$$*-NH-CH(COOH)-(CH_2)_2-CO-*, \qquad \text{Chem. 3:}$$

$$*-NH-CH((CH_2)_2-COOH)-CO-*, \text{ and/or} \qquad \text{Chem. 4:}$$

$$*-NH-(CH_2)_2-[O-(CH_2)_2]_k-O-[CH_2]_n-CO-*, \qquad \text{Chem. 5:}$$

wherein k is an integer in the range of 1-5, and n is an integer in the range of 1-5; or a pharmaceutically acceptable salt, amide, or ester thereof;
as well as any of the above embodiments 2-246 appended hereto as dependent embodiments, mutatis mutandis and/or by analogy.

The following are further particular embodiments of the invention:
1. A derivative of a GLP-1 peptide,
which peptide comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and a maximum of seven amino acid changes as compared to GLP-1(7-37) (SEQ ID NO: 1);
which derivative comprises two protractors attached to said first and second Lys residue, respectively, each via a linker;
wherein
the protractor is selected from:

$$HOOC-C_6H_4-O-(CH_2)_y-CO-*, \text{ and} \qquad \text{Chem. 1:}$$

$$HOOC-(CH_2)_x-CO-*, \qquad \text{Chem. 2:}$$

wherein y is an integer in the range of 9-11, and x is 12; and
the linker comprises at least one of:

$$*-NH-CH(COOH)-(CH_2)_2-CO-*, \qquad \text{Chem. 3:}$$

$$*-NH-CH((CH_2)_2-COOH)-CO-*, \text{ and/or} \qquad \text{Chem. 4:}$$

$$*-NH-(CH_2)_2-[O-(CH_2)_2]_k-O-[CH_2]_n-CO-*, \qquad \text{Chem. 5:}$$

wherein k is an integer in the range of 1-5, and n is an integer in the range of 1-5;
or a pharmaceutically acceptable salt, amide, or ester thereof.
2. The derivative of claim 1, wherein the protractor is Chem. 1.
3. The derivative of any of claims 1-2, wherein the protractor is selected from:

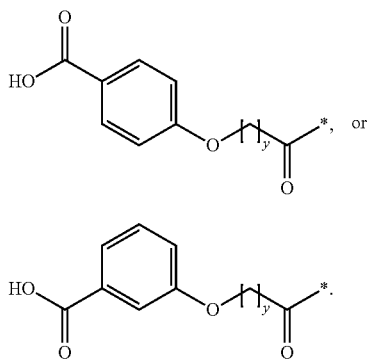

Chem. 1a

Chem. 1b

4. The derivative of any of claims 1-3, wherein the protractor is Chem. 1a:

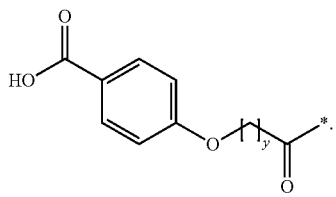

5. The derivative of any of claims 1-3, wherein the protractor is Chem. 1b:

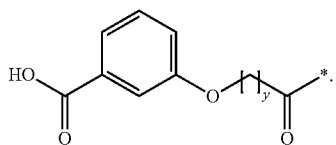

6. The derivative of any of claims 1-5, wherein y is 9, 10, or 11.
7. The derivative of any of claims 1-6, wherein y is 9.
8. The derivative of any of claims 1-6, wherein y is 10.
9. The derivative of any of claims 1-6, wherein y is 11.
10. The derivative of claim 1, wherein the protractor is Chem. 2.
11. The derivative of any of claims 1-10, wherein the linker comprises Chem. 5.
12. The derivative of any of claims 1-11, wherein the linker comprises Chem. 5a:

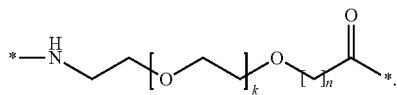

13. The derivative of any of claims 1-12, wherein k=n=1.
14. The derivative of any of claims 1-13, wherein the linker comprises

*—NH—(CH$_2$)$_2$—O—(CH$_2$)$_2$—O—CH$_2$—CO—*.  Chem. 5b:

15. The derivative of any of claims 1-14, wherein Chem. 5 is included one, two, or three times.

16. The derivative of any of claims 1-15, wherein Chem. 5 is included one time.
17. The derivative of any of claims 1-15, wherein Chem. 5 is included two times.
18. The derivative of any of claims 1-15, wherein Chem. 5 is included three times.
19. The derivative of any of claims 1-15, wherein Chem. 5a is included one, two, or three times.
20. The derivative of any of claims 1-15, wherein Chem. 5a is included one time.
21. The derivative of any of claims 1-15, wherein Chem. 5a is included two times.
22. The derivative of any of claims 1-15, wherein Chem. 5a is included three times.
23. The derivative of any of claims 1-15, wherein Chem. 5b is included one, two, or three times.
24. The derivative of any of claims 1-15, wherein Chem. 5b is included one time.
25. The derivative of any of claims 1-15, wherein Chem. 5b is included two times.
26. The derivative of any of claims 1-15, wherein Chem. 5b is included three times.
27. The derivative of any of claims 1-26, wherein the linker comprises Chem. 3.
28. The derivative of any of claims 1-27, wherein the linker comprises Chem. 3a:

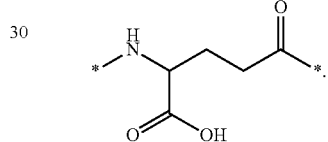

29. The derivative of any of claims 1-28, wherein Chem. 3 is not included, included one time, or included two times.
30. The derivative of any of claims 1-29, wherein Chem. 3 is not included.
31. The derivative of any of claims 1-29, wherein Chem. 3 is included one time.
32. The derivative of any of claims 1-29, wherein Chem. 3 is included two times.
33. The derivative of any of claims 1-29, wherein Chem. 3a is not included, included one time, or included two times.
34. The derivative of any of claims 1-29, wherein Chem. 3a is not included.
35. The derivative of any of claims 1-29, wherein Chem. 3a is included one time.
36. The derivative of any of claims 1-29, wherein Chem. 3a is included two times.
37. The derivative of any of claims 1-36, wherein the linker comprises Chem. 4.
38. The derivative of any of claims 1-37, wherein the linker comprises Chem. 4a:

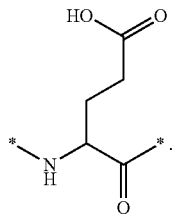 [SMILES: *NC(CCC(=O)O)C(*)=O]

39. The derivative of any of claims 1-38, wherein Chem. 4 is not included, or included two times.
40. The derivative of any of claims 1-39, wherein Chem. 4 is not included.
41. The derivative of any of claims 1-39, wherein Chem. 4 is included two times.
42. The derivative of any of claims 1-39, wherein Chem. 4a is not included, or included two times.
43. The derivative of any of claims 1-39, wherein Chem. 4a is not included.
44. The derivative of any of claims 1-39, wherein Chem. 4a is included two times.
45. The derivative of any of claims 1-44, wherein the linker consists of two Chem. 3 elements, and two Chem. 5b elements (2×Chem. 3-2×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.
46. The derivative of any of claims 1-44, wherein the linker consists of two Chem. 3a elements, and two Chem. 5a elements where n=k=1 (2×Chem. 3a-2×Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.
47. The derivative of any of claims 1-44, wherein the linker consists of one Chem. 3 element, and two Chem. 5b elements (Chem. 3-2×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.
48. The derivative of any of claims 1-44, wherein the linker consists of one Chem. 3a element, and two Chem. 5a elements where n=k=1 (Chem. 3a-2×Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.
49. The derivative of any of claims 1-44, wherein the linker consists of one Chem. 3 element, and three Chem. 5b elements (Chem. 3-3×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.
50. The derivative of any of claims 1-44, wherein the linker consists of one Chem. 3a element, and three Chem. 5a elements where n=k=1 (Chem. 3a-3×Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.
51. The derivative of any of claims 1-44, wherein the linker consists of two Chem. 4 elements, and one Chem. 5b element (2×Chem. 4-Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.
52. The derivative of any of claims 1-44, wherein the linker consists of two Chem. 4a elements, and one Chem. 5a element where n=k=1 (2×Chem. 4a-Chem. 5a), interconnected via amide bonds and in the sequence indicated, connected at its *—NH end to the CO—* end of the protractor, and at its CO—* end to the epsilon amino group of the first or the second Lys residue of the GLP-1 peptide.
53. The derivative of any of embodiments 1-52, wherein the linker and the protractor are interconnected via an amide bond.
54. The derivative of any of embodiments 1-53, wherein the linker and the GLP-1 peptide are interconnected via an amide bond.
55. The derivative of any of embodiments 1-54, wherein the CO—* end of the linker forms an amide bond with the epsilon-amino group of the first or the second Lys residue.
56. The derivative of any of embodiments 1-55, wherein the two protractors are substantially identical, preferably identical.
57. The derivative of any of embodiments 1-56, wherein the two protractors have a similarity of at least 0.5; preferably at least 0.6; more preferably at least 0.7, or at least 0.8; even more preferably at least 0.9; or most preferably at least 0.99, such as a similarity of 1.0.
58. The derivative of any of embodiments 1-57, wherein the two linkers are substantially identical, preferably identical.
59. The derivative of any of embodiments 1-58, wherein the two linkers have a similarity of at least 0.5; preferably at least 0.6; more preferably at least 0.7, or at least 0.8; even more preferably at least 0.9; or most preferably at least 0.99, such as a similarity of 1.0.
60. The derivative of any of embodiments 1-59, wherein the two side chains consisting of protractor and linker are substantially identical, preferably identical.
61. The derivative of any of embodiments 1-60, wherein the two side chains consisting of protractor and linker have a similarity of at least 0.5; preferably at least 0.6; more preferably at least 0.7, or at least 0.8; even more preferably at least 0.9; or most preferably at least 0.99, such as a similarity of 1.0.
62. The derivative of any of embodiments 56-61, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity of the two fingerprints.
63. The derivative of any of embodiments 1-62, wherein the first Lys residue is designated 36Lys.
64. The derivative of any of embodiments 1-63, wherein the second Lys residue is designated 37Lys.
65. The derivative of any of embodiments 1-64 wherein the position corresponding to position 36 of GLP-1(7-37) (SEQ ID NO: 1) is identified by handwriting and eyeballing.
66. The derivative of any of embodiments 1-65, wherein the position corresponding to position 37 of GLP-1(7-37) (SEQ ID NO: 1) is identified by handwriting and eyeballing.
67. The derivative of any of embodiments 1-66, wherein the total number of amino acid changes as compared to GLP-1(7-37) (SEQ ID NO: 1) are identified by handwriting and eyeballing.
68. The derivative of any of embodiments 1-67, wherein the two amino acid changes of 36Lys and 37Lys are included when counting the number of amino acid changes as compared to GLP-1(7-37) (SEQ ID NO: 1).
69. The derivative of any of embodiments 1-68, wherein the position corresponding to position 36 of GLP-1(7-37) (SEQ ID NO: 1) is identified by use of a standard protein or peptide alignment program.
70. The derivative of any of embodiments 1-69, wherein the position corresponding to position 37 of GLP-1(7-37) (SEQ ID NO: 1) is identified by use of a standard protein or peptide alignment program.

71. The derivative of any of embodiments 1-70, wherein the number of amino acid changes as compared to GLP-1(7-37) (SEQ ID NO: 1) are identified by use of a standard protein or peptide alignment program.
72. The derivative of any of embodiments 69-71, wherein the alignment program is a Needleman-Wunsch alignment.
73. The derivative of any of embodiments 69-72, wherein the default scoring matrix and the default identity matrix is used.
74. The derivative of any of embodiments 69-73, wherein the scoring matrix is BLOSUM62.
75. The derivative of any of embodiments 69-74, wherein the penalty for the first residue in a gap is −10 (minus ten).
76. The derivative of any of embodiments 69-75, wherein the penalties for additional residues in a gap is −0.5 (minus point five).
77. The derivative of any of embodiments 1-76, wherein the GLP-1 peptide is an analogue of GLP-1(7-37) (SEQ ID NO: 1) that comprises at least the substitutions R36K and G37K.
78. The derivative of any of embodiments 1-77, wherein the GLP-1 peptide comprises no Lys residues other than 36Lys and 37Lys.
79. The derivative of any of embodiments 1-78, wherein the GLP-1 peptide has a maximum of five amino acid changes as compared to GLP-1(7-37) (SEQ ID NO: 1).
80. The derivative of any of embodiments 1-78, wherein the GLP-1 peptide has a maximum of six amino acid changes as compared to GLP-1(7-37) (SEQ ID NO: 1).
81. The derivative of any of embodiments 1-78, wherein the GLP-1 peptide has a minimum of five amino acid changes as compared to GLP-1(7-37) (SEQ ID NO: 1).
82. The derivative of any of embodiments 1-78, wherein the GLP-1 peptide has a minimum of six amino acid changes as compared to GLP-1(7-37) (SEQ ID NO: 1).
83. The derivative of any of embodiments 1-78, wherein the GLP-1 peptide has five or six amino acid changes as compared to GLP-1(7-37) (SEQ ID NO: 1).
84. The derivative of any of embodiments 1-78, wherein the GLP-1 peptide has five amino acid changes as compared to GLP-1(7-37) (SEQ ID NO: 1).
85. The derivative of any of embodiments 1-78, wherein the GLP-1 peptide has six amino acid changes as compared to GLP-1(7-37) (SEQ ID NO: 1).
86. The derivative of any of embodiments 1-85, wherein the amino acid changes are at one or more positions corresponding to one or more of positions 8, 22, 26, 34, 36, and 37 of GLP-1(7-37) (SEQ ID NO: 1).
87. The derivative of any of embodiments 1-86, wherein the peptide comprises 36Lys and 37Lys, and optionally one or more of the following further amino acid changes: 8Aib, 22Glu, 26Arg, and/or (34Arg or 34Gln).
88. The derivative of any of embodiments 1-87, wherein the peptide comprises 8Aib.
89. The derivative of any of embodiments 1-88, wherein the peptide comprises 22Glu.
90. The derivative of any of embodiments 1-89, wherein the peptide comprises 26Arg.
91. The derivative of any of embodiments 1-90, wherein the peptide comprises 34Arg.
92. The derivative of any of embodiments 1-90, wherein the peptide comprises 34Gln.
93. The derivative of any of embodiments 1-92, wherein, for determination of the changes in the peptide, the amino acid sequence of the peptide is compared to the amino acid sequence of native GLP-1(7-37) (SEQ ID NO: 1).
94. The derivative of any of embodiments 1-93, wherein, for determination of a position in a peptide which corresponds to a specified position in native GLP-1(7-37) (SEQ ID NO: 1), the amino acid sequence of the peptide is compared to the amino acid sequence of native GLP-1(7-37) (SEQ ID NO: 1).
95. The derivative of any of embodiments 1-94, wherein the comparison of the amino acid sequence of the peptide with that of GLP-1(7-37) (SEQ ID NO: 1) is done by handwriting and eyeballing.
96. The derivative of any of embodiments 1-95, wherein the comparison of the amino acid sequence of the peptide with that of GLP-1(7-37) (SEQ ID NO: 1) is done by use of a standard protein or peptide alignment program.
97. The derivative of embodiment 96, wherein the alignment program is a Needleman-Wunsch alignment.
98. The derivative of any of embodiments 96-97, wherein the default scoring matrix and the default identity matrix is used.
99. The derivative of any of embodiments 96-98, wherein the scoring matrix is BLOSUM62.
100. The derivative of any of embodiments 96-99, wherein the penalty for the first residue in a gap is −10 (minus ten).
101. The derivative of any of embodiments 96-100, wherein the penalties for additional residues in a gap is −0.5 (minus point five).
102. The derivative of any of embodiments 1-101, wherein the position corresponding to any of the indicated positions of GLP-1(7-37) (SEQ ID NO: 1) is identified by handwriting and eyeballing.
103. The derivative of any of embodiments 1-102, wherein the position corresponding to any of the indicated positions of GLP-1(7-37) (SEQ ID NO: 1) is identified as described for position 36 and position 37 in any of embodiments 69-76.
104. The derivative of any of embodiments 1-103, wherein the GLP-1 peptide a) comprises a GLP-1 compound of Formula I; and/or b) is a GLP-1 compound of Formula I:

Formula I: $Xaa_7$-$Xaa_8$-Glu-Gly-Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Lys_{36}$-$Lys_{37}$ (SEQ ID NO: 7), wherein $Xaa_7$ is L-histidine, (S)-2-Hydroxy-3-(1H-imidazol-4-yl)-propionic acid, D-histidine, desamino-histidine (desH), $N^\alpha$-acetyl-histidine, $N^\alpha$-formyl-histidine;

$Xaa_8$ is Ala, Gly, Ser, Aib, (1-aminocyclopropyl) carboxylic acid, (1-aminocyclobutyl) carboxylic acid;

$Xaa_{16}$ is Val or Leu;
$Xaa_{18}$ is Ser or Arg;
$Xaa_{19}$ is Tyr or Gln;
$Xaa_{20}$ is Leu or Met;
$Xaa_{22}$ is Gly or Glu;
$Xaa_{23}$ is Gln, Glu, or Arg;
$Xaa_{25}$ is Ala or Val;
$Xaa_{26}$ is Arg or Lys;
$Xaa_{27}$ is Glu or Leu;
$Xaa_{30}$ is Ala, or Glu;
$Xaa_{31}$ is Trp or His;
$Xaa_{33}$ is Val or Arg;
$Xaa_{34}$ is Arg, Lys, His, Asn, or Gln; and
$Xaa_{35}$ is Gly or Aib.

105. The derivative of embodiment 104, wherein the GLP-1 compound of Formula I is an analogue of GLP-1(7-37) (SEQ ID NO: 1).
106. The derivative of any of embodiments 104-105, wherein $Xaa_7$ is His; $Xaa_8$ is Aib; $Xaa_{16}$ is Val; $Xaa_{18}$ is Ser; $Xaa_{19}$ is Tyr; $Xaa_{20}$ is Leu; $Xaa_{22}$ is Gly or Glu; $Xaa_{23}$ is Gln; $Xaa_{25}$ is Ala; $Xaa_{26}$ is Arg; $Xaa_{27}$ is Glu; $Xaa_{30}$ is Ala; $Xaa_{31}$ is Trp; $Xaa_{33}$ is Val; $Xaa_{34}$ is Arg or Gln; and $Xaa_{35}$ is Gly.

107. The derivative of any of embodiments 104-106, wherein $Xaa_7$ is His.
108. The derivative of any of embodiments 104-107, wherein $Xaa_8$ is Aib.
109. The derivative of any of embodiments 104-108, wherein $Xaa_{12}$ is Phe.
110. The derivative of any of embodiments 104-109, wherein $Xaa_{16}$ is Val.
111. The derivative of any of embodiments 104-110, wherein $Xaa_{18}$ is Ser.
112. The derivative of any of embodiments 104-111, wherein $Xaa_{19}$ is Tyr.
113. The derivative of any of embodiments 104-112, wherein $Xaa_{20}$ is Leu.
114. The derivative of any of embodiments 104-113, wherein $Xaa_{22}$ is Gly.
115. The derivative of any of embodiments 104-113, wherein $Xaa_{22}$ is Glu.
116. The derivative of any of embodiments 104-115, wherein $Xaa_{23}$ is Gln.
117. The derivative of any of embodiments 104-116, wherein $Xaa_{25}$ is Ala.
118. The derivative of any of embodiments 104-117, wherein $Xaa_{26}$ is Arg.
119. The derivative of any of embodiments 104-118, wherein $Xaa_{27}$ is Glu.
120. The derivative of any of embodiments 104-119, wherein $Xaa_{30}$ is Ala.
121. The derivative of any of embodiments 104-120, wherein $Xaa_{31}$ is Trp.
122. The derivative of any of embodiments 104-121, wherein $Xaa_{33}$ is Val.
123. The derivative of any of embodiments 104-122, wherein $Xaa_{34}$ is Arg.
124. The derivative of any of embodiments 104-122, wherein $Xaa_{34}$ is Gln.
125. The derivative of any of embodiments 104-124, wherein $Xaa_{35}$ is Gly.
126. The derivative of any of embodiments 1-125, wherein the peptide comprises the following amino acid changes, as compared to GLP-1(7-37) (SEQ ID NO: 1): (i) 8Aib, 22Glu, 26Arg, 34Arg, 36Lys, and 37Lys; (ii) 8Aib, 26Arg, 34Arg, 36Lys, and 37Lys; or (iii) 8Aib, 22Glu, 26Arg, 34Gln, 36Lys, and 37Lys.
127. The derivative of any of embodiments 1-126, wherein the peptide has the following amino acid changes, as compared to GLP-1(7-37) (SEQ ID NO:1): (i) 8Aib, 22Glu, 26Arg, 34Arg, 36Lys, and 37Lys; (ii) 8Aib, 26Arg, 34Arg, 36Lys, and 37Lys; or (iii) 8Aib, 22Glu, 26Arg, 34Gln, 36Lys, and 37Lys.
128. The derivative of any of embodiments 1-127, wherein the peptide is SEQ ID NO: 2, SEQ ID NO: 3, or SEQ ID NO: 4.
129. A compound, preferably a GLP-1 derivative according to any of embodiments 1-128, selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, and Chem. 36; or a pharmaceutically acceptable salt, amide, or ester thereof.
130. A compound, preferably a compound of embodiment 129, characterised by its name, and selected from a listing of each of the names of the compounds of Examples 1-16 herein; or a pharmaceutically acceptable salt, amide, or ester thereof.
131. The derivative of any of embodiments 1-130, which has GLP-1 activity.
132. The derivative of embodiment 131, wherein GLP-1 activity refers to the capability of activating the human GLP-1 receptor.
133. The derivative of embodiment 132, wherein activation of the human GLP-1 receptor is measured in an in vitro assay, as the potency of cAMP production.
134. The derivative of any of embodiments 131-132, wherein activation of the human GLP-1 receptor is measured in an in vitro assay, in a reporter gene assay.
135. The derivative of any of embodiments 131-134, wherein the assay is performed in a stably transfected BHK cell line that expresses the human GLP-1 receptor and contains the DNA for the cAMP response element (CRE) coupled to a promoter and the gene for firefly luciferase (CRE luciferase).
136. The derivative of embodiment 135, wherein when assay incubation is completed luciferin is added and luminescence is measured.
137. The derivative of any of embodiments 131-136, wherein the assay is performed in the absence of serum albumin (0% HSA, final assay concentration).
138. The derivative of any of embodiments 131-137, wherein the assay is performed in the presence of serum albumin (1.0% HSA, final assay concentration).
139. The derivative of any of embodiments 131-138, wherein the cells are BHK cells with BHKTS13 as a parent cell line.
140. The derivative of any of embodiments 131-139, wherein the cells are derived from clone FCW467-12A.
141. The derivative of any of embodiments 131-140, wherein the cells are cultured at 5% $CO_2$ in Cell Culture Medium, aliquoted and stored in liquid nitrogen.
142. The derivative of embodiment 141, wherein the Cell Culture Medium is 10% FBS (Fetal Bovine Serum), 1 mg/ml G418, 240 nM MTX (methotrexate) and 1% pen/strep (penicillin/streptomycin).
143. The derivative of any of embodiments 131-142, wherein before each assay a cell culture aliquot is taken up and washed twice in PBS before being suspended at the desired concentration in the assay specific buffer.
144. The derivative of any of embodiments 131-143, wherein for 96-well plates the suspension is made to give a final concentration of $5 \times 10^3$ cells/well.
145. The derivative of any of embodiments 143-144, wherein the assay specific buffer is 1% Assay Buffer, which consists of 2% ovalbumin, 0.2% Pluronic F-68 and 2% HSA in Assay Medium.
146. The derivative of any of embodiments 143-144, wherein the Assay Buffer is 0% Assay Buffer, which consists of 2% ovalbumin and 0.2% Pluronic F-68 in Assay Medium.
147. The derivative of any of embodiments 145-146, wherein Assay Medium consists of DMEM w/o phenol red, 10 mM Hepes and 1× Glutamax.
148. The derivative of any of embodiments 131-147, wherein the assay procedure comprises the following steps:
i) Cell stocks are thawed in a 37° C. water bath;
ii) cells are washed three times in PBS;
iii) the cells are counted and adjusted to $5 \times 10^3$ cells/50 µl ($1 \times 10^5$ cells/ml) in Assay Medium, and a 50 µl aliquot of cells is transferred to each well in the assay plate;
iv) stocks of the test compounds and reference compounds, if any, are diluted to a concentration of 0.2 pM in 0% Assay Buffer for the 0% HSA assay or 1% Assay Buffer for the 1% HSA assay; and compounds are diluted 10-fold to give a suitable range of concentrations (such as: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M, $2 \times 10^{-13}$ M, and 2×10$^{-14}$ M), and for each compound a blank assay buffer control is also included;

v) a 50 μl aliquot of compound or blank is transferred in triplicate from the dilution plate to the assay plate, and compounds are tested at suitable concentrations (such as the following final concentrations: 1×10$^{-7}$ M, 1×10$^{-8}$ M; 1×10$^{-9}$ M, 1×10$^{-10}$ M, 1×10$^{-11}$ M, 1×10$^{-12}$ M, 1×10$^{-13}$ M, and 1×10$^{-14}$ M);

vi) the assay plate is incubated for 3 h in a 5% CO$_2$ incubator at 37° C.;

vii) the assay plate is removed from the incubator and allowed to stand at room temperature for 15 min;

ixx) a 100 μl aliquot of luciferin (such as steadylite plus reagent) is added to each well of the assay plate;

ix) each assay plate is covered to protect it from light and shaken for 30 min at room temperature; and x) each assay plate is read, for example in a Packard TopCount NXT instrument.

149. The derivative of embodiment 148, wherein the data e.g. from the TopCount instrument are transferred to suitable software such as GraphPad Prism 5 for desired calculations.

150. The derivative of any of embodiments 131-149, wherein values for each triplicate is averaged, a non-linear regression performed, and the EC$_{50}$ values calculated.

151. The derivative of any of embodiments 149-150, wherein the regression is log(agonist) vs response.

152. The derivative of any of embodiments 131-133, wherein the potency is determined as described in any of embodiments 134-151.

153. The derivative of any of embodiments 131-152, wherein the potency is determined as described in Example 29.

154. The derivative of any of embodiments 1-153, which has a potency corresponding to an EC$_{50}$ at 0% HSA of
a) below 60 pM, preferably below 40 pM, more preferably below 20 pM, even more preferably below 10 pM, or most preferably below 8.0 pM;
b) below 7.0 pM, preferably below 6.0 pM, more preferably below 5.0 pM, even more preferably below 4.0 pM, or most preferably below 3.0 pM; or
c) below 2.5 pM, preferably below 2.0 pM, more preferably below 1.5 pM, even more preferably below 1.2 pM, or most preferably below 1.0 pM.

155. The derivative of any of embodiments 1-153, which has a potency corresponding to an EC$_{50}$ at 1.0% HSA of
a) below 600 pM, preferably below 500 pM, more preferably below 450 pM, even more preferably below 400 pM, or most preferably below 300 pM;
b) below 270 pM, preferably below 200 pM, more preferably below 250 pM, even more preferably below 100 pM, or most preferably below 50 pM; or
c) below 40 pM, preferably below 35 pM, more preferably below 30 pM, even more preferably below 25 pM, or most preferably below 20 pM.

156. The derivative of any of embodiments 1-155, the in vitro potency EC$_{50}$ value of which, at 0% HSA and/or 1.0% HSA, is lower than that of semaglutide.

157. The derivative of any of embodiments 1-156, the in vitro potency EC$_{50}$ value of which, at 0% HSA and/or 1.0% HSA, is at or below 50% of the EC$_{50}$ value of semaglutide.

158. The derivative of any of embodiments 1-157, the in vitro potency EC$_{50}$ value of which, at 0% HSA and/or 1.0% HSA, is at or below 30% of the EC$_{50}$ value of semaglutide.

159. The derivative of any of embodiments 1-158, the in vitro potency EC$_{50}$ value of which, at 0% HSA and/or 1.0% HSA, is at or below 20% of the EC$_{50}$ value of semaglutide.

160. The derivative of any of embodiments 1-159, the in vitro potency EC$_{50}$ value of which, at 0% HSA and/or 1.0% HSA, is at or below 10% of the EC$_{50}$ value of semaglutide.

161. The derivative of any of embodiments 1-160, which is capable of binding to the human GLP-1 receptor.

162. The derivative of embodiment 161, where the receptor binding activity is determined in vitro.

163. The derivative of any of embodiments 161-162, where the receptor binding is measured in a competitive binding assay, where a labelled ligand such as $^{125}$I-GLP-1 is bound to the receptor, the derivative is added in a desired series of concentrations, and displacement of the labelled ligand is monitored, preferably using a SPA binding assay.

164. The derivative of embodiment 163, where the receptor binding is reported as the concentration at which half of the labelled ligand is displaced from the receptor (the IC$_{50}$ value).

165. The derivative of any of embodiments 161-164, wherein activation of the human GLP-1 receptor is measured as GLP-1 receptor binding affinity (IC$_{50}$) in a very low concentration of serum albumin (approximately 0.001% HSA, final assay concentration), and/or in a high concentration of serum albumin (2.0% HSA, final assay concentration).

166. The derivative of any of embodiments 161-165, wherein isolated membranes containing the human GLP-1 receptor are used.

167. The derivative of embodiment 166, wherein the membranes are prepared from cells expressing the human GLP-1 receptor.

168. The derivative of embodiment 167, wherein the cells are BHK cells.

169. The derivative of embodiment 168, wherein the BHK cells have BHKTS13 as a parent cell line.

170. The derivative of embodiment 169, wherein the cells are BHK cells of clone FCW467-12A.

171. The derivative of any of embodiments 161-170, wherein the GLP-1 receptor binding affinity (IC$_{50}$) is determined as described in Example 30.

172. The derivative of any of embodiments 1-171, for which the GLP-1 receptor binding affinity (IC$_{50}$) in the presence of low albumin (approximately 0.001% HSA, final assay concentration) is
a) below 12 nM, preferably below 6.0 nM, more preferably below 3.0 nM, still more preferably below 1.5 nM, even more preferably below 1.0 nM, or most preferably below 0.50 nM;
c) below 0.20 nM, preferably below 0.18 nM, even more preferably below 0.16 nM, or most preferably below 0.15 nM; or
d) below 0.14 nM, preferably below 0.13 nM, or most preferably below 0.12 nM.

173. The derivative of any of embodiments 1-172, for which the GLP-1 receptor binding affinity (IC$_{50}$) in the presence of high albumin (2.0% HSA, final assay concentration) is
a) below 1000 nM, preferably below 500 nM, more preferably below 300 nM;
b) below 200 nM, preferably below 100 nM, more preferably below 80 nM; or
c) below 70 nM, preferably below 40 nM, or more preferably below 30 nM.

174. The derivative of any of embodiments 1-173, which has a more protracted profile of action than liraglutide and/or semaglutide.

175. The derivative of embodiment 174, wherein protracted profile of action refers to terminal half-life in vivo in a relevant animal species, such as db/db mice, rat, pig, and dog, preferably mini pig and/or beagle dog; wherein the derivative is administered i) s.c., and/or, ii) i.v.; preferably ii) i.v.

176. The derivative of any of embodiments 1-175, wherein the terminal half-life (t½) after i.v. administration to mini pigs is
a) at least 12 hours, preferably at least 18 hours, more preferably at least 24 hours, even more preferably at least 30 hours, or most preferably at least 36 hours;
b) at least 50 hours, preferably at least 55 hours, more preferably at least 60 hours, even more preferably at least 65 hours, or most preferably at least 70 hours; or
c) at least 74 hours, preferably at least 80 hours, more preferably at least 85 hours, still more preferably at least 90 hours, even more preferably at least 95 hours, or most preferably at least 100 hours.

177. The derivative of any of embodiments 1-176, wherein the terminal half-life (t½) after i.v. administration to mini pigs is
a) at least on par with that of semaglutide;
b) at least 25% higher than that of semaglutide;
c) at least 50% higher than that of semaglutide; or
d) at least 80% higher than that of semaglutide.

178. The derivative of any of embodiments 175-177, wherein the mini pigs are female, preferably obtained from Ellegaard Göttingen Minipigs.

179. The derivative of any of embodiments 175-178, wherein the mini pigs are approximately 5 months of age, and preferably weighing approximately 10 kg.

180. The derivative of any of embodiments 175-180, wherein the mini pigs are housed in pens with straw as bedding, four to six together in each pen and fed once or twice daily, preferably with Altromin 9023 mini pig diet.

181. The derivative of any of embodiments 175-180, wherein the derivative is dosed, i.v., after an acclimatisation period of 1 week.

182. The derivative of any of embodiments 175-181, wherein the GLP-1 derivative is dissolved in 50 mM sodium phosphate, 70 mM sodium chloride, 0.05% tween 80, pH 7.4 to a suitable concentration, such as 20 nmol/ml.

183. The derivative of any of embodiments 175-182, wherein intravenous injections of the derivative are given in a volume corresponding to, e.g., 2 nmol/kg.

184. The derivative of any of embodiments 175-183, wherein the terminal half-life (t½) is determined in in vivo pharmacokinetic studies in mini pig, for example as described in Example 31.

185. The derivative of any of embodiments 1-184, wherein the terminal half-life (t½) after i.v. administration to Beagle dogs is
a) at least 10 hours, preferably at least 20 hours, more preferably at least 30 hours, even more preferably at least 40 hours, or most preferably at least 50 hours; or
b) at least 60 hours, preferably at least 65 hours, more preferably at least 70 hours, still more preferably at least 75 hours, even more preferably at least 80 hours, or most preferably at least 85 hours.

186. The derivative of any of embodiments 1-185, wherein the terminal half-life (t½) after i.v. administration to Beagle dogs is
a) at least on par with that of semaglutide;
b) at least 10% higher than that of semaglutide;
c) at least 25% higher than that of semaglutide; or
d) at least 40% higher than that of semaglutide.

187. The derivative of any of embodiments 185-186, wherein the Beagle dogs are male and female (50:50), preferably obtained from Harland.

188. The derivative of any of embodiments 185-187, wherein the Beagle dogs are 21 to 30 months of age and weighing approximately 10-12 kg at the start of the studies.

189. The derivative of any of embodiments 185-188, wherein the Beagle dogs are housed in pens (12 hours light: 12 hours dark), preferably with softwood based granules as bedding, two together in each pen, and fed once daily, preferably with SPECIFIC™ Struvite Management Diet.

189. The derivative of any of embodiments 185-188, wherein the derivative is dosed, i.v., after an acclimatisation period of 4 weeks.

190. The derivative of any of embodiments 185-189, wherein the GLP-1 derivative is dissolved in 50 mM sodium phosphate, 70 mM sodium chloride, 70 ppm Polysorbate 20, pH 7.4 to a suitable concentration, such as 20 nmol/ml.

191. The derivative of any of embodiments 185-190, wherein intravenous injections of the derivative are given in a volume corresponding to, e.g., 2 nmol/kg.

192. The derivative of any of embodiments 185-191, wherein the terminal half-life (t½) is determined in in vivo pharmacokinetic studies in Beagle dogs, for example as described in Example 32.

193. A GLP-1 peptide which comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and no other Lys residues, or a pharmaceutically acceptable salt, amide, or ester thereof.

194. The peptide of embodiment 193 which has a maximum of seven amino acid changes as compared to GLP-1(7-37) (SEQ ID NO: 1), preferably a maximum of six amino acid changes, more preferably a maximum of five amino acid changes.

195. The peptide of any of embodiments 193-194, which comprises one or more of the following further amino acid changes: 8Aib, 22Glu, 26Arg, and/or (34Arg or 34Gln).

196. The peptide of any of embodiments 193-195, which comprises the following amino acid changes, as compared to GLP-1(7-37) (SEQ ID NO: 1): (i) 8Aib, 22Glu, 26Arg, 34Arg, 36Lys, and 37Lys; (ii) 8Aib, 26Arg, 34Arg, 36Lys, and 37Lys; or (iii) 8Aib, 22Glu, 26Arg, 34Gln, 36Lys, and 37Lys.

197. The peptide of any of embodiments 193-196, which has the following amino acid changes, as compared to GLP-1 (7-37) (SEQ ID NO:1):
(i) 8Aib, 22Glu, 26Arg, 34Arg, 36Lys, and 37Lys; (ii) 8Aib, 26Arg, 34Arg, 36Lys, and 37Lys; or (iii) 8Aib, 22Glu, 26Arg, 34Gln, 36Lys, and 37Lys.

198. The peptide of any of embodiments 193-197 which is SEQ ID NO: 2, SEQ ID NO: 3, or SEQ ID NO: 4.

199. The peptide of any of embodiments 193-198, wherein the comparison with GLP-1(7-37) (SEQ ID NO: 1) is made by handwriting and eyeballing.

200. The peptide of any of embodiments 193-199, wherein the comparison with GLP-1(7-37) (SEQ ID NO: 1) is made by use of a standard protein or peptide alignment program.

201. The peptide of embodiment 200, wherein the alignment program is a Needleman-Wunsch alignment.

202. The peptide of any of embodiments 193-201, wherein the default scoring matrix and the default identity matrix is used.

203. The peptide of any of embodiments 193-202, wherein the scoring matrix is BLOSUM62.

204. The peptide of any of embodiments 193-203, wherein the penalty for the first residue in a gap is −10 (minus ten).

205. The peptide of any of embodiments 193-204, wherein the penalties for additional residues in a gap is −0.5 (minus point five).

206. A derivative according to any of embodiments 1-192, or a peptide according to any of embodiments 193-205, for use as a medicament.

207. A derivative according to any of embodiments 1-192, or a peptide according to any of embodiments 193-205, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

208. Use of a derivative according to any of embodiments 1-192, or a peptide according to any of embodiments 193-205, in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

209. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments 1-192, or a peptide according to any of embodiments 193-205.

The invention also relates to a derivative of a GLP-1 peptide, which peptide comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and a maximum of seven amino acid changes as compared to GLP-1(7-37) (SEQ ID NO: 1), which derivative comprises a first and a second protractor attached to said first and second Lys residue, respectively, via a first and a second linker, respectively, wherein the first and the second protractor are selected from:

| | |
|---|---|
| HOOC—$C_6H_4$—O—$(CH_2)_y$—CO—*, and | Chem. 1: |
| HOOC—$(CH_2)_x$—CO—*, | Chem. 2: | wherein y is an integer in the range of 9-11, and x is 12; and the first and the second linker comprises at least one of:

| | |
|---|---|
| *—NH—CH(COOH)—$(CH_2)_2$—CO—*, | Chem. 3: |
| *—NH—CH($(CH_2)_2$—COOH)—CO—*, and/or | Chem. 4: |
| *—NH—$(CH_2)_2$—[O—$(CH_2)_2$]$_k$—O—$[CH_2]_n$—CO—*, | Chem. 5: | wherein k is an integer in the range of 1-5, and n is an integer in the range of 1-5; or a pharmaceutically acceptable salt, amide, or ester thereof;

as well as any of the above embodiments 2-209 appended hereto as dependent embodiments, mutatis mutandis and/or by analogy.

The following are additional particular embodiments of the invention:

i). A derivative of a GLP-1 peptide, which peptide comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and a maximum of seven amino acid changes as compared to GLP-1(7-37) (SEQ ID NO: 1);

which derivative comprises two protractors attached to said first and second Lys residue, respectively, each via a linker; wherein the protractor is selected from:

| | |
|---|---|
| HOOC—$C_6H_4$—O—$(CH_2)_y$—CO—*, and | Chem. 1: |
| HOOC—$(CH_2)_x$—CO—*, | Chem. 2: | wherein y is an integer in the range of 9-11, and x is 12; and the linker comprises at least one of:

| | |
|---|---|
| *—NH—CH(COOH)—$(CH_2)_2$—CO—*, | Chem. 3: |
| *—NH—CH($(CH_2)_2$—COOH)—CO—*, and/or | Chem. 4: |
| *—NH—$(CH_2)_2$—[O—$(CH_2)_2$]$_k$—O—$[CH_2]_n$—CO—*, | Chem. 5: | wherein k is an integer in the range of 1-5, and n is an integer in the range of 1-5; or a pharmaceutically acceptable salt, amide, or ester thereof.

ii). The derivative of embodiment i), wherein Chem. 5 is represented by Chem. 5b: *—NH—$(CH_2)_2$—O—$(CH_2)_2$—O—$CH_2$—CO—*, and the linker consists of two Chem. 3 elements, and two Chem. 5b elements (2×Chem. 3-2×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.

iii). The derivative of embodiment i), wherein Chem. 5 is represented by Chem. 5b: *—NH—$(CH_2)_2$—O—$(CH_2)_2$—O—$CH_2$—CO—*, and the linker consists of one Chem. 3 element, and two Chem. 5b elements (Chem. 3-2×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.

iv). The derivative of embodiment i), wherein Chem. 5 is represented by Chem. 5b: *—NH—$(CH_2)_2$—O—$(CH_2)_2$—O—$CH_2$—CO—*, and the linker consists of one Chem. 3 element, and three Chem. 5b elements (Chem. 3-3×Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.

v). The derivative of embodiment i), wherein Chem. 5 is represented by Chem. 5b: *—NH—$(CH_2)_2$—O—$(CH_2)_2$—O—$CH_2$—CO—*, and the linker consists of two Chem. 4 elements, and one Chem. 5b element (2×Chem. 4-Chem. 5b), interconnected via amide bonds and in the sequence indicated, connected at its *—NH end to the CO—* end of the protractor, and at its CO—* end to the epsilon amino group of the first or the second Lys residue of the GLP-1 peptide.

vi). The derivative of any of embodiments i)-v), wherein as compared to GLP-1(7-37) (SEQ ID NO: 1) the peptide comprises the amino acid changes of 36Lys and 37Lys, and one or more of the following further amino acid changes: 8Aib, 22Glu, 26Arg, and/or (34Arg or 34Gln).

vii). The derivative of any of embodiments i)-vi), wherein the peptide comprises the following amino acid changes, as compared to GLP-1(7-37) (SEQ ID NO: 1): (i) 8Aib, 22Glu, 26Arg, 34Arg, 36Lys, and 37Lys; (ii) 8Aib, 26Arg, 34Arg, 36Lys, and 37Lys; or (iii) 8Aib, 22Glu, 26Arg, 34Gln, 36Lys, and 37Lys.

iix). The derivative of any of embodiments i)-vii), wherein the peptide is SEQ ID NO: 2, SEQ ID NO: 3, or SEQ ID NO: 4.

ix). A compound selected from the following:
N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],
N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2), Chem. 21:

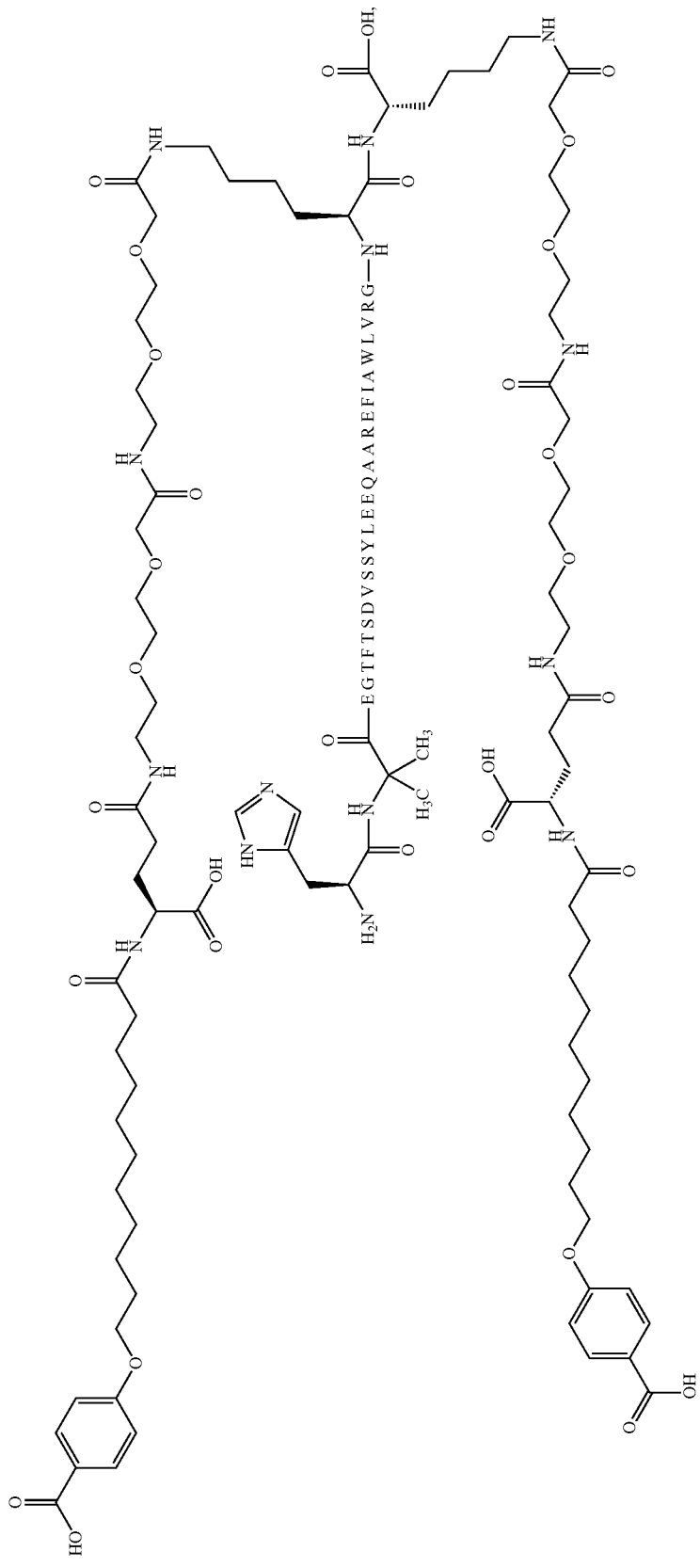

N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],
N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide
(Derivative of SEQ ID NO: 3),
Chem. 22:

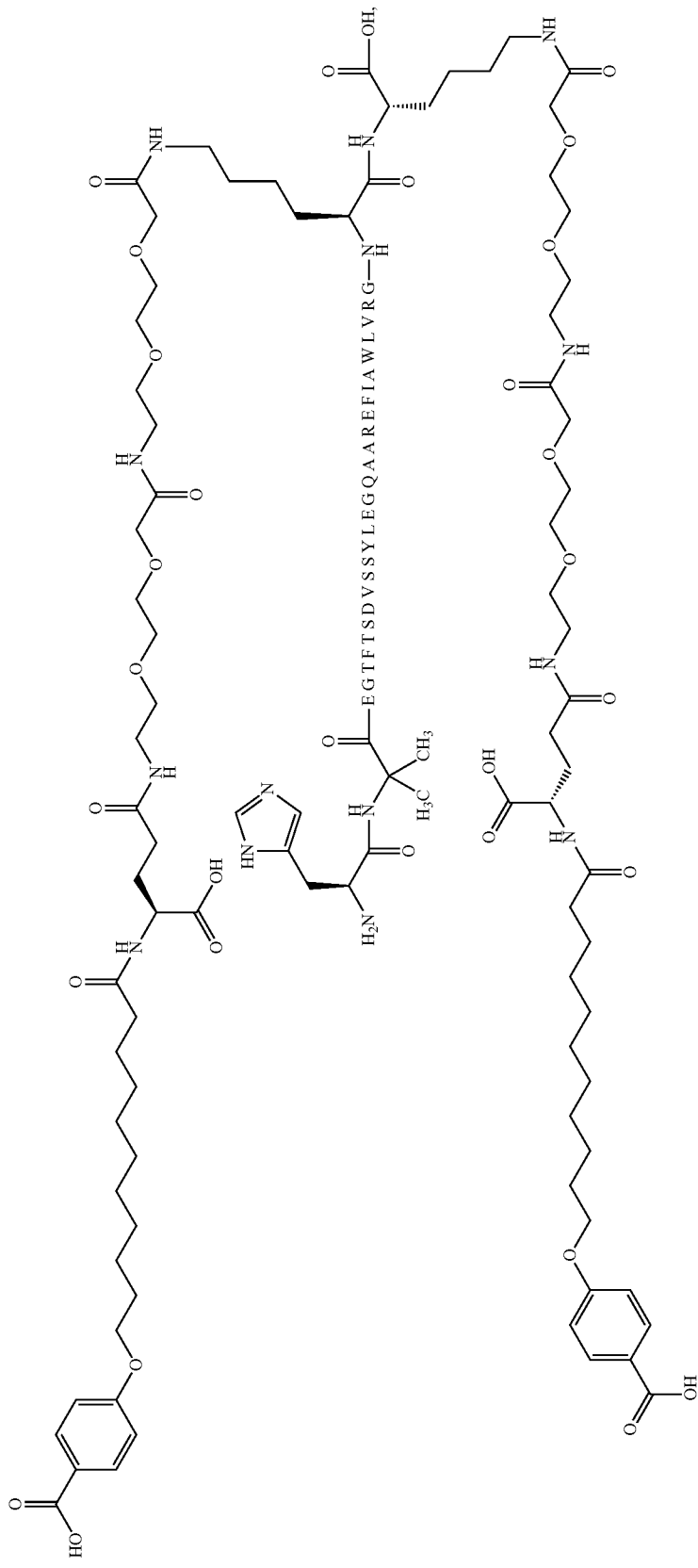

N{Epsilon-36}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl],
N{Epsilon-37}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2),
Chem. 23:

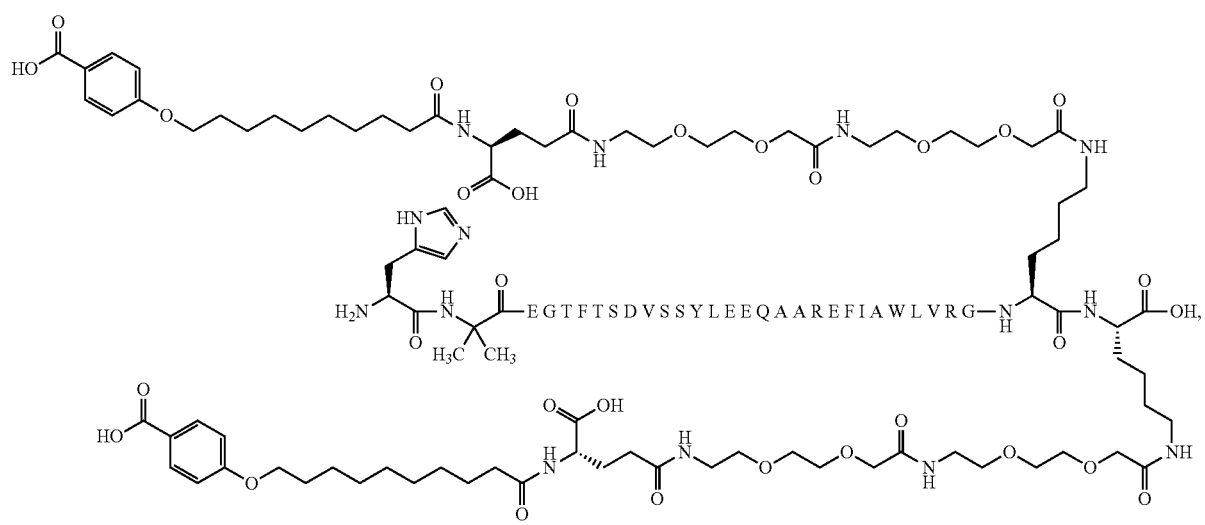

N{Epsilon-36}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl],
N{Epsilon-37}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3),
Chem. 24:

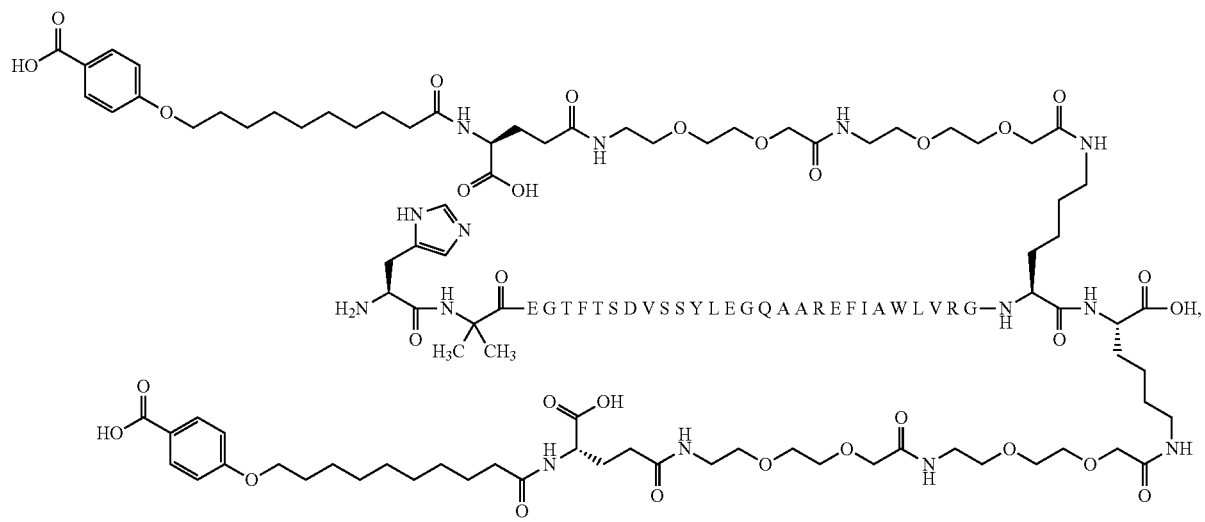

N{Epsilon-36}-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2), Chem. 25:

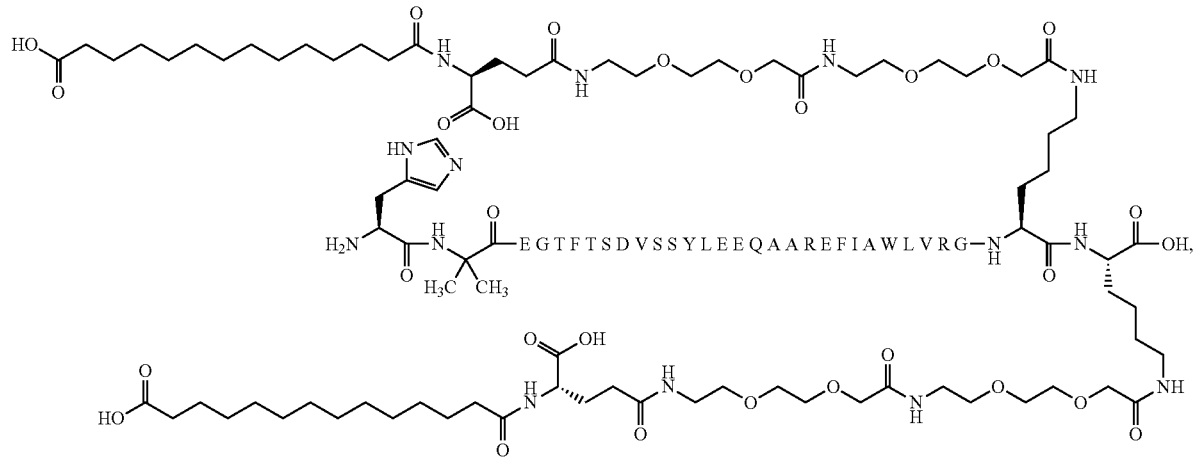

N{Epsilon-36}-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3), Chem. 26:

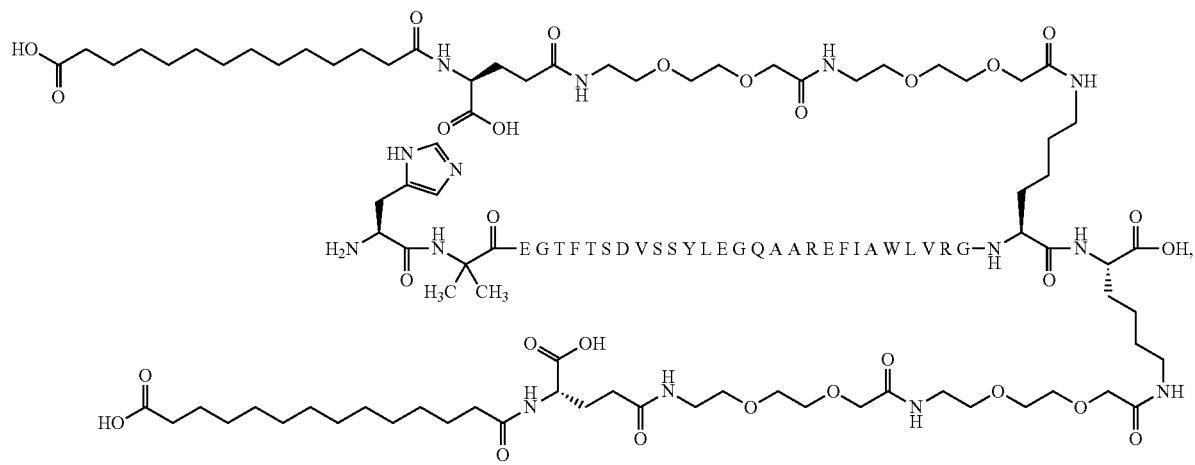

N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8, Glu22,Arg26,Gln34,Lys36,Lys37]-GLP-1-(7-37)-peptide (Derivative of SEQ ID NO: 4), Chem. 27:

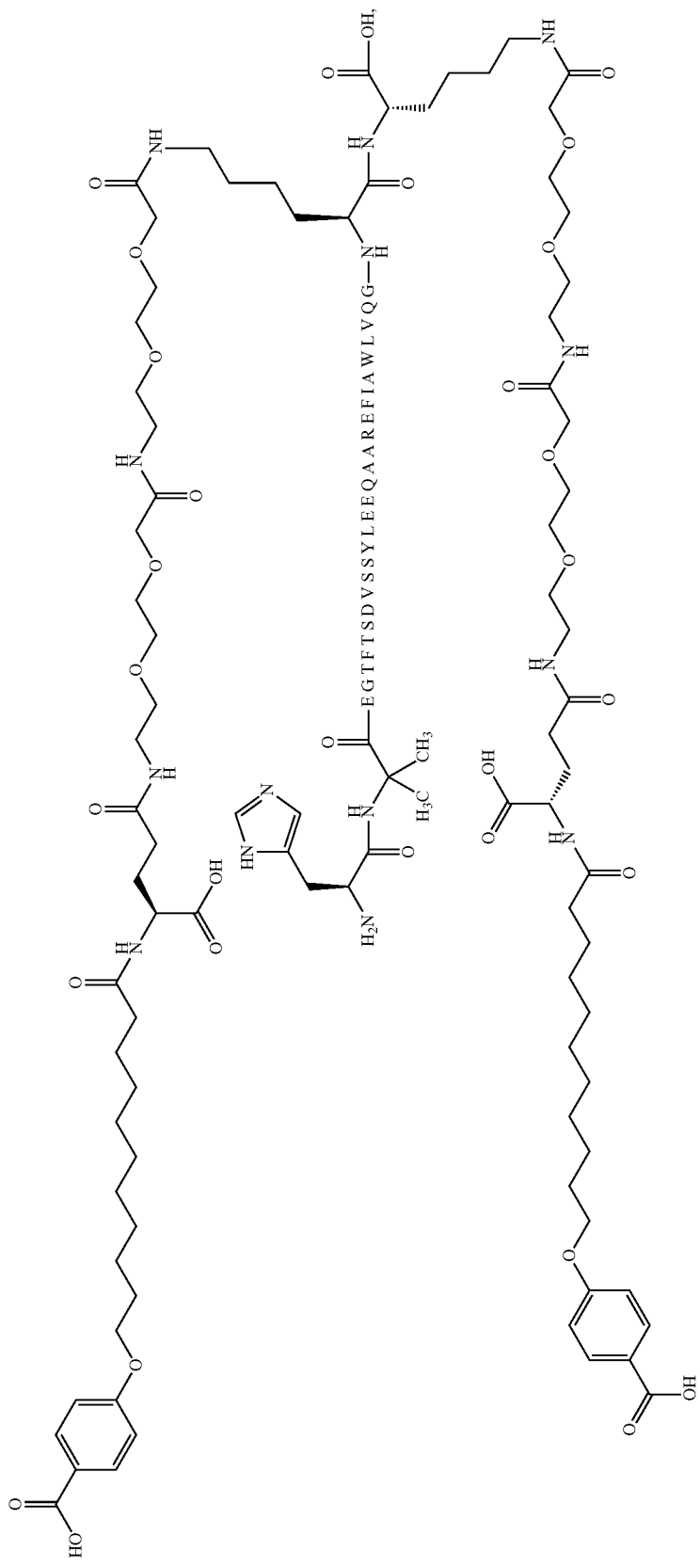

N{Epsilon-36}-[2-[2-[2-[[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]amino]ethoxy]ethoxy]acetyl]-[Aib8,Arg26,Arg34,Lys36,Lys36,Lys37]-GLP-1-(7-37)-peptide (Derivative of SEQ ID NO: 3), Chem. 28:

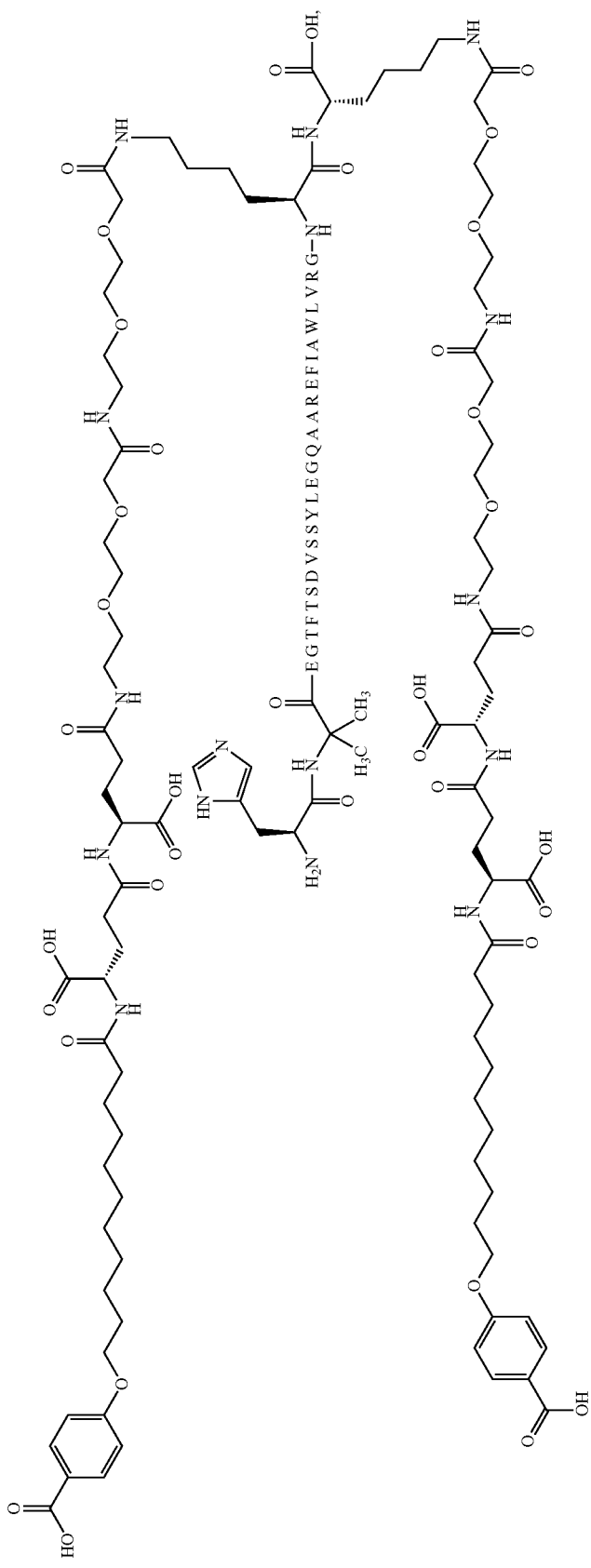

N{Epsilon-36}-[2-[2-[2-[[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3).

Chem. 29:

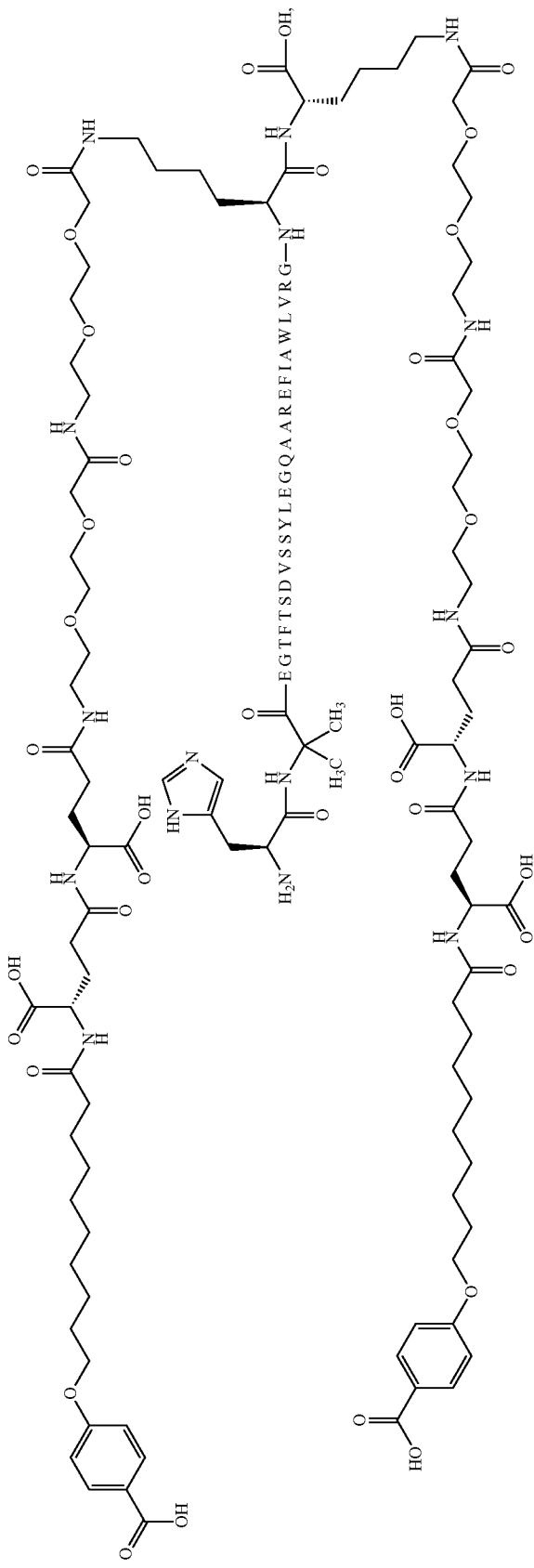

N{Epsilon-36}-[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl], N{Epsilon-37}-[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl]-[Aib8,Arg26,Arg34,Lys36,Lys37]-GLP-1-(7-37)-peptide (Derivative of SEQ ID NO: 3), Chem. 30:

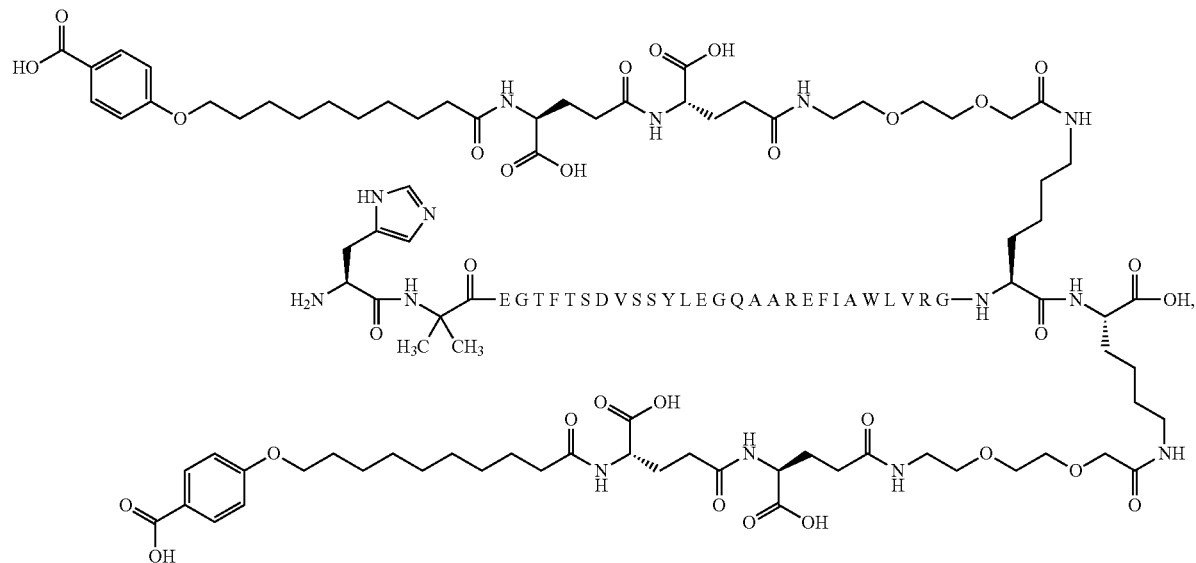

N{Epsilon-36}-[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl], N{Epsilon-37}-[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]-[Aib8,Arg26,Arg34,Lys36,Lys37]-GLP-1-(7-37)-peptide (Derivative of SEQ ID NO: 3), Chem. 31:

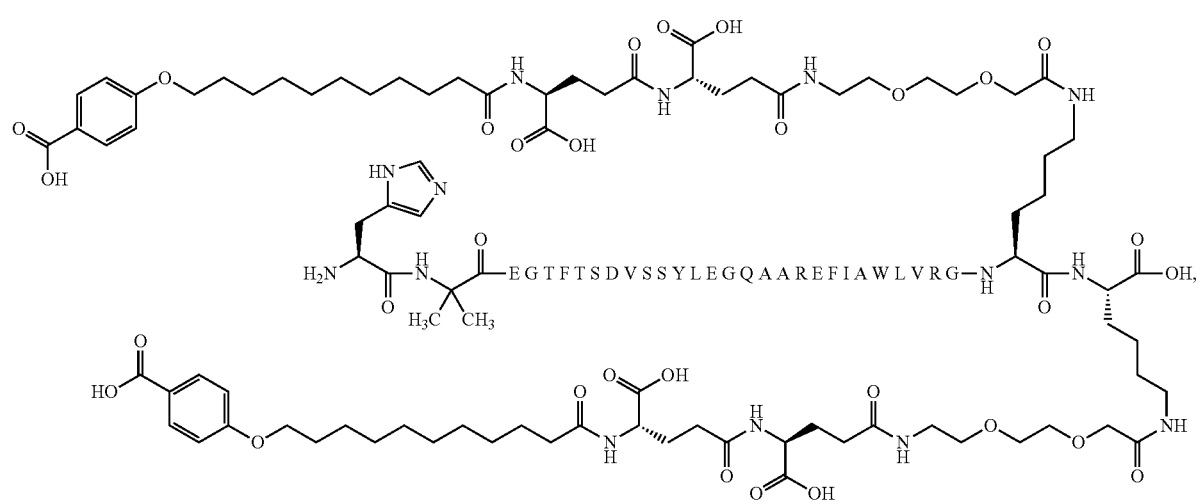

N{Epsilon-36}-[2-[2-[2-[[2-[2-[2-[[2-[2-[2-[[(4S)-4-carboxy-4-(1V R G-N N carboxytridecanoylamino)butanoyl]amino]ethoxy]ethoxy]acetyl]amino]ethoxy]ethoxy]acetyl]amino]ethoxy]ethoxy]acetyl], N{Epsilon-37}-[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2), Chem. 32:

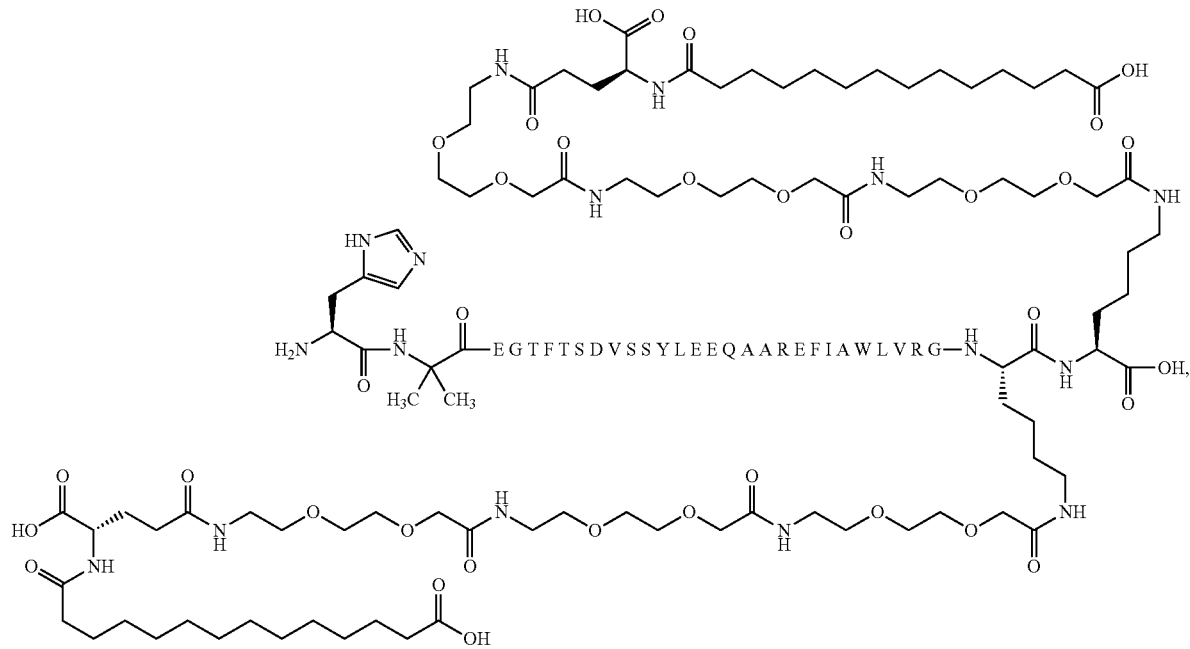

N{Epsilon-36}-[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl], N{Epsilon-37}-[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]-[Aib8,Glu22,Arg26,Arg34,Lys36,Lys37]-GLP-1-(7-37)-peptide (Derivative of SEQ ID NO: 2), Chem. 33:

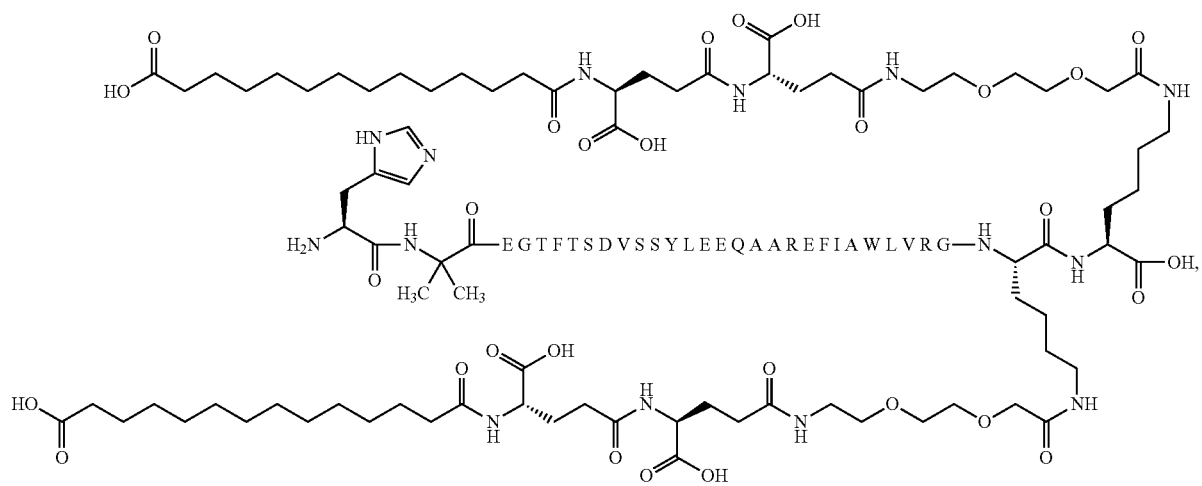

N{Epsilon-36}-[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl],
N{Epsilon-37}-[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide
(Derivative of SEQ ID NO: 3),
Chem. 34:

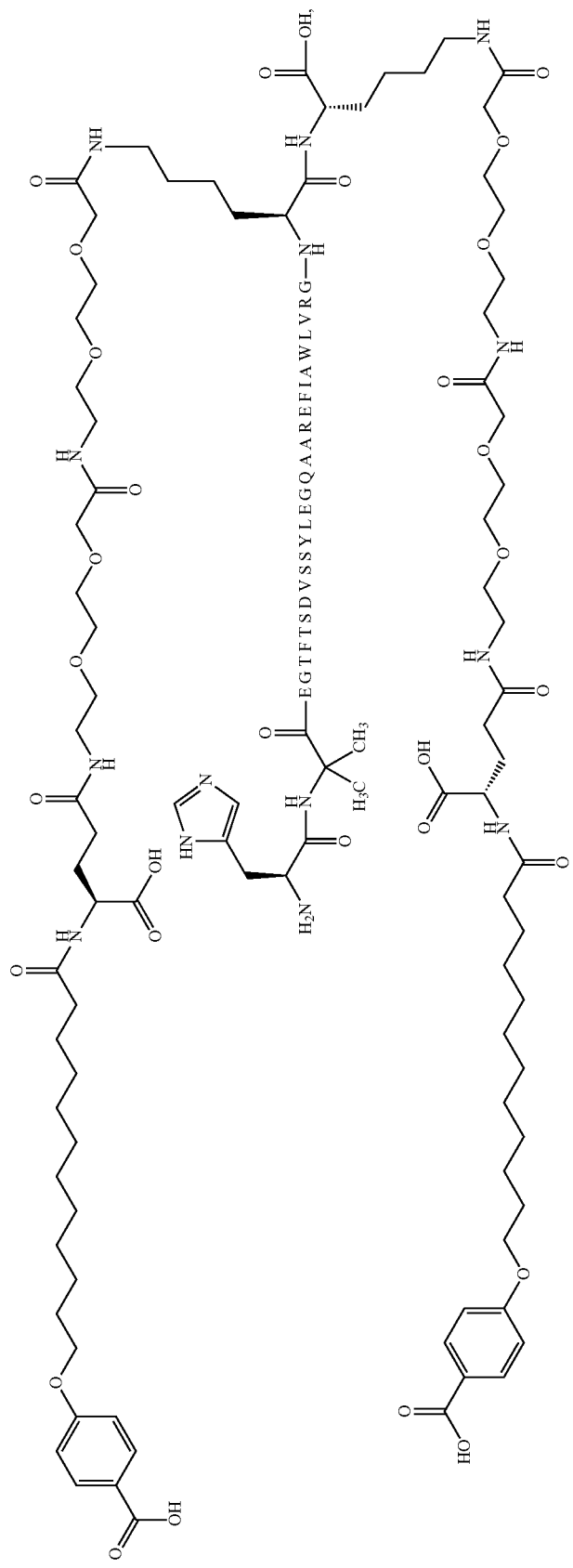

N{Epsilon-36}-[2-[2-[2-[[2-[2-[2-[[(4S)-4-carboxy-4-[car-boxy-(3-carboxyphenoxy)decanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-(7-37)-peptide (Derivative of SEQ ID NO: 2),
Chem. 35:

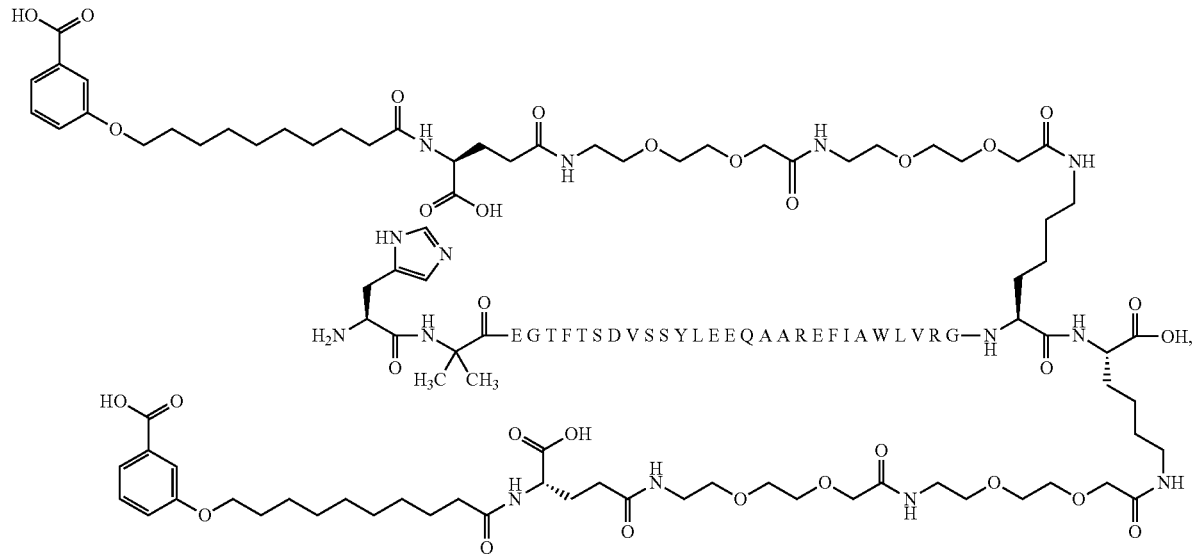

N{Epsilon-36}-[2-[2-[2-[[(2S)-4-carboxy-2-[[(2S)-4-carboxy-2-[11-(4-carboxyphenoxy)undecanoylamino]butanoyl]amino]butanoyl]amino]ethoxy]ethoxy]acetyl], N{Epsilon-37}-[2-[2-[2-[[(2S)-4-carboxy-2-[[(2S)-4-carboxy-2-[11-(4-carboxyphenoxy)undecanoylamino]butanoyl]amino]butanoyl]amino]ethoxy]ethoxy]acetyl]-[Aib8,Arg26,Arg34,Lys36,Lys37]-GLP-1-(7-37)-peptide (Derivative of SEQ ID NO: 3), and
Chem. 36:

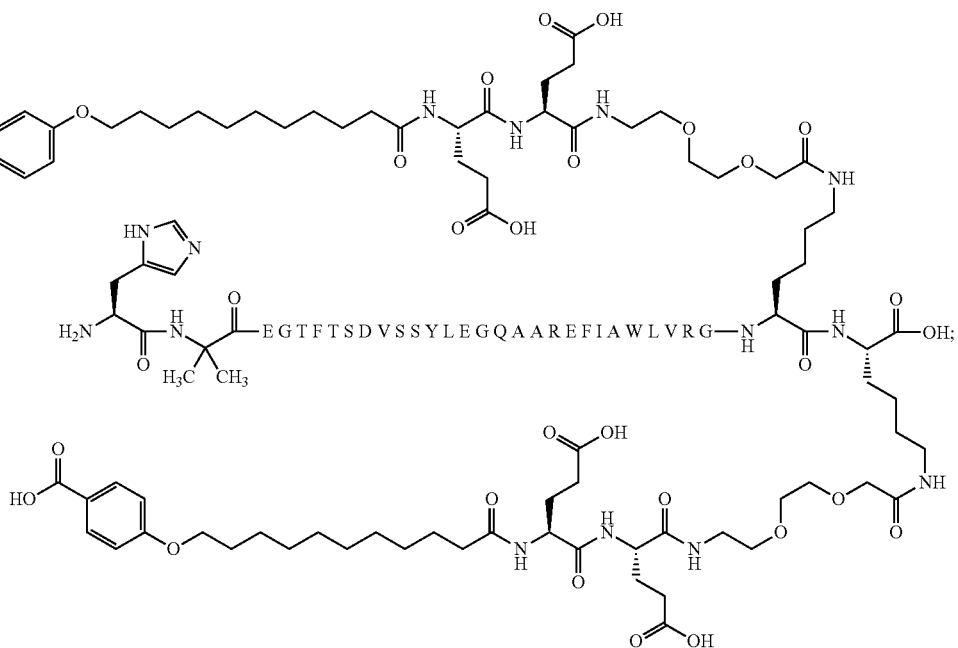

or a pharmaceutically acceptable salt, amide, or ester thereof.

x). A GLP-1 peptide which comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and no other Lys residues, or a pharmaceutically acceptable salt, amide, or ester thereof.

xi). The peptide of embodiment x), which has a maximum of seven amino acid changes as compared to GLP-1(7-37) (SEQ ID NO: 1).

xii). The peptide of any of embodiments x)-xi), which comprises the following amino acid changes, as compared to GLP-1(7-37) (SEQ ID NO: 1): (i) 8Aib, 22Glu, 26Arg, 34Arg, 36Lys, and 37Lys; (ii) 8Aib, 26Arg, 34Arg, 36Lys, and 37Lys; or (iii) 8Aib, 22Glu, 26Arg, 34Gln, 36Lys, and 37Lys.

xiii). The peptide of any of embodiments x)-xii), which is SEQ ID NO: 2, SEQ ID NO: 3, or SEQ ID NO: 4.

xiv). A derivative according to any of embodiments i)-ix), or a peptide according to any of embodiments x)-xiii) for use as a medicament.

xv). A derivative according to any of embodiments i)-ix), or a peptide according to any of embodiments x)-xiii), for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

Abbreviations

The following abbreviations are used in the following, in alphabetical order:

Aib: α-aminoisobutyric acid
API: Active Pharmaceutical Ingredient
AUC: Area Under the Curve
BG: Blood Glucose
BHK Baby Hamster Kidney
BW: Body Weight
Bom: benzyloxymethyl
Boc: t-butyloxycarbonyl
BSA: Bovine serum albumin
Bzl: benzyl
CAS: Chemical Abstracts Service
Clt: 2-chlorotrityl
collidine: 2,4,6-trimethylpyridine
DCM: dichloromethane
Dde: 1-(4,4-dimethyl-2,6-dioxocyclohexylidene)ethyl
DIC: diisopropylcarbodiimide
DIPEA: diisopropylethylamine
DMAP: 4-dimethylaminopyridine
DMEM: Dulbecco's Modified Eagle's Medium (DMEM)
EDTA: ethylenediaminetetraacetic acid
EGTA: ethylene glycol tetraacetic acid
FCS: Fetal Calf Serum
Fmoc: 9-fluorenylmethyloxycarbonyl
HATU: (O-(7-azabenzotriazol-1-yl)-1,1,3,3-tetramethyluronium hexafluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid
i.v. intravenously
ivDde: 1-(4,4-d imethyl-2,6-d ioxocyclohexylidene)-3-methylbutyl
IVGTT: Intravenous Glucose Tolerance Test
LCMS: Liquid Chromatography Mass Spectrometry
LYD: Landrace Yorkshire Duroc
MALDI-MS: See MALDI-TOF MS
MALDI-TOF MS: Matrix-Assisted Laser Desorption/Ionisation Time of Flight Mass Spectrometry
MeOH: methanol
Mmt: 4-methoxytrityl
Mtt: 4-methyltrityl
NMP: N-methyl pyrrolidone
OBn: Benzyl ester
OBz: benzoyl ester
Ado: 8-amino-3,6-dioxaoctanoic acid
OPfp: pentafluorophenoxy
OPnp: para-nitrophenoxy
OSu: O-succinimidyl esters (hydroxysuccinimide esters)
OSuc: 2,5-dioxo-pyrrolidin-1-yl
OtBu: tert butyl ester
Oxyma Pure®: Cyano-hydroxyimino-acetic acid ethyl ester
Pbf: 2,2,4,6,7-pentamethyldihydrobenzofuran-5-sulfonyl
PBS: Phosphate Buffered Saline
PD: Pharmacodynamic
Pen/Strep: Pencillin/Streptomycin
PK: Pharmacokinetic
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl (trityl)
Trx: tranexamic acid
UPLC: Ultra Performance Liquid Chromatography Methods of Preparation A. General Methods A1. Methods of Preparation This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), 3. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular albumin binding moiety attachment using SPPS the following suitably protected building blocks such as but not limited to Fmoc-8-amino-3,6-dioxaoctanoic acid, Fmoc-tranexamic acid, Fmoc-Glu-OtBu, octadecanedioic acid mono-tert-butyl ester, nonadecanedioic acid mono-tert-butyl ester, tetradecanedioic acid mono-tert-butyl ester, or 4-(9-carboxynonyloxy) benzoic acid tert-butyl ester were used. All operations stated below were performed at 250-µmol synthesis scale.

1. Synthesis of Resin Bound Protected Peptide Backbone

Method: SPPS_P

SPPS_P was performed on a Prelude Solid Phase Peptide Synthesiser from Protein Technologies (Tucson, Ariz. 85714 U.S.A.) at 250-µmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 20% piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SPPS_L

SPPS_L was performed on a microwave-based Liberty peptide synthesiser from CEM Corp. (Matthews, N.C. 28106, U.S.A.) at 250-µmol or 100-µmol scale using six fold excess of Fmoc-amino acids (300 mM in NMP with 300 mM HOAt or Oxyma Pure®) relative to resin loading, e.g. low load Fmoc-Lys(Mtt)-Wang (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/(HOAt or Oxyma Pure®)/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, (HOAt or Oxyma Pure®) and DIC), and the mixture is heated again (e.g. 5 min at 75° C.). NMP washes (5×10 ml) were performed between deprotection and coupling steps.

2. Synthesis of Side Chains

Mono Esters of Diacids

Overnight reflux of the C8, C10, C12, C14, C16 and C18 diacids with Boc-anhydride DMAP t-butanol in toluene gives predominately the t-butyl mono ester. Obtained is after work-up a mixture of mono acid, diacid and diester. Purification is carried out by washing, short plug silica filtration and crystallisation.

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by NMP washings (7 ml×5). The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

If N-ε-lysine protection group was Mtt, the Mtt group was removed with neat HFIP (3×15 min) followed by washings with DCM and the acylation performed on a Prelude peptide synthesiser ((10 eq. Fmoc-AA, 10 eq. DIC and 10 eq. HOAt, 10 eq. collidine 30 min and 25% piperidine in NMP to remove the Fmoc-group). Fmoc-Glu-OtBu was double coupled for 4 hours. The terminal residue was attached using similar conditions.

Method: SC_L

The N-ε-lysine protection group was removed as described above and the chemical modification of the lysine was performed by one or more automated steps on the Liberty peptide synthesiser using suitably protected building blocks as described above. Double couplings were performed as described in SPPS_L.

4. Clevage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 pM column, using acetonitrile/water/TFA. The fractions were analysed by a combination of UPLC, MALDI and LCMS methods, and the appropriate fractions were pooled and lyophilised.

A2. General Methods for Detection and Characterisation

1. LC-MS Methods

Method: LCMS_4

LCMS_4 was performed on a setup consisting of Waters Acquity UPLC system and LCT Premier XE mass spectrometer from Micromass. Eluents: A: 0.1% Formic acid in water B: 0.1% Formic acid in acetonitrile The analysis was performed at RT by injecting an appropriate volume of the sample (preferably 2-10 μl) onto the column which was eluted with a gradient of A and B. The UPLC conditions, detector settings and mass spectrometer settings were: Column: Waters Acquity UPLC BEH, C-18, 1.7 μm, 2.1 mm×50 mm.

Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES Scan: 100-2000 amu (alternatively 500-2000 amu), step 0.1 amu.

2. UPLC Methods

Method: B4_1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 5% A, 95% B over 16 minutes at a flow-rate of 0.40 ml/min.

B. Synthesis of Compounds of the Invention

Example 1

This compound is a derivative of the GLP-1 analogue of SEQ ID NO: 2: N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2)

Chem. 21:

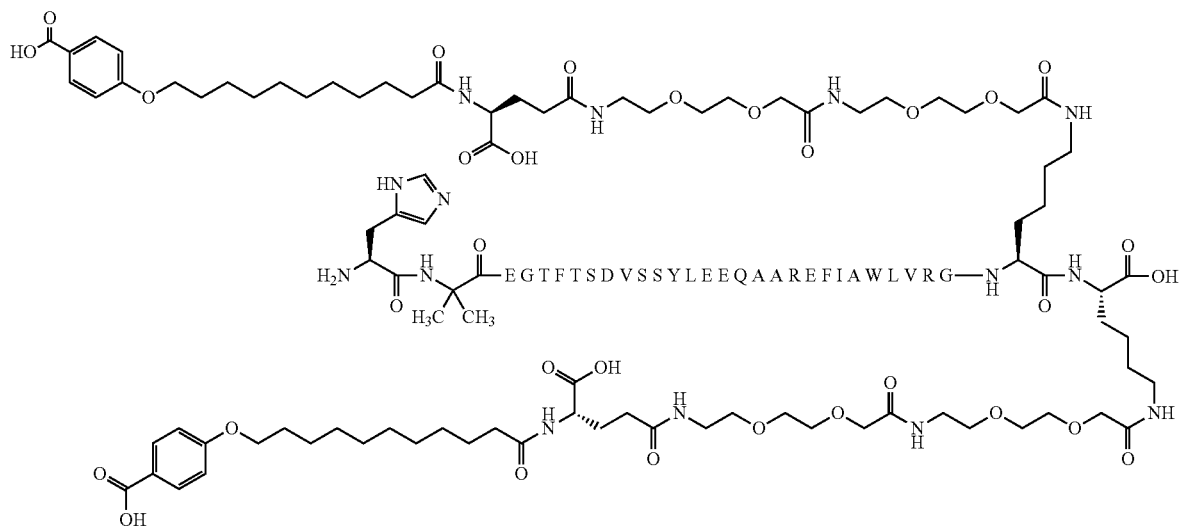

Preparation Method: SPPS_P; SC_L; CP_M1

LCMS_4: Rt=2.2 min m/z: m/4=1248, m/3=1663

UPLC_B4_1: Rt=7.2 min

Example 2

This compound is a derivative of the GLP-1 analogue of SEQ ID NO: 3: N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3)

Chem. 22:

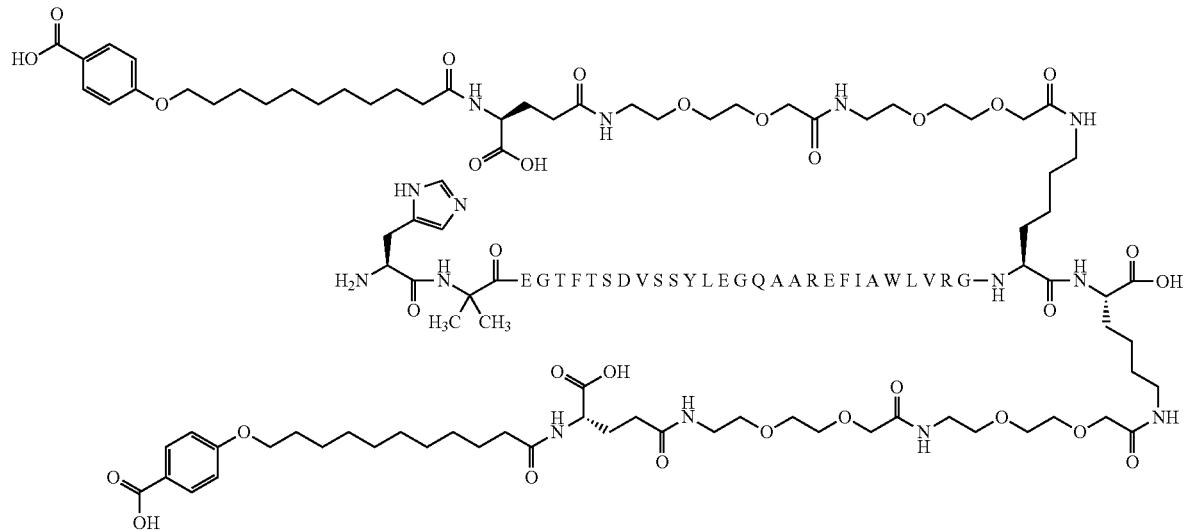

Preparation Method: SPPS_P; SC_L; CP_M1
LCMS_4: Rt=2.2 min m/z: m/4=1230, m/3=1639
UPLC_B4_1: Rt=8.9 min Example 3

This compound is a derivative of the GLP-1 analogue of SEQ ID NO: 2: N{Epsilon-36}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2)

Chem. 23:

Preparation Method: SPPS_L; SC_PL; CP_M1
LCMS_4: Rt=2.2 min m/z: m/4=1241, m/3=1654
UPLC_B4_1: Rt=8.5 min Example 4

This compound is a derivative of the GLP-1 analogue of SEQ ID NO: 3: N{Epsilon-36}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3)

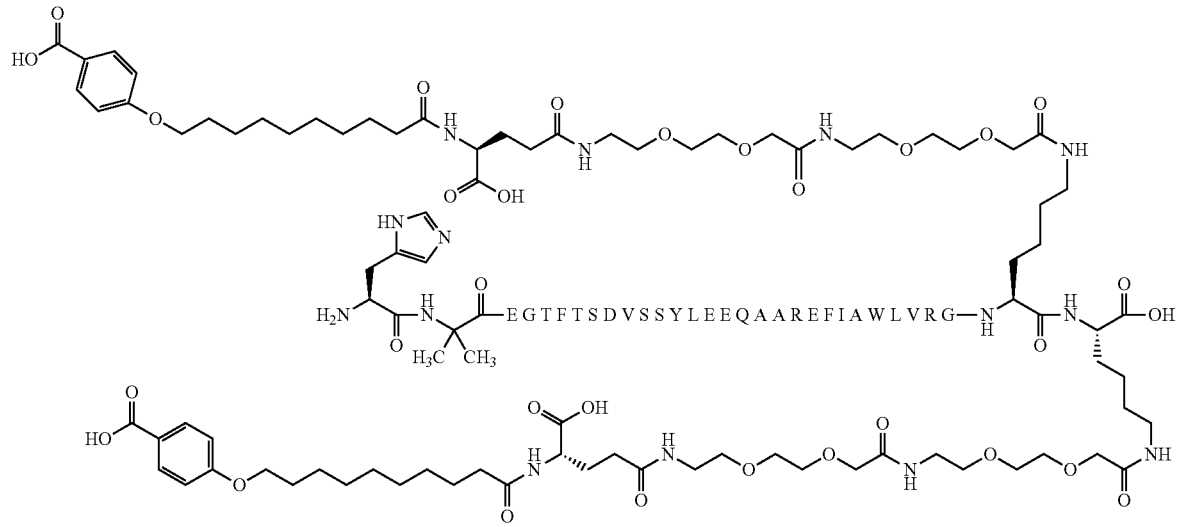

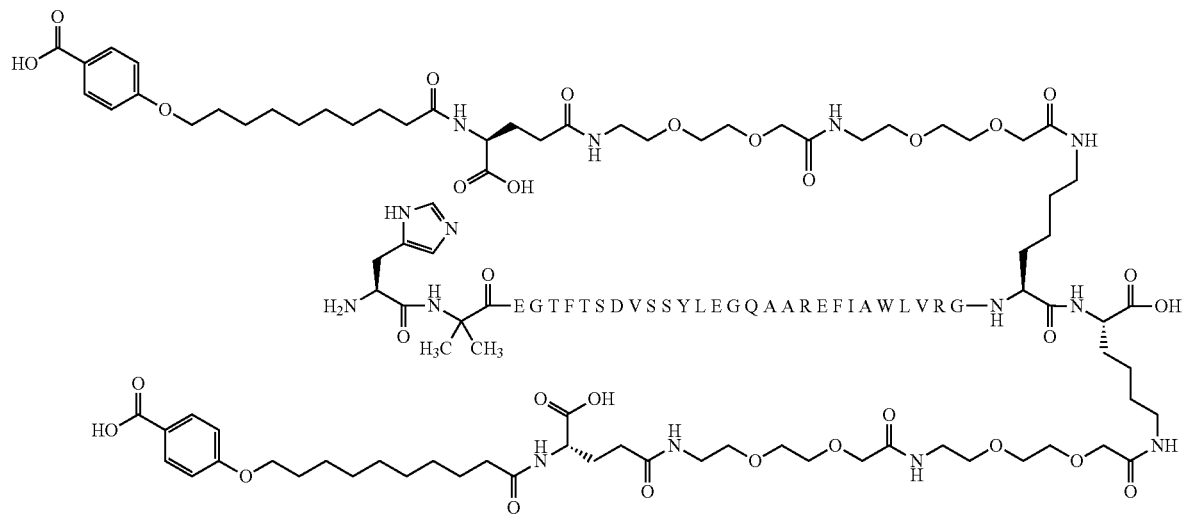

Preparation Method: SPPS_P; SC_P; CP_M1
LCMS_4: Rt=2.3 min m/z: m/4=1223, m/3=1630
UPLC_B4_1: Rt=8.56 min

Example 5

This compound is a derivative of the GLP-1 analogue of SEQ ID NO: 2: N{Epsilon-36}-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2)
Chem. 25:

Preparation Method: SPPS_P; SC_P; CP_M1
LCMS_4: Rt=2.3 min m/z: m/4=1216, m/3=1621
UPLC_B4_1: Rt=8.56 min

Example 6

This compound is a derivative of the GLP-1 analogue of SEQ ID NO: 3:

N{Epsilon-36}-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3)

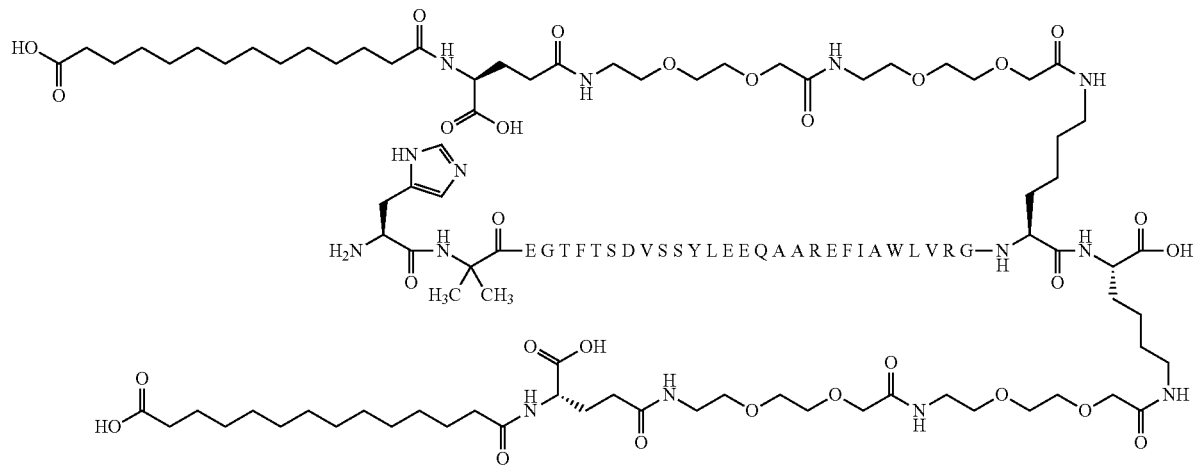

Chem. 26:

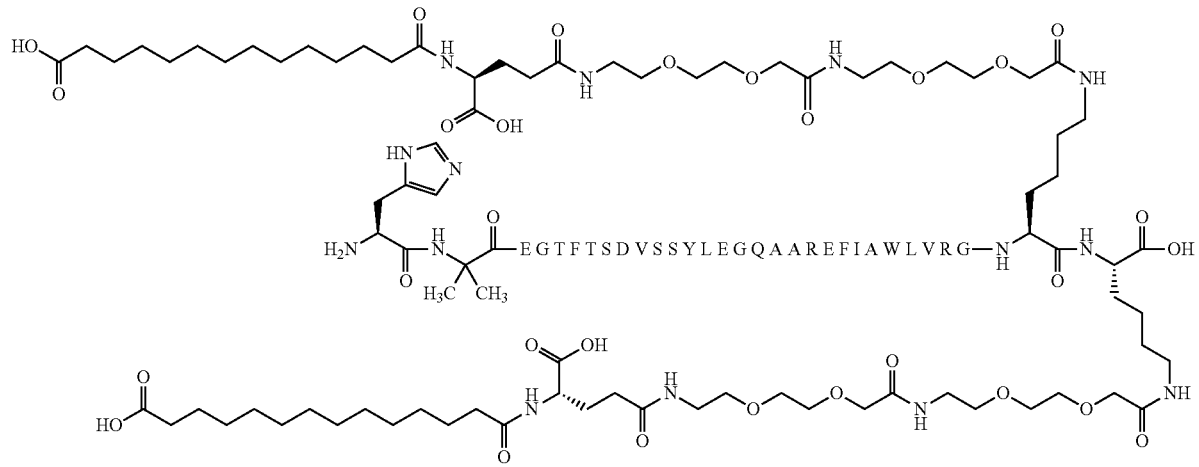

Preparation Method: SPPS_P; SC_P; CP_M1
LCMS_4: Rt=2.3 min m/z: m/4=1198, m/3=1597
UPLC_B4: Rt=8.54 min

Example 7

This compound is a derivative of the GLP-1 analogue of SEQ ID NO: 3:
N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl], N{[Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8, Glu22,Arg26,Gln34,Lys36,Lys37]-GLP-1-(7-37)-peptide (Derivative of SEQ ID NO: 4)
Chem. 27:

Preparation Method: SPPS_P; SC_P; CP_M1
LCMS_4: Rt=2.3 min m/z: m/4=1241, m/3=1654
UPLC_B4_1: Rt=9.3 min

Example 8

This compound is a derivative of the GLP-1 analogue of SEQ ID NO: 3: N{Epsilon-36}-[2-[2-[2-[[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3)

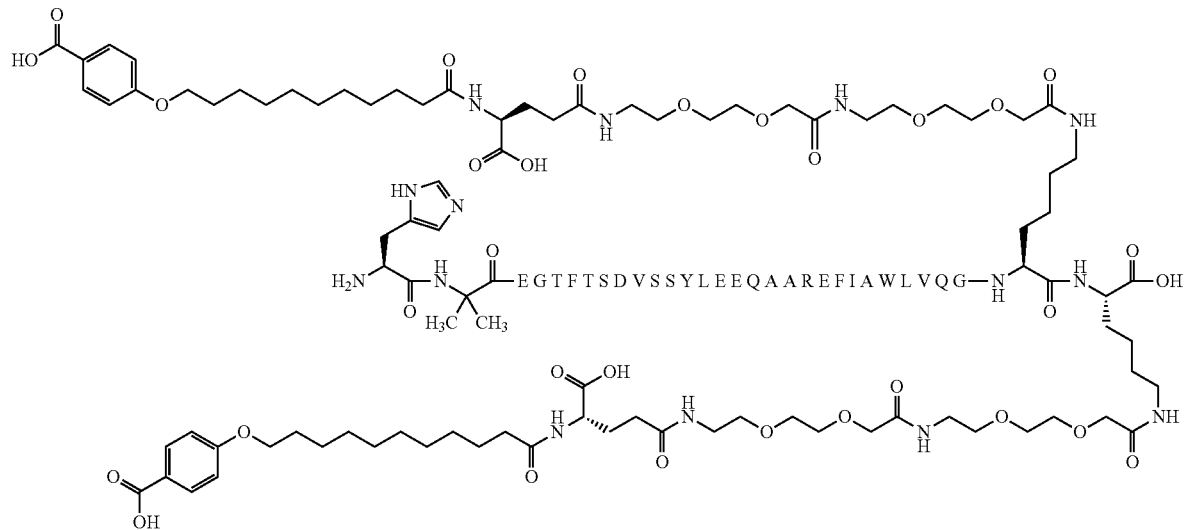

Chem. 28:

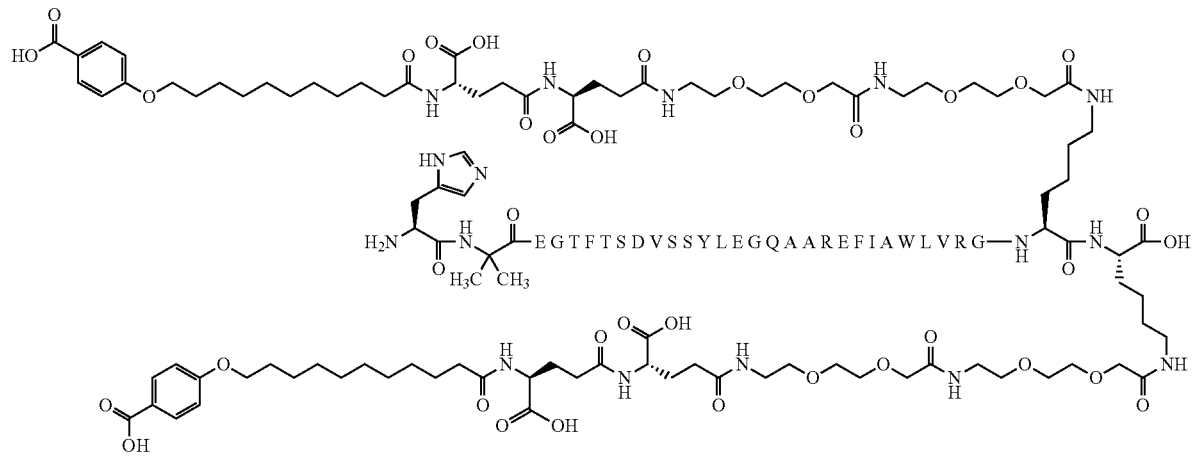

Preparation Method: SPPS_P; SC_L; CP_M1
LCMS_4: Rt=2.2 min m/z: m/4=1294, m/3=1726
UPLC_B4_1: Rt=8.58 min Example 9

This compound is a derivative of the GLP-1 analogue of SEQ ID NO: 3: N{Epsilon-36}-[2-[2-[2-[[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3)
Chem. 29:

Preparation Method: SPPS_P; SC_L; CP_M1
LCMS_4: Rt=2.1 min m/z: m/4=1287, m/3=1716
UPLC_B4_1: Rt=8.25 min Example 10

This compound is a derivative of the GLP-1 analogue of SEQ ID NO: 3: N{Epsilon-36}-[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl], N{Epsilon-37}-[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl]-[Aib8,Arg26,Arg34,Lys36,Lys37]-GLP-1-(7-37)-peptide (Derivative of SEQ ID NO: 3)

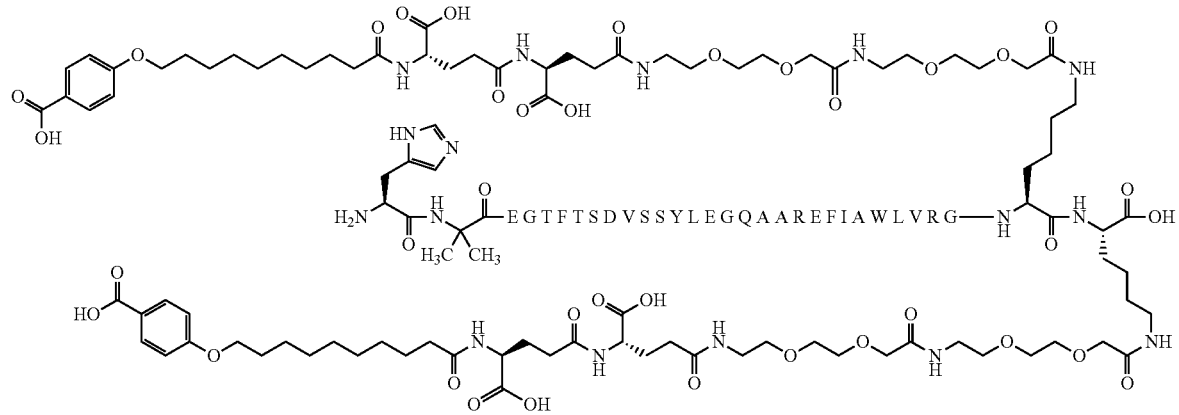

Chem. 30:

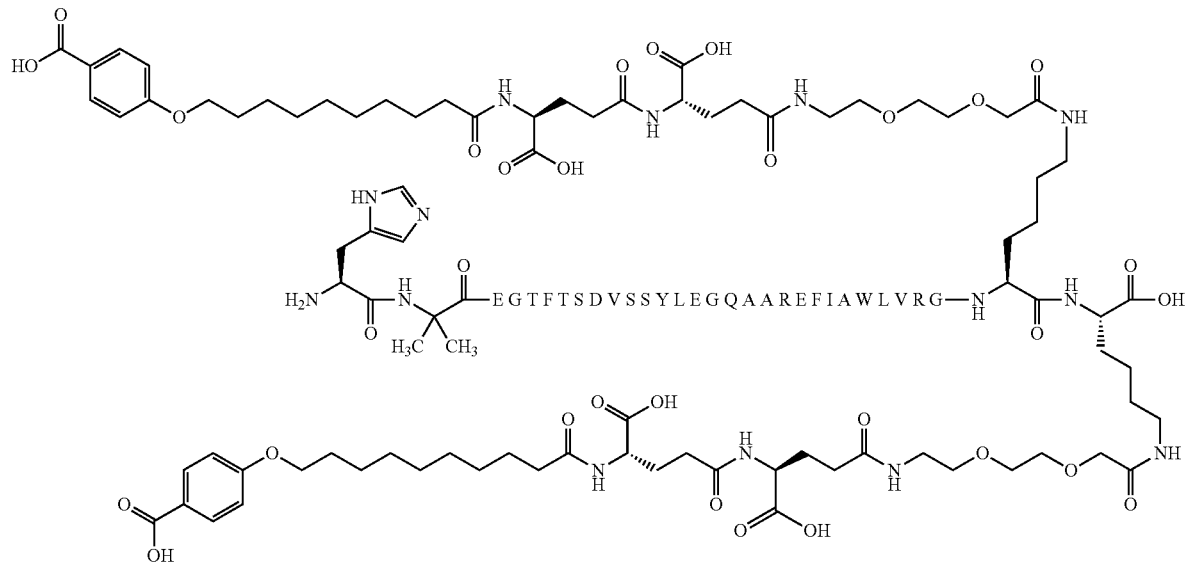

Preparation Method: SPPS_P; SC_L; CP_M1
LCMS_4: Rt=2.2 min m/z: m/4=1215, m/3=1619
UPLC_B4_1: Rt=8.45 min Example 11

This compound is a derivative of the GLP-1 analogue of SEQ ID NO: 3: N{Epsilon-36}-[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl], N{Epsilon-37}-[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]-[Aib8,Arg26,Arg34,Lys36,Lys37]-GLP-1-(7-37)-peptide
(Derivative of SEQ ID NO: 3)
Chem. 31:

Preparation Method: SPPS_P; SC_L; CP_M1
LCMS_4: Rt=2.2 min m/z: m/4=1222, m/3=1629
UPLC_B4_1: Rt=8.76 min Example 12

This compound is a derivative of the GLP-1 analogue of SEQ ID NO: 2: N{Epsilon-36}-[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl], N{Epsilon-37}-[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide
(Derivative of SEQ ID NO: 2)

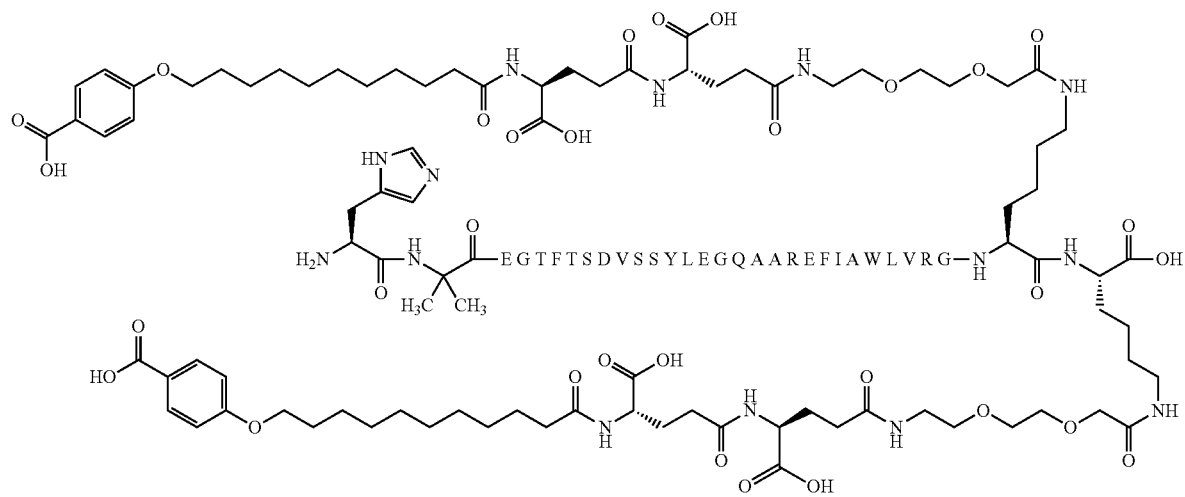

Chem. 32:

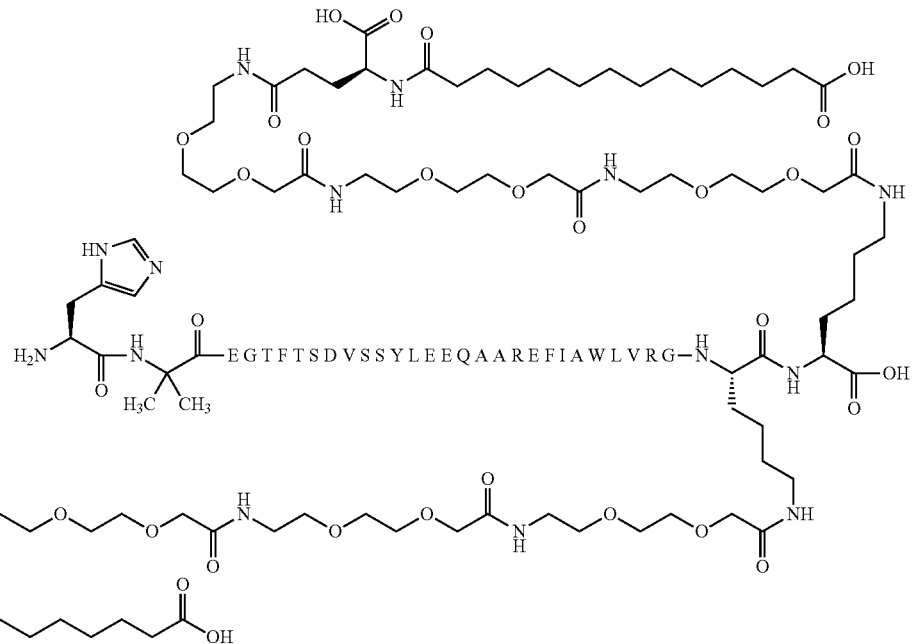

Preparation Method: SPPS_L; SC_L; CP_M1
LCMS_4: Rt=2.1 min m/z: m/4=1288, m/3=1718
UPLC_B4_1: Rt=8.53 min Example 13

This compound is a derivative of the GLP-1 analogue of SEQ ID NO: 2: N{Epsilon-36}-[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl], N{Epsilon-37}-[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]-[Aib8,Glu22,Arg26,Arg34,Lys36,Lys37]-GLP-1-(7-37)-peptide (Derivative of SEQ ID NO: 2)
Chem. 33:

Preparation Method: SPPS_P; SC_P; CP_M1
LCMS_4: Rt=2.1 min m/z: m/4=1208, m/3=1610
UPLC_B4_1: Rt=8.56 min Example 14

This compound is a derivative of the GLP-1 analogue of SEQ ID NO: 3: N{Epsilon-36}-[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3)

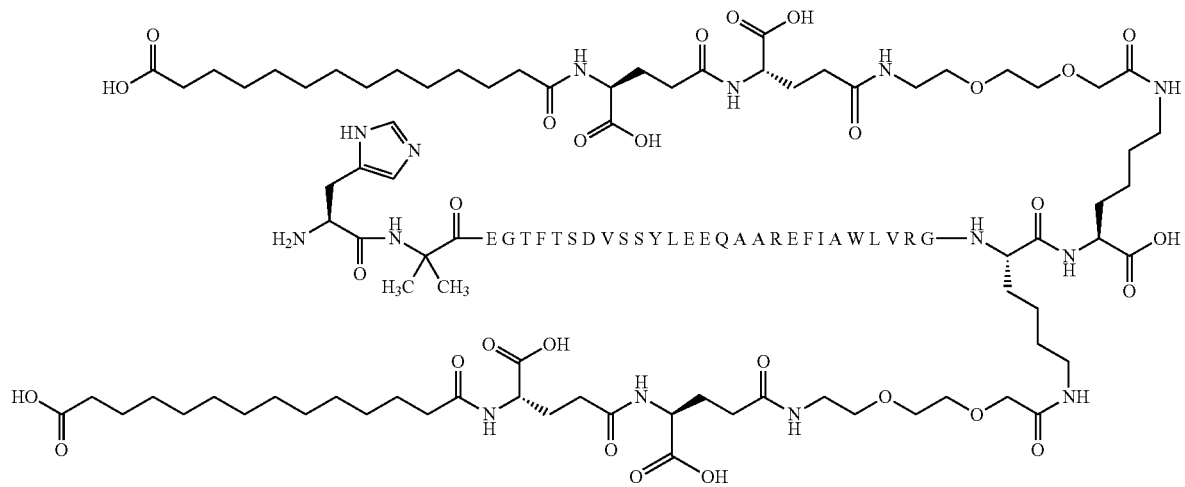

Chem. 34:

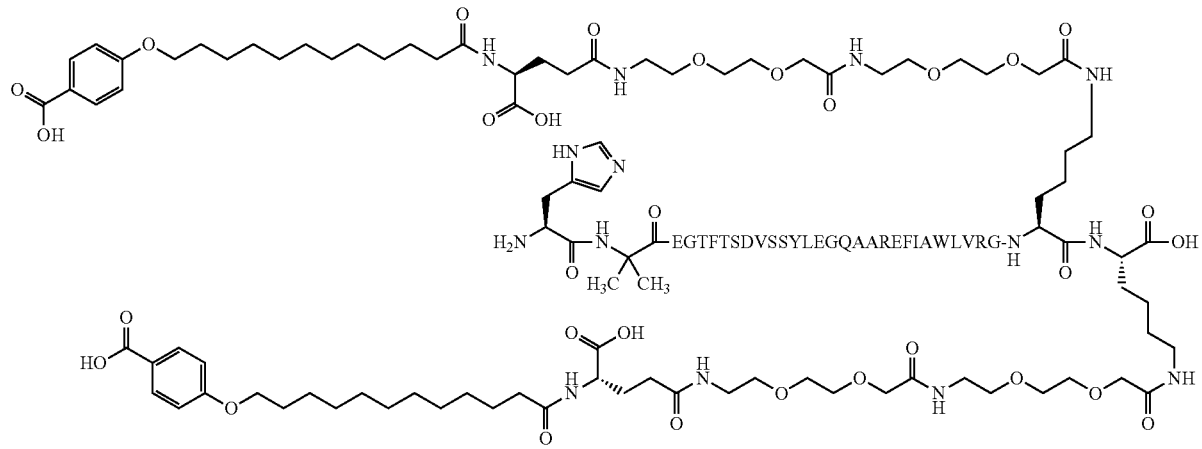

Preparation Method: SPPS_P; SC_L; CP_M1
LCMS_4: Rt=2.4 min m/z: m/4=1237, m/3=1648
UPLC_B4_1: Rt=9.2 min Preparation Method: SPPS_L; SC_L; CP_M1
LCMS_4: Rt=2.3 min m/z: m/4=1240, m/3=1654
UPLC_B4_1: Rt=8.9 min Example 15

This compound is a derivative of the GLP-1 analogue of SEQ ID NO: 2: N{Epsilon-36}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2)

Chem. 35:

Example 16

This compound is a derivative of the GLP-1 analogue of SEQ ID NO: 3: N{Epsilon-36}-[2-[2-[2-[[(2S)-4-carboxy-2-[[(2S)-4-carboxy-2-[11-(4-carboxyphenoxy)undecanoylamino]butanoyl]amino]butanoyl]amino]ethoxy]ethoxy]acetyl], N{Epsilon-37}-[2-[2-[2-[[(2S)-4-carboxy-2-[[(2S)-4-carboxy-2-[11-(4-carboxyphenoxy)undecanoylamino]butanoyl]amino]butanoyl]amino]ethoxy]ethoxy]acetyl]-[Aib8,Arg26,Arg34,Lys36,Lys37]-GLP-1-(7-37)-peptide (Derivative of SEQ ID NO: 3)

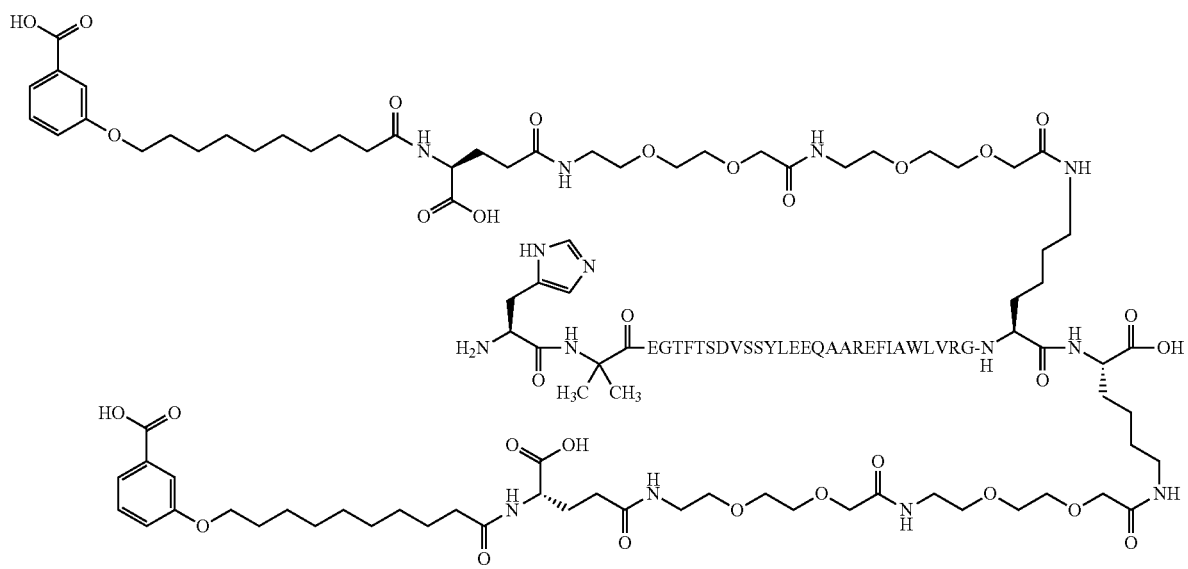

Chem. 36:

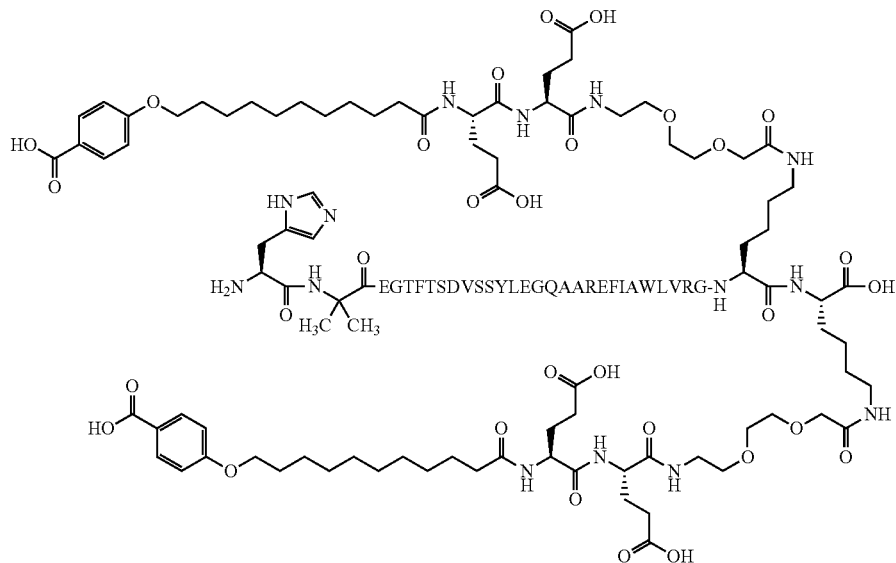

Preparation Method: SPPS_P; SC_L; CP_M1
LCMS_4: Rt=2.2 min m/z: m/4=1222, m/3=1629
UPLC_B4_1: Rt=8.71 min

Example 17

This compound is a derivative of the GLP-1 analogue of SEQ ID NO: 5: N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Gly8,Glu22,Arg26,Arg34,Lys36,Lys37]-GLP-1-(7-37)-peptide (Derivative of SEQ ID NO: 5)
Chem. 37:

Preparation Method: SPPS_P; SC_P; CP_M1
LCMS_4: Rt=2.4 min m/z: m/4=1241, m/3=1655
UPLC_B4_1: Rt=8.6 min

Example 18

This compound is a derivative of the GLP-1 analogue of SEQ ID NO: 2: N{Epsilon-36}-[2-[2-[2-[[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[[(4S)-4-carboxy-4-[11-(4-carboxyphenoxy)undecanoylamino]butanoyl]amino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2)

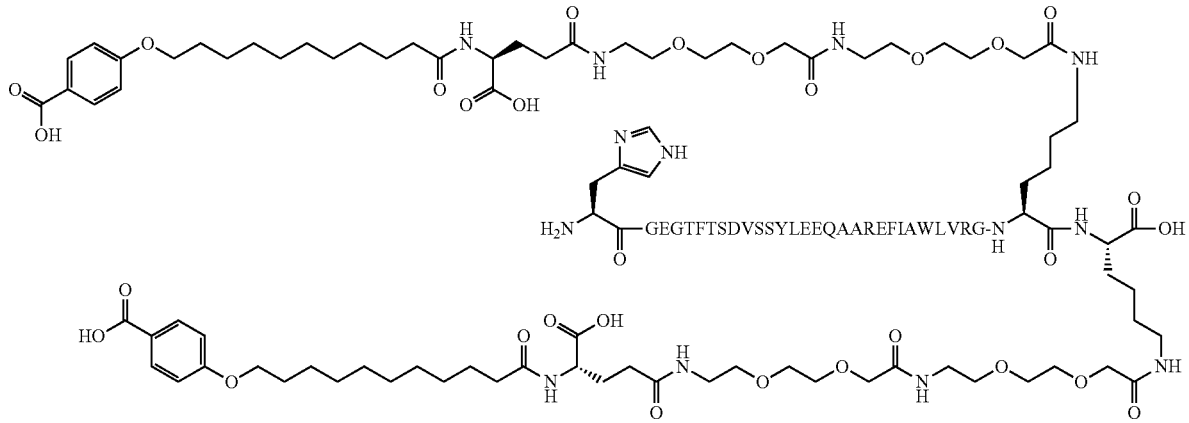

Chem. 38:

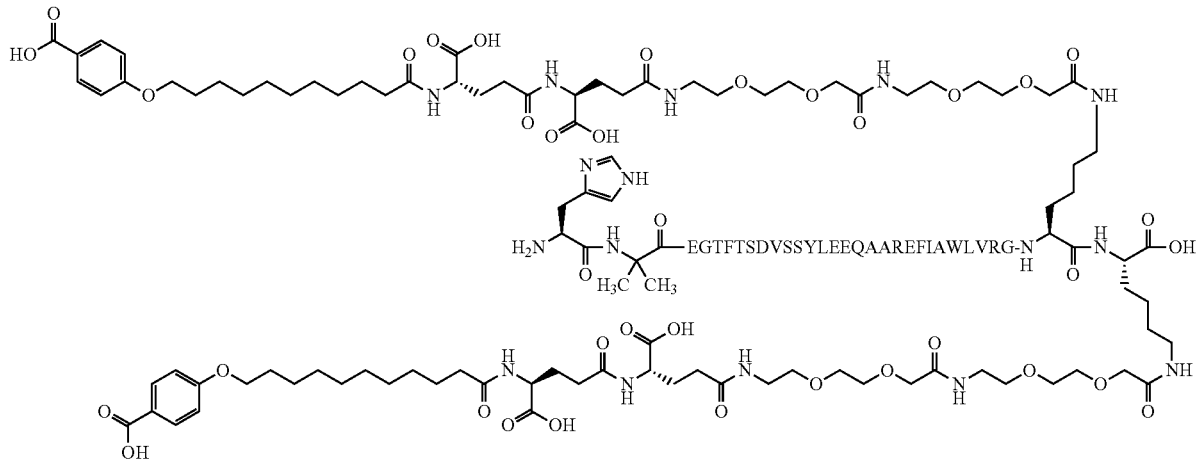

Preparation Method: SPPS_P; SC_P; CP_M1
LCMS_4: Rt=2.4 min m/z: m/4=1312, m/3=1749
UPLC_B4_1: Rt=8.7 min

Example 19

This compound is a derivative of the GLP-1 analogue of SEQ ID NO: 3: N{Epsilon-36}-[2-[2-[2-[[2-[2-[2-[[(4S)-4-carboxy-4-[[(4S)-4-carboxy-4-[[(4S)-4-carboxy-4-[11-(4-carboxyphenoxy)undecanoylamino]butanoyl]amino]butanoyl]amino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[[(4S)-4-carboxy-4-[[(4S)-4-carboxy-4-[11-(4-carboxyphenoxy)undecanoylamino]butanoyl]amino]butanoyl]amino]butanoyl]amino]ethoxy]ethoxy]acetyl]amino]ethoxy]ethoxy]acetyl]-[Aib8,Arg26,Arg34, Lys36, Lys37]-GLP-1-(7-37)-peptide (Derivative of SEQ ID NO: 3)

Chem. 39:

Preparation Method: SPPS_L; SC_L; CP_M1
LCMS_4: Rt=2.3 min m/z: m/4=1359, m/3=1811
UPLC_B4_1: Rt=8.4 min

Example 20

This compound is a derivative of the GLP-1 analogue of SEQ ID NO: 2: N{Epsilon-36}-[2-[2-[2-[[2-[2-[2-[[2-[2-[[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl], N{Epsilon-37}-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]-[Aib8,Glu22,Arg26,Arg34, Lys36,Lys37]-GLP-1-(7-37)-peptide (Derivative of SEQ ID NO: 2)

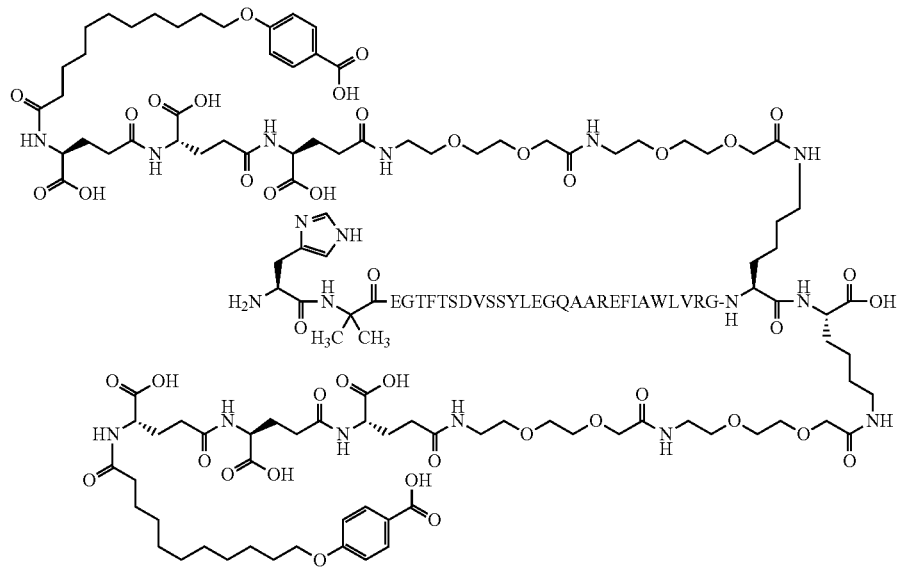

Chem. 40:

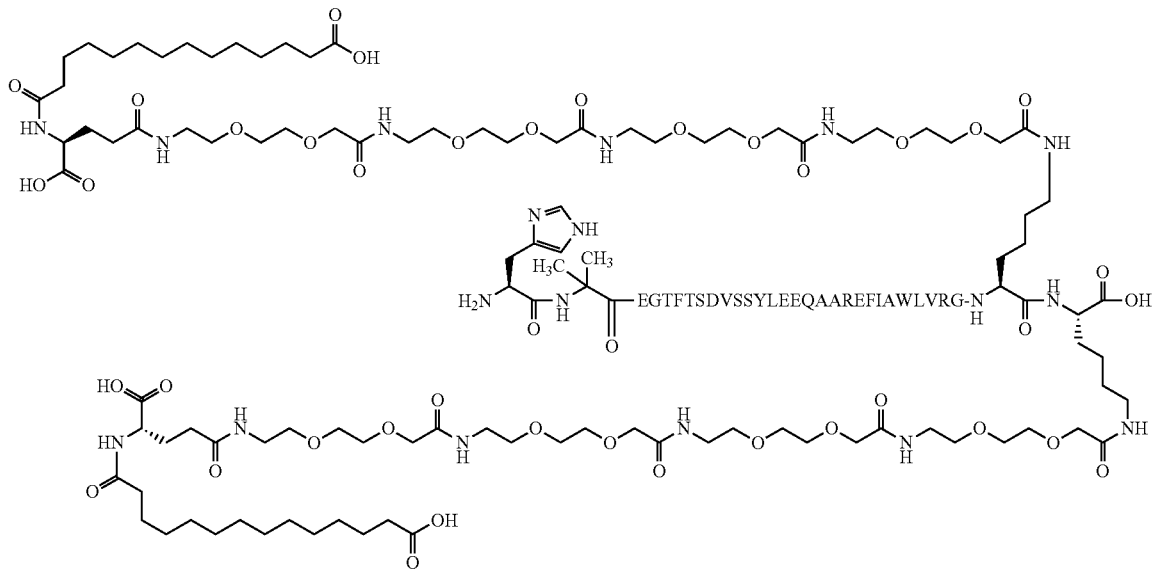

Preparation Method: SPPS_P; SC_P; CP_M1
LCMS_4: Rt=2.2 min m/z: m/4=1361, m/3=1814
UPLC_B4_1: Rt=8.2 min Example 21

This compound is a derivative of the GLP-1 analogue of SEQ ID NO: 2: N{Epsilon-36}-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2)
Chem. 41:

Preparation Method: SPPS_P; SC_P; CP_M1
LCMS_4: Rt=2.3 min m/z: m/4=1280, m/3=1707
UPLC_B4_1: Rt=8.4 min Example 22

This compound is a derivative of the GLP-1 analogue of SEQ ID NO: 2: N{Epsilon-36}-[2-[2-[2-[[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]amino]ethoxy]ethoxy]acetyl], N{Epsilon-37}-[2-[2-[2-[[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2)

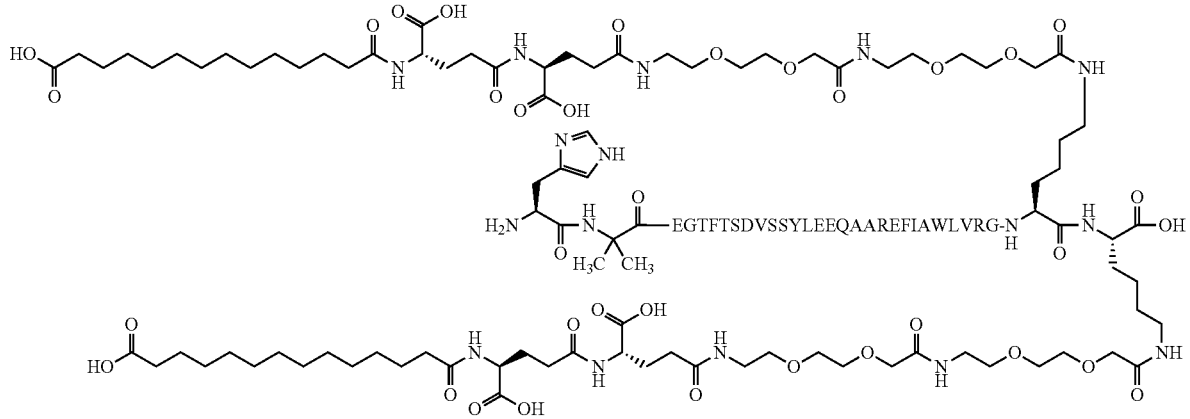

Chem. 42:

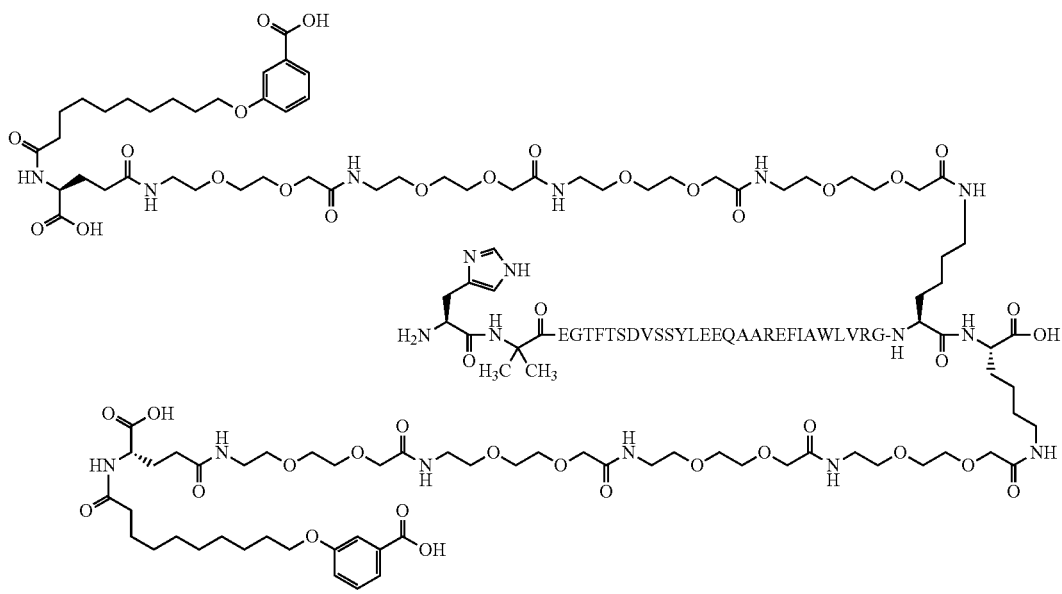

Preparation Method: SPPS_P; SC_P; CP_M1
LCMS_4: Rt=2.1 min m/z: m/4=1386, m/3=1848
UPLC_B4_1: Rt=8.2 min Example 23

This compound is a derivative of the GLP-1 analogue of SEQ ID NO: 2: N{Epsilon-36}-[2-[2-[2-[[2-[2-[2-[[(4S)-4-carboxy-4-[9-(3-carboxyphenoxy)nonanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[9-(3-carboxyphenoxy)nonanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2)
Chem. 43:

Preparation Method: SPPS_L; SC_L; CP_M1
LCMS_4: Rt=2.1 min m/z: m/5=988, m/4=1234
UPLC_B4_1: Rt=8.0 min Example 24

This compound is a derivative of the GLP-1 analogue of SEQ ID NO: 3: N{Epsilon-36}-[2-[2-[2-[[2-[2-[2-[[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl], N{Epsilon-37}-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3)

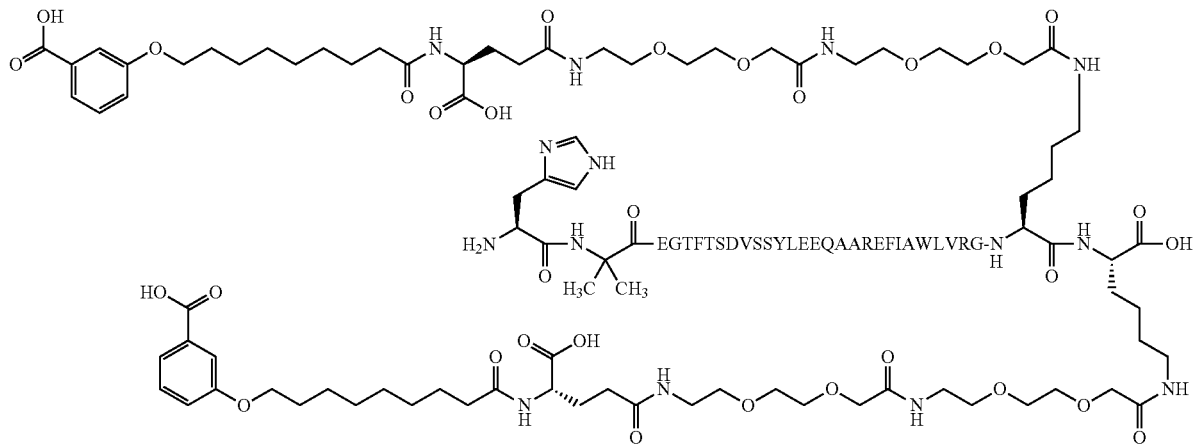

Chem. 44:

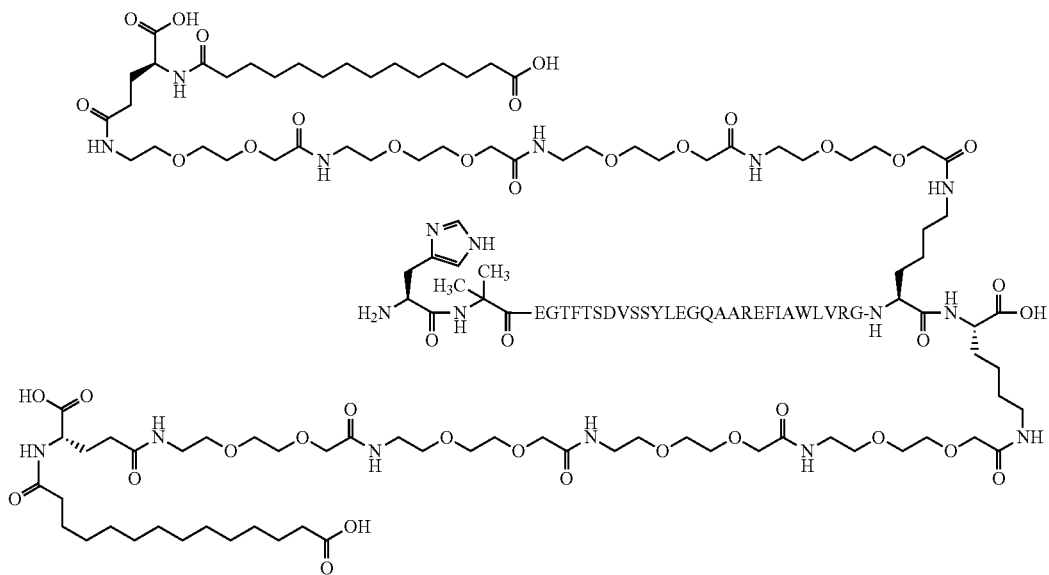

Preparation Method: SPPS_L; SC_L; CP_M1
LCMS_4: Rt=2.1 min m/z: m/5=1075, m/4=1343
UPLC_B4_1: Rt=8.0 min Example 25

This compound is a derivative of the GLP-1 analogue of SEQ ID NO: 3: N{Epsilon-36}-[2-[2-[2-[[2-[2-[2-[[(4S)-4-carboxy-4-[10-(3-carboxyphenoxy)decanoylamino]butan-oyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Derivative of SEQ ID NO: 3)

Chem. 45:

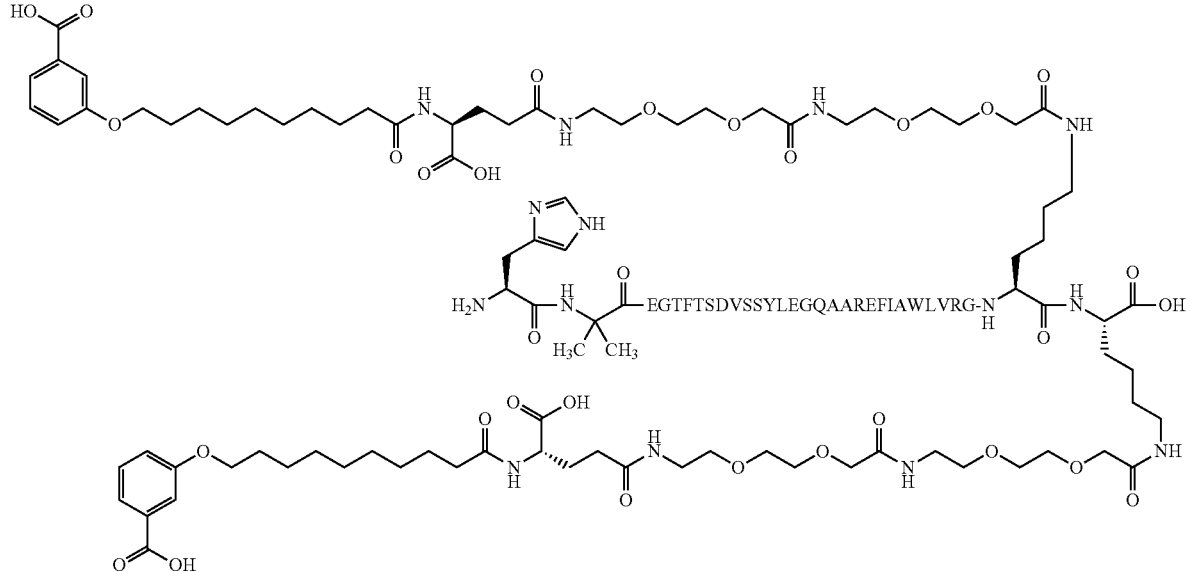

Preparation Method: SPPS_L; SC_L; CP_M1
LCMS_4: Rt=2.2 min m/z: m/5=979, m/4=1223
UPLC_B4_1: Rt=8.4 min Example 26

This compound is a derivative of the GLP-1 analogue of SEQ ID NO: 2: N{Epsilon-36}-[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Derivative of SEQ ID NO: 2)
Chem. 46:

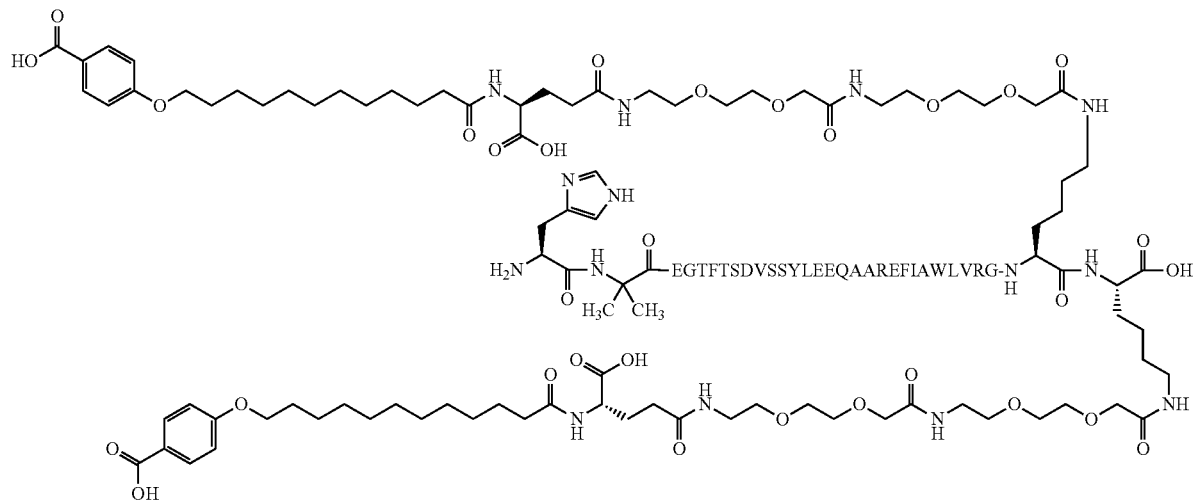

Preparation Method: SPPS_L; SC_L; CP_M1
LCMS_4: Rt=2.3 min m/z: m/3=1673, m/4=1255
UPLC_B4_1: Rt=9.0 min Example 27

This compound is a derivative of the GLP-1 analogue of SEQ ID NO: 6: N{Epsilon-36}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Aib8,Glu22,Arg26,Glu30,Arg34,Lys36,Lys37]-GLP-1-(7-37)-peptide (Derivative of SEQ ID NO: 6)
Chem. 47:

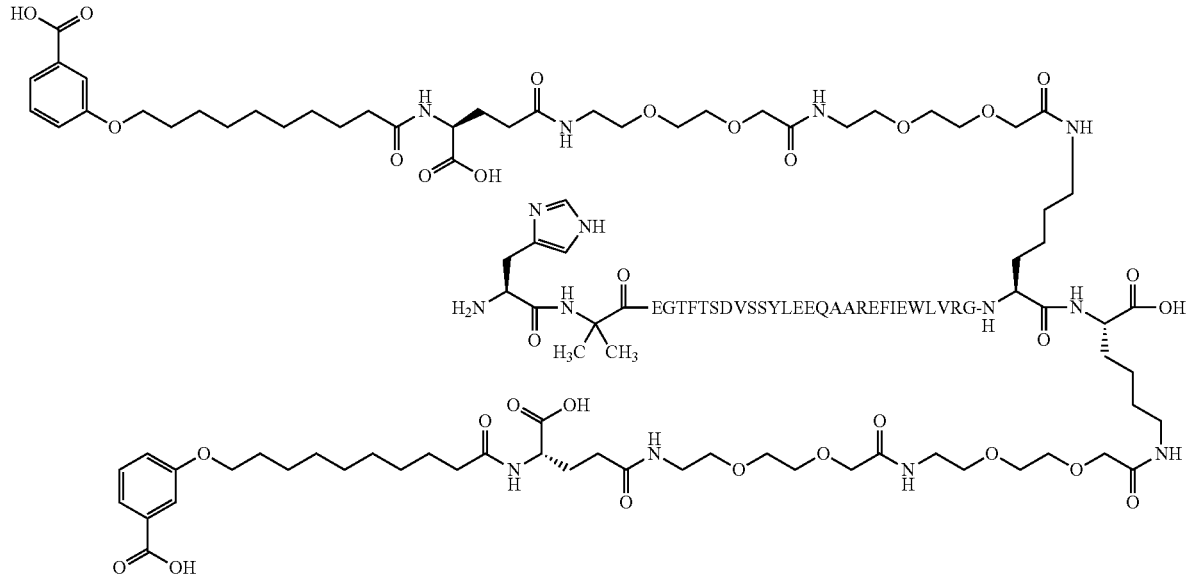

Preparation Method: SPPS_L; SC_L; CP_M1
LCMS_4: Rt=2.2 min m/z: m/4=1256, m/3=1674
UPLC_B4_1: Rt=8.5 min Example 28

This compound is a derivative of the GLP-1 analogue of SEQ ID NO: 6: N{Epsilon-36}-[2-[2-[2-[[2-[2-[2-[[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-37}-[2-[2-[2-[[2-[2-[2-[[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Glu30,Arg34,Lys36,Lys37]-GLP-1-(7-37)-peptide
(Derivative of SEQ ID NO: 6)
Chem. 48:

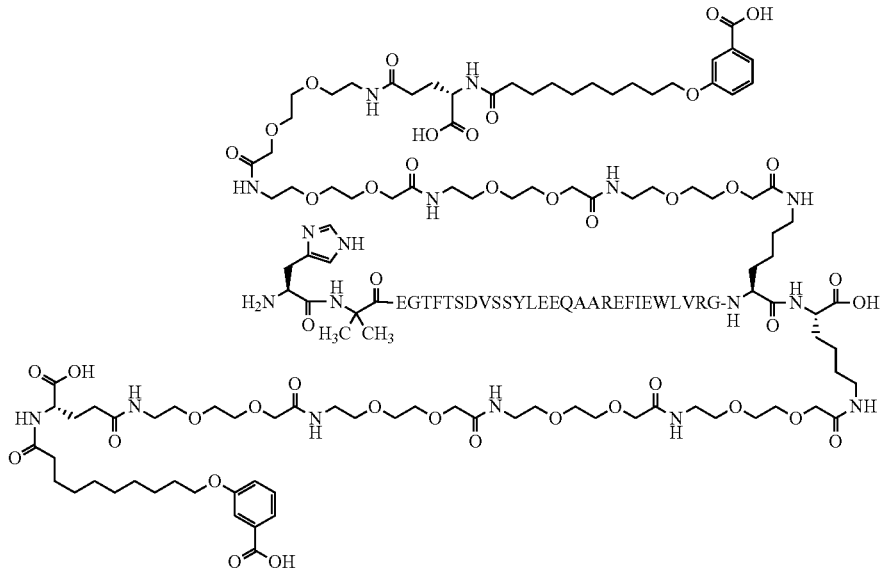

Preparation Method: SPPS_L; SC_L; CP_M1
LCMS_4: Rt=2.1 min m/z: m/5=1121, m/4=1401
UPLC_B4_1: Rt=8.3 min Pharmacological Methods Example 29: In Vitro Potency The purpose of this example is to test the activity, or potency, of the GLP-1 derivatives in vitro. The in vitro potency is the measure of human GLP-1 receptor activation in a whole cell assay.

The potencies of the GLP-1 derivatives of Examples 1-28 were determined as described below.

Principle

In vitro potency was determined by measuring the response of the human GLP-1 receptor in a reporter gene assay. The assay was performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

In order to test the binding of the derivatives to albumin, the assay was performed in the absence of serum albumin as well as in the presence of a considerably higher concentration of serum albumin (1.0% final assay concentration). An increase of the in vitro potency, $EC_{50}$ value, in the presence of serum albumin would indicate an affinity to serum albumin and represents a method to predict a protracted pharmacokinetic profile of the test substance in animal models.

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in Cell Culture Medium. They were aliquoted and stored in liquid nitrogen. Before each assay an aliquot is taken up and washed twice in PBS before being suspended at the desired concentration in the assay specific buffer. For 96-well plates the suspension was made to give a final concentration of $5 \times 10^3$ cells/well.

Materials

The following chemicals were used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Buffers

Cell Culture Medium consisted of DMEM medium with 10% FBS (Fetal Bovine Serum; Invitrogen 16140-071), 1 mg/ml G418 (Invitrogen 15140-122), 240 nM MTX (methotrexate; Sigma M9929) and 1% pen/strep (penicillin/streptomycin; Invitrogen 15140-122).

Assay Medium consisted of DMEM w/o phenol red, 10 mM Hepes and 1× Glutamax. The 1% Assay Buffer consisted of 2% ovalbumin, 0.2% Pluronic F-68 and 2% HSA in Assay Medium. The 0% Assay Buffer consisted of 2% ovalbumin and 0.2% Pluronic F-68 in Assay Medium.

Procedure

1) Cell stocks were thawed in a 37° C. water bath.
2) Cells were washed three times in PBS.
3) The cells were counted and adjusted to $5×10^3$ cells/50 μl ($1×10^5$ cells/ml) in Assay Medium. A 50 μl aliquot of cells was transferred to each well in the assay plate.
4) Stocks of the test compounds and reference compounds were diluted to a concentration of 0.2 pM in 0% Assay Buffer for the 0% HSA CRE luciferase assay and 1% Assay Buffer for the 1% HSA CRE luciferase assay. Compounds were diluted 10-fold to give the following concentrations: $2×10^{-7}$ M, $2×10^{-8}$ M; $2×10^{-9}$ M, $2×10^{-10}$ M, $2×10^{-11}$ M, $2×10^{-12}$ M, $2×10^{-13}$ M, and $2×10^{-14}$ M.
5) A 50 μl aliquot of compound or blank was transferred from the dilution plate to the assay plate. Compounds were tested at the following final concentrations: $1×10^{-7}$ M, $1×10^{-8}$ M; $1×10^{-9}$ M, $1×10^{-10}$ M, $1×10^{-11}$ M, $1×10^{-12}$ M, $1×10^{-13}$ M, and $1×10^{-14}$ M.
6) The assay plate was incubated for 3 h in a 5% $CO_2$ incubator at 37° C.
7) The assay plate was removed from the incubator and allowed to stand at room temperature for 15 min.
8) A 100 μl aliquot of steadylite plus reagent was added to each well of the assay plate (reagent was light sensitive).
9) Each assay plate was covered with aluminum foil to protect it from light and shaken for 30 min at room temperature.
10) Each assay plate was read in a Packard TopCount NXT instrument.

Calculations and Results

The data from the TopCount instrument were transferred to GraphPad Prism software. The software performs a non-linear regression (log(agonist) vs response). $EC_{50}$ values which were calculated by the software and reported in pM are shown in Table 1 below.

A minimum of two replicates was measured for each sample on separate assay plates. The reported values are averages of the duplicates. For some examples more than one assay was run and in this case the data reported are the averages of the averaged duplicates.

TABLE 1

| | In vitro potency | |
|---|---|---|
| Compound of Example no. | $EC_{50}$/pM (0% HSA) | $EC_{50}$/pM (1% HSA) |
| 1 | 1.2 | 136 |
| 2 | 3.1 | 122 |
| 3 | 1.2 | 28 |
| 4 | 1.9 | 21 |
| 5 | 1.1 | 22 |
| 6 | 1.8 | 15 |
| 7 | 1.5 | 143 |
| 8 | 1.5 | 37 |
| 9 | 2.2 | 16 |
| 10 | 1.7 | 33 |
| 11 | 1.5 | 80 |
| 12 | 1.2 | 10 |
| 13 | 1.3 | 18 |
| 14 | 2.3 | 60 |
| 15 | 6.1 | 44 |
| 16 | 1.6 | 104 |
| 17 | 14 | 199 |
| 18 | 0.8 | 29 |
| 19 | 2.1 | 31 |
| 20 | 2.7 | 5.8 |
| 21 | 5.6 | 13 |
| 22 | 1.8 | 7.7 |
| 23 | 7.7 | 15 |
| 24 | 8.1 | 8.6 |
| 25 | 19 | 64 |
| 26 | 1.5 | 124 |
| 27 | 13 | 105 |
| 28 | 12 | 25 |
| semaglutide | 8.3 | 265 |

All derivatives of the invention had a good in vitro potency corresponding to an $EC_{50}$ at 0% HSA of below 20 pM, and an $EC_{50}$ at 1.0% HSA of below 265 pM.

Example 30: GLP-1 Receptor Binding

The purpose of this example is to test the receptor binding activity of the GLP-1 derivatives in vitro. The receptor binding is a measure of affinity of a derivative for the human GLP-1 receptor.

Principle

The receptor binding of the GLP-1 derivatives of Examples 1-28 to the human GLP-1 receptor was measured in a competitive binding assay. In this type of assay a labelled ligand (in this case $^{125}$I-GLP-1) is bound to the receptor. Each derivative is added in a series of concentrations to isolated membranes containing the human GLP-1 receptor and displacement of the labelled ligand is monitored. The receptor binding is reported as the concentration at which half of the labelled ligand is displaced from the receptor, the $IC_{50}$ value. In order to test the binding of the derivatives to albumin, the assay is performed in a very low concentration of serum albumin (max. 0.001% final assay concentration as well as in the presence of a considerably higher concentration of serum albumin (2.0% final assay concentration). An increase of the $IC_{50}$ value in the presence of serum albumin indicates an affinity to serum albumin and represents a method to predict a protracted pharmacokinetic profile of the test substance in animal models.

Materials

The following chemicals were used in the assay: Human serum albumin (HSA) (Sigma A1653), DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, $MgCl_2$ (Merck 1.05832.1000), Tween 20 (Amresco 0850C335), SPA particles (wheat germ agglutinin (WGA) SPA beads, Perkin Elmer RPNQ0001), [$^{125}$I]-GLP-1]-(7-36)$NH_2$ (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM $MgCl_2$, 0.005% Tween 20 and pH was adjusted to 7.4. An 8% albumin stock consisted of HSA dissolved at 8% (w/v) in assay buffer. An 0.02% albumin stock consisted of HSA dissolved at 0.02% (w/v) in assay buffer.

Cell Culture and Membrane Preparation

The cells used in this assay (clone FCW467-12A) were BHK cells with BHKTS13 as a parent cell line. The cells express the human GLP-1 receptor.

The cells were grown at 5% $CO_2$ in DMEM, 10% fetal calf serum, 1% Pen/Strep (Penicillin/Streptomycin) and 1.0 mg/ml of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX™ dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay in the presence of low HSA (0.001%) 50 μl of the assay buffer was added to each well of an assay plate. Assay continued with step 3.
2. For the receptor binding assay in the presence of high HSA (2.0%) 50 μl of the 8% albumin stock was added to each well of an assay plate. Assay continued with step 3.
3. Test compounds were serially diluted to give the following concentrations: $8 \times 10^{-7}$ M, $8 \times 10^{-8}$ M, $8 \times 10^{-9}$ M, $8 \times 10^{-10}$ M, $8 \times 10^{-11}$ M, $8 \times 10^{-12}$ M and $8 \times 10^{-13}$ M. Twenty-five μl were added to appropriate wells in the assay plate.
4. Cell membrane aliquots were thawed and diluted to their working concentration. Fifty μl were added to each well in the assay plate.
5. WGA SPA beads were suspended in assay buffer at 20 mg/ml. The suspension was diluted to 10 mg/ml in assay buffer just prior to addition to the assay plate. Fifty μl were added to each well in the assay plate.
6. The incubation was started by adding 25 μl of 480 pM solution of [$^{125}$I]-GLP-1]-(7-36)NH$_2$ to each well of the assay plate. A 25 μl aliquot was reserved for measuring total counts/well.
7. The assay plate was incubated for 2 h at 30° C.
8. The assay plate was centrifuged for 10 min.
9. The assay plate was read in a Packard TopCount NXT instrument.

Calculations

The data from the TopCount instrument were transferred to GraphPad Prism software. The software averaged the values for the replicates and performed a non-linear regression. $IC_{50}$ values were calculated by the software and reported in nM.

Results

The following results were obtained:

TABLE 2

| GLP-1 receptor binding | | |
| --- | --- | --- |
| Compound of Example no. | $IC_{50}$/nM (low HSA) | $IC_{50}$/nM (high HSA) |
| 1 | 0.21 | 135 |
| 2 | 0.27 | 37 |
| 3 | 0.19 | 77 |
| 4 | 0.34 | 34 |
| 5 | 0.20 | 144 |
| 6 | 0.46 | 17 |

TABLE 2-continued

| GLP-1 receptor binding | | |
| --- | --- | --- |
| Compound of Example no. | $IC_{50}$/nM (low HSA) | $IC_{50}$/nM (high HSA) |
| 7 | 0.47 | 233 |
| 8 | 0.28 | 63 |
| 9 | 0.64 | 118 |
| 10 | 0.34 | 72 |
| 11 | 0.23 | 214 |
| 12 | 0.20 | 70 |
| 13 | 0.47 | 201 |
| 14 | 0.43 | 24 |
| 15 | 0.38 | 126 |
| 16 | 0.46 | 147 |
| 17 | 0.90 | 536 |
| 18 | 0.19 | 35 |
| 19 | 1.1 | 54 |
| 20 | 0.81 | 35 |
| 21 | 0.42 | 89 |
| 22 | 0.64 | 45 |
| 23 | 0.29 | 193 |
| 24 | 2.0 | 41 |
| 25 | 0.56 | 394 |
| 26 | 0.29 | 360 |
| 27 | 0.66 | 478 |
| 28 | 1.1 | 173 |
| semaglutide | 0.59 | 411 |

All derivatives of the invention had an $IC_{50}$ (low albumin) below 2.1 nM. As regards $IC_{50}$ (high albumin), all derivatives had an $IC_{50}$ (high albumin) below 540 nM.

Example 31: Pharmacokinetic Study in Mini Pigs

The purpose of this study is to determine the protraction in vivo of the GLP-1 derivatives after i.v. administration to mini pigs, i.e. the prolongation of their time in the body and thereby their time of action. This was done in pharmacokinetic (PK) studies, where the terminal half-life of the derivative in question was determined. By terminal half-life is generally meant the period of time it takes to halve a certain plasma concentration, measured after the initial distribution phase.

The derivatives of Examples 1, 2, 3, 5, 7, 8, 12, 13, 14, 15, and 16 were subjected to PK study (see below).

Female Göttingen mini pigs obtained from Ellegaard Göttingen Minipigs (Dalmose, Denmark) at approximately 5 months of age and weighing approximately 10 kg were used in the studies. The mini pigs were housed in pens with straw as bedding, four to six together in each pen and fed restrictedly once or twice daily with Altromin 9023 mini pig diet (Chr. Petersen A/S, DK-4100 Ringsted). The pigs were used for repeated pharmacokinetic studies with a suitable wash-out period between successive GLP-1 derivative dosings. An acclimatisation period of 1 week was allowed during which time the mini pigs were trained to be fixated on the back for blood sampling and in slings for i.v. dosing. All handling, dosing and blood sampling of the animals was performed by trained and skilled staff.

The GLP-1 derivatives were dissolved in 50 mM sodium phosphate, 70 mM sodium chloride, 0.05% tween 80, pH 7.4 to a concentration of approximately 20 nmol/ml. Intravenous injections (the volume corresponding to usually 2 nmol/kg, for example 0.1 ml/kg) of the compounds were given as intravenous injections via a Venflon inserted in an ear vein, while the animals were placed un-anaesthetised in a sling. The dose volume was 0.1 ml/kg, and blood was sampled at predefined time points for up till 13 days post dosing (samples were taken with a syringe from a jugular vein). Blood samples (for example 0.8 ml) were collected in EDTA buffer (8 mM) and then centrifuged at 4° C. and 2000 G for 10 minutes.

Sampling and Analysis:

Plasma was pipetted into Micronic tubes on dry ice, and kept at −20° C. until analysed for plasma concentration of the respective GLP-1 compound using ELISA or a similar antibody based assay such as LOCI, or LC-MS. Individual plasma concentration-time profiles were analysed by a non-compartmental model in WinNonlin v. 5.0 or Phoenix v. 6.2 or 6.3 (Pharsight Inc., Mountain View, Calif., USA), or other relevant software for PK analysis, and the resulting terminal half-lives determined.

Results

The following results were obtained:

TABLE 3

In vivo studies in Gottingen mini pigs after intravenous administration

| Compound of Example no. | Minipig iv PK, t½ (hours)* |
|---|---|
| 1 | 103 |
| 2 | 74 |
| 3 | 71 |
| 5 | 99 |
| 7 | 107 |
| 8 | 88 |
| 12 | 80 |
| 13 | 98 |
| 14 | 90 |
| 15 | 144 |
| 16 | 80 |

*terminal half-life (t½) is harmonic mean, n = 3

The results show an impressive half-life of up to 144 hours. For comparison the average half-life of semaglutide in mini pigs after intravenous administration is 55 hours (average of two separate studies, total n=12).

Example 32: Pharmacokinetic Studies in Beagle Dogs

Pharmacokinetic (PK) studies in Beagle dogs were conducted in order to determine a) the protraction of the GLP-1 derivatives after i.v. administration, and b) the bioavailability of the GLP-1 derivatives after p.o. administration.

By protraction is meant the prolongation of the time in the body and thereby the time of action of the GLP-1 derivatives. This was done in pharmacokinetic (PK) studies, where the terminal half-life of the derivative in question was determined. By terminal half-life is generally meant the period of time it takes to halve a certain plasma concentration, measured after the initial distribution phase.

The GLP-1 derivatives of Examples 1, 2, 8, and 15 were subjected to PK studies as described below.

For the studies with the GLP-1 derivatives of Examples 1 and 2 female and male Beagle dogs (50:50) were used, 21 to 30 months of age and weighing approximately 10-12 kg at the start of the studies. The dogs were housed in pens (12 hours light: 12 hours dark) with softwood based granules as bedding, two together in each pen and fed restrictedly once daily with SPECIFIC™ Struvite Management Diet (Dechra Veterinary Products, UK). Exercise was permitted daily, whenever possible. The dogs were used for repeated pharmacokinetic studies with a suitable wash-out period between successive GLP-1 derivative dosings. An acclimatisation period of 4 weeks was allowed during which time the dogs were trained. All handling, dosing and blood sampling of the animals was performed by trained and skilled staff. The dogs were fasted overnight before dosing and from 0 to 4 h after dosing, but had ad libitum access to water during the whole period.

For the studies with the compounds of Examples 8 and 15 and for further studies with the compound of Example 2 (for the determination of bioavailability p.o.) the Beagle dogs were 1 to 5 years of age and weighing approximately 10-12 kg at the start of the studies. The dogs were housed in social groups (12 hours light: 12 hours dark), and fed individually and restrictedly once daily with Royal Canin Medium Adult dog (Royal Canin Products, China Branch, or Brogaarden A/S, Denmark). Exercise and group social was permitted daily, whenever possible. The dogs were used for repeated pharmacokinetic studies with a suitable wash-out period between successive GLP-1 derivative dosings. An appropriate acclimatisation period was given prior to initiation of the first pharmacokinetic study. All handling, dosing and blood sampling of the animals was performed by trained and skilled staff. Before the studies the dogs were fasted overnight and from 0 to 4 h after dosing. Besides, the dogs were restricted to water 1 hour before dosing until 4 hours after dosing, but otherwise had ad libitum access to water during the whole period.

Peroral (p.o.) Administration of Tablets

The GLP-1 tablets used for the p.o. studies were enteric coated tablets which contained a sodium caprate core with approximately 10 mg of the GLP-1 derivative, prepared and composed as described in Example 33.

The tablets containing the GLP-1 derivative were administered in the following manner: Gastric acid secretion was induced by subcutaneous administration in the neck of pentagastrin at a dose of approximately 4 μg/kg body weight (120 μg/mL) 20 minutes prior to oral administration of the tablet.

The tablet was placed in the back of the mouth of the dog in order to prevent chewing. The mouth was then closed and 10 mL of tap water was given by a syringe to facilitate swallowing of the tablet.

Intravenous Administration

In the i.v. studies, the GLP-1 derivatives, dissolved in 50 mM sodium phosphate, 70 mM sodium chloride, 70 ppm Polysorbate 20, pH 7.4 to a concentration of approximately 20 nmol/ml, were administered to the dogs by intravenous injections (the volume corresponding to usually 2 nmol/kg, for example 0.1 ml/kg) in the cephalic or saphenous vein. The dose volume was 0.1 ml/kg.

Blood Sampling

Blood was sampled at predefined time points for up till 10-12 days post dosing to adequately cover the full plasma concentration-time profile of the GLP-1 derivative.

For each blood sampling time point approximately 0.8 mL of whole blood was collected in a 1.5 mL EDTA coated tube, and the tube was gently turned to allowing mixing of the sample with the anticoagulant. Blood samples (for example 0.8 ml) were collected in EDTA buffer (8 mM) and then centrifuged at 4° C. and 2000 G for 10 minutes. Plasma was pipetted into Micronic tubes on dry ice, and kept at −20° C. until analysis.

Blood samples were taken as appropriate, for example a) from the jugular vein using a standard 21G needle and a syringe, or b) from a venflon in the cephalic vein in the front leg for the first 2 hours and then with syringe from the jugular vein for the rest of the time points (the first few drops were allowed to drain from the venflon to avoid heparin saline from the venflon in the sample).

Analysis

The plasma concentration of the respective GLP-1 derivative was analysed using ELISA or a similar antibody based assay such as LOCI, or LC-MS. Individual plasma concentration-time profiles were analysed by a non-compartmental model in WinNonlin v. 5.0 or Phoenix v. 6.2 or 6.3 (Pharsight Inc., Mountain View, Calif., USA), or other relevant software for PK analysis.

The resulting terminal half-lives were determined based on the i.v. studies.

The absolute bioavailability (F) was calculated as follows:

The area under the plasma concentration versus time curve (AUC, [time×concentration]) was calculated (by the Pharsight programme) after both oral administration and intravenous administration, typically until 240-288 hours post dosing, or until last measured concentration.

The absolute bioavailability (F) was then calculated based on the dose-corrected AUC values, namely as $AUC/D_{po}$ divided by $AUC/D_{iv}$, where $D_{po}$ is the expected oral dose per kg, calculated based on the amount dosed (a typical tablet contains approximately 10 mg of the GLP-1 derivative), and $D_{iv}$ is the dose per kg given intravenously.

Results

The following results were obtained:

TABLE 4

In vivo pharmacokinetic evaluation in Beagle dogs after intravenous administration

| GLP-1 derivative of Example no. | Beagle dogs iv PK, t½ (hours)* |
| --- | --- |
| 1 | 85 |
| 2 | 77** |
| 8 | 119 |
| 15 | 111 |

*terminal half-life (t½) is harmonic mean, n = 4
**average of two separate studies The results show an impressive half-life of up to 119 hours. For comparison the average half-life of semaglutide in Beagle dogs after intravenous administration is 55 hours (average of seven separate studies, total n=30).

TABLE 5

In vivo pharmacokinetic evaluation in Beagle dogs after per oral administration

| Tablet with GLP-derivative of Example no. | Beagle dogs p.o. bioavailability (%) |
| --- | --- |
| 1 | 2.4 |
| 2 | 3.4 |

The bioavailabilities reported in Table 5 are significantly higher than seen for semaglutide in Beagle dog studies with the same tablet compositions (same except for the active pharmaceutical ingredient).

Example 33: Preparation and Composition of Oral GLP-1 Tablets

This example describes the manufacture of tablets of the GLP-1 derivatives of Examples 1 and 2.

The Example 1 tablet comprises a tablet core, a Pharmacoat sub-coat, and an 80:20 FS30D:L30D-55 enteric coating, and was prepared using methods 1, 2c, and 3b described below. The tablet contains 10 mg of the active pharmaceutical ingredient of Example 1. The final composition of the Example 1 tablet is shown in Table 6 below. The tablet core weight was 710 mg, and the weight of the enteric coated tablet with sub-coat was 771.1 mg.

The Example 2 tablet comprises a tablet core, an Opadry Clear sub-coat, and an 80:20 FS30D:L30D-55 enteric coating, and was prepared using methods 1, 2a, and 3b described below. The tablet contains 10 mg of the active pharmaceutical ingredient of Example 2. The final composition of the Example 2 tablet is shown in Table 7 below. The tablet core weight was 710 mg, the weight of the enteric coated tablet with sub-coat was 771.1 mg.

Materials

Eudragit® FS 30 D, Eudragit® L 30 D-55, Plasacryl™ T20 were used as sold by Evonik Industries, Essen, Germany in 2014. Opadry® Clear 03K19229, and Opadry® White 03F180011 were used as sold by Colorcon, PA, USA, 2014. Pharmacoat® 603 was used as sold by Shin-Etsu Ltd., Tokyo, Japan, in 2014.

Preparation of Tablet Core (Method 1)

Tablet core material with the following composition:

| a) GLP-1 derivative | 1.41% w/w, |
| --- | --- |
| b) sodium caprate | 77.46% w/w, |
| c) sorbitol | 20.63% w/w, and |
| d) stearic acid | 0.50% w/w | was manufactured as follows:

The correct amount of GLP-1 was weighed. Sorbitol powder was sieved using a mesh size of 0.5 mm followed by weighing the correct amount of sorbitol.

GLP-1 and sorbitol were mixed in a small container. An amount of sorbitol equivalent to the amount of GLP-1 was added to the container and mixed by hand. Then the double amount of sorbitol relative to the previous addition was added and mixed by hand until GLP-1 and all sorbitol were mixed well. This step was followed by a mechanical mixing in a Turbula-mixer to finalize the mixing to obtain a homogeneous blend consisting of GLP-1 and sorbitol.

Sodium caprate (in the form of granulate) was then added to the blend consisting of GLP-1 and sorbitol according to the equal volumes principle. A granulate of sodium caprate may be prepared by granulation. This was done in two steps and finalized with a mechanical mixing step in a Turbula-mixer resulting in a blend consisting of GLP-1, sorbitol, and sodium caprate.

Finally, stearic acid was sieved using a mesh size of 0.3 mm followed by weighing of the correct amount of stearic acid, and addition hereof to the blend consisting of GLP-1, sorbitol, and sodium caprate and mixed mechanically resulting in the final granulate.

The final granulate was then compressed in a tablet press to form tablets of a mass of 710 mg, unless otherwise stated herein, via a standard tabletting process, for example using a Fette 1021 tablet press. Tablets were produced to a technical level allowing for further processing such as e.g. coating.

Adding Sub-Coat to Tablet Core

Method 2a—Opadry® Clear 03K19229

A tablet core prepared by Method 1 was coated with a sub-coat comprising Opadry® Clear 03K19229. The coating suspension was prepared by a) adding 6 g Opadry® Clear 03K19229 coating material (polymer powder) into 94 g demineralised water under intense mixing using a standard magnetic stirrer, following by b) stirring at low intensity for 45 minutes, and finally c) sieving the suspension to remove lumps. Coating of tablet cores was performed in a pan coater with the pan size of 8.5", with a conventional patterned air Schlick spray nozzle with an orifice of 1.0 mm, an atomizing and pattern air pressure of 0.55 bar, inlet air temperature of 40° C. and air flow of 100 kg/hour. After addition of the required amount of coating suspension (1.4% w/w dry weight of the polymer powder, see Table 7) distributed evenly on the tablet cores the spraying was stopped and the tablets dried for up to 30 minutes inside the pan.

Method 2c—Pharmacoat® 603

A tablet core prepared by Method 1 was coated with a sub-coat comprising Pharmacoat® 603. The coating suspension was prepared by a) wetting 10 g Pharmacoat® 603 with 90 g boiled water while stirring with a spoon b) dissolving 2 g triacetin in 112 g demineralised water and adding it to the Pharmacoat® 603 hypromellose suspension, followed by c) stirring at low intensity for up to 45 min. Then d) adding 0.9 g Talc to the suspension, and finally e) homogenization the suspension for at least 15 min. Coating of tablet cores was performed using same equipment and conditions as described for Method 2a. After addition of the required amount of coating suspension (1.4% w/w dry weight of the Pharmacoat® hypromellose coating material, see Table 6) distributed evenly on the tablets the spraying was stopped and the tablets dried for up to 30 minutes inside the pan.

Adding Enteric Coating (Method 3b—Combination of Eudragit® FS30 D and Eudragit® L 30 D-55)

An anionic copolymer coating was applied on a tablet core coated with a sub-coat prepared according to Method 1 and Method 2a, according to the following method:

17.4 g PlasAcryl™T20 was mixed with 20.0 g demineralised water for 5 min while stirring. 1.7 g triethylcitrate was mixed with 44.9 g demineralised water for 5 min and then added to PlasAcryl™T20. 92.8 g of an aqueous dispersion of Eudragit® FS 30 D coating material was placed in a beaker on a suitable stirring apparatus. The PlasAcryl™ T20 suspension and 23.2 g L 30D-55 coating material were added to the FS30D suspension while stirring for at least 10 min prior to filtration through a 0.24 mm mesh filter to remove lumps resulting in the coating suspension. The amounts of Eudragit® FS 30 D and Eudragit® L 30 D-55 described here results in a 80:20 ratio between Eudragit® FS 30 D and Eudragit® L 30 D-55.

Coating with the coating suspension was performed in a pan coater with the pan size of 8.5", with a conventional patterned air Schlick spray nozzle with an orifice of 1.0 mm, an atomizing and pattern air pressure of 0.5-0.7 bar, inlet air temperature of 37° C., air flow of 100 kg/hours. After addition of the required amount of coating suspension (6.4% w/w dry weight of the combination of Eudragit® FS 30 D and Eudragit® L 30 D-55 coating materials, see Table 7) distributed evenly on the tablets, the spraying was stopped and the tablets dried for up to 30 minutes inside the pan.

TABLE 6

Composition of Example 1 tablet

| Tablet component | Amount per tablet (mg) | Concentration in tablet core (% w/w) | Concentration in final coated tablet (% w/w) | Location in the tablet | Function |
|---|---|---|---|---|---|
| GLP-1 derivative of Example 1 (API) | 10 | 1.4 | 1.3 | Tablet core | GLP-1 agonist |
| Sodium caprate | 550 | 77.5 | 71.3 | Tablet core | Permeation enhancer |
| Parteck SI 150 (Sorbitol) | 146.4 | 20.6 | 19.0 | Tablet core | Filler |
| Stearic Acid | 3.6 | 0.5 | 0.5 | Tablet core | Lubricant |
| Pharmacoat | 10.7 | N/A | 1.4 | Between tablet core and enteric coat | Sub-coat |
| 80:20 FS30D:L30D-55 | 50.4 | N/A | 6.5 | Surrounding the sub-coat | Enteric coat |

TABLE 7

Composition of Example 2 tablet

| Tablet component | Amount per tablet (mg) | Concentration in tablet core (% w/w) | Concentration in final coated tablet (% w/w) | Location in the tablet | Function |
|---|---|---|---|---|---|
| GLP-1 derivative of Example 2 (API) | 10 | 1.4 | 1.3 | Tablet core | GLP-1 agonist |
| Sodium caprate | 550 | 77.5 | 71.3 | Tablet core | Permeation enhancer |
| Parteck SI 150 (Sorbitol) | 146.4 | 20.6 | 19.0 | Tablet core | Filler |

TABLE 7-continued

Composition of Example 2 tablet

| Tablet component | Amount per tablet (mg) | Concentration in tablet core (% w/w) | Concentration in final coated tablet (% w/w) | Location in the tablet | Function |
|---|---|---|---|---|---|
| Stearic Acid | 3.6 | 0.5 | 0.5 | Tablet core | Lubricant |
| Opadry Clear | 10.7 | N/A | 1.4 | Between tablet core and enteric coat | Sub-coat |
| 80:20 FS30D:L30D-55 | 50.4 | N/A | 6.45 | Surrounding the sub-coat | Enteric coat |

Example 34: Pharmacodynamic (PD) Study in Pigs

The purpose of this experiment is to investigate the effect of the GLP-1 derivatives on food intake in pigs. This was done in a pharmacodynamic (PD) study as described below, in which food intake was measured from 1 to 4 days after administration of a single dose of the GLP-1 derivative, as compared to a vehicle-treated control group.

Female Landrace Yorkshire Duroc (LYD) pigs or Large White hybrid, approximately 3 months of age, weighing approximately 30-35 kg were used (n=3-4 per group). The animals were housed in a group for approximately 1 week during acclimatisation to the animal facilities. During the experimental period the animals were placed in individual pens at least 2 days before dosing and during the entire experiment for measurement of individual food intake.

The animals were fed ad libitum with pig fodder (Svinefoder Danish Top or HRC Sow and Weaner Diet) at all times both during the acclimatisation and the experimental period. Food intake was monitored on line by logging the weight of fodder every 15 minutes using the Mpigwin system (Ellegaard Systems, Faaborg, Denmark). Alternatively fodder was offered in the morning each day, and availability for the full 24-hour period was ensured. Any uneaten fodder was removed and weighed (manually) on the following morning, and replaced with fresh fodder.

The GLP-1 derivatives were dissolved in a phosphate buffer (50 mM sodium phosphate, 70 mM sodium chloride, 0.05% tween 80, pH 7.4) at concentrations of approximately 120 nmol/ml corresponding to doses of 3 nmol/kg. The phosphate buffer served as vehicle.

Animals were dosed with a single subcutaneous dose of the GLP-1 derivative or vehicle (dose volume 0.025 ml/kg) on the morning of day 1, and food intake was measured for 2-4 days after dosing. On the last day of each study, 2 or 4 days after dosing, a blood sample for measurement of plasma exposure of the GLP-1 derivative was taken from the heart in anaesthetised animals. The animals were thereafter euthanised with an intra-cardial overdose of pentobarbitone.

If desired, plasma content of the GLP-1 derivatives was analysed using ELISA or a similar antibody based assay or LC-MS.

Food intake was calculated in 24 h intervals (0-24 h, 24-48 h, 48-72 h and 72-96 h). In Table 8 below the resulting mean food intake is indicated as percentage of the mean food intake of the vehicle group in the same time interval.

TABLE 8

Effect on food intake in pigs

| GLP-1 derivative of Example no. | PD in pig, food intake (% of vehicle) for hours (x-y) | | | |
|---|---|---|---|---|
| | 0-24 | 24-48 | 48-72 | 72-96 |
| 1 | 26 | 53 | — | — |
| 2 | 54 | $66^{NS}$ | — | — |
| 5 | 58 | $75^{NS}$ | — | — |
| 7 | $84^{NS}$ | $85^{NS}$ | — | — |
| 8 | $76^{NS}$ | $83^{NS}$ | — | — |
| 12 | 15 | 38 | — | — |
| 13 | 54 | $86^{NS}$ | — | — |
| 15 | 57 | 62 | $75^{NS}$ | $90^{NS}$ |
| 16 | $82^{NS}$ | $84^{NS}$ | — | — |
| 20 | 10 | 18 | 65 | $81^{NS}$ |

The data shows that a single s.c. injection of the tested GLP-1 derivatives in pigs caused a reduced food intake for up to 2-4 days after the injection. However, for the results marked with "NS" the reduction was not significantly different compared to the vehicle group, under the present testing conditions. The derivatives of Examples 12 and 20 showed the largest reduction in food intake (days 1 and 2).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a GLP-1 (7-37) analogue, wherein said analogue comprises a first Lys residue at a position corresponding to position 36 of GLP-1(7-37) (SEQ ID NO: 1), a second Lys residue at a position corresponding to position 37 of GLP-1(7-37) (SEQ ID NO: 1), and a maximum of seven amino acid changes as compared to GLP-1(7-37) (SEQ ID NO: 1); which derivative comprises two protractors attached to said first and second Lys residue, respectively, each via a linker; wherein the protractor is selected from:

HOOC—C$_6$H$_4$—O—(CH$_2$)$_y$—CO—*, and    Chem. 1:

HOOC—(CH$_2$)$_x$—CO—*,    Chem. 2:

wherein y is an integer in the range of 8-11, and x is 12; and the linker comprises at least one of:

*—NH—CH(COOH)—(CH$_2$)$_2$—CO—*,    Chem. 3:

*—NH—CH((CH$_2$)$_2$—COOH)—CO—*, and/or    Chem. 4:

*—NH—(CH$_2$)$_2$—[O—(CH$_2$)$_2$]$_k$—O—[CH$_2$]$_n$—CO—*,    Chem. 5:

wherein k is an integer in the range of 1-5, and n is an integer in the range of 1-5, and wherein the amino acid in position 31 of GLP-1(7-37) (SEQ ID NO: 1) is Trp; or a pharmaceutically acceptable salt, amide, or ester thereof.

2. The derivative of claim 1, wherein the linker comprises Chem. 5.

3. The derivative of claim 2, wherein k=n=1.

4. The derivative of claim 3, wherein Chem. 5 is included one, two, three, or four times.

5. The derivative of claim 1, wherein the linker comprises Chem. 3 or Chem. 4.

6. The derivative of claim 1, wherein the GLP-1 (7-37) analogue comprises the sequence of Formula I:

$Xaa_7$-$Xaa_8$-Glu-Gly-Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-Lys-Lys (SEQ ID NO: 7), wherein $Xaa_7$ is L-histidine, (S)-2-Hydroxy-3-(1H-imidazol-4-yl)-propionic acid, D-histidine, desamino-histidine (desH), $N^\alpha$-acetyl-histidine, $N^\alpha$-formyl-histidine;

$Xaa_8$ is Ala, Gly, Ser, Aib, (1-aminocyclopropyl) carboxylic acid, or (1-aminocyclobutyl) carboxylic acid;

$Xaa_{16}$ is Val or Leu;

$Xaa_{18}$ is Ser or Arg;

$Xaa_{19}$ is Tyr or Gln;

$Xaa_{20}$ is Leu or Met;

$Xaa_{22}$ is Gly or Glu;

$Xaa_{23}$ is Gln, Glu, or Arg;

$Xaa_{25}$ is Ala or Val;

$Xaa_{26}$ is Arg or Lys;

$Xaa_{27}$ is Glu or Leu;

$Xaa_{30}$ is Ala, or Glu;

$Xaa_{31}$ is Trp or His;

$Xaa_{33}$ is Val or Arg;

$Xaa_{34}$ is Arg, Lys, His, Asn, or Gln; and $Xaa_{35}$ is Gly or Aib.

7. A GLP-1 derivative selected from the following:

Chem. 21
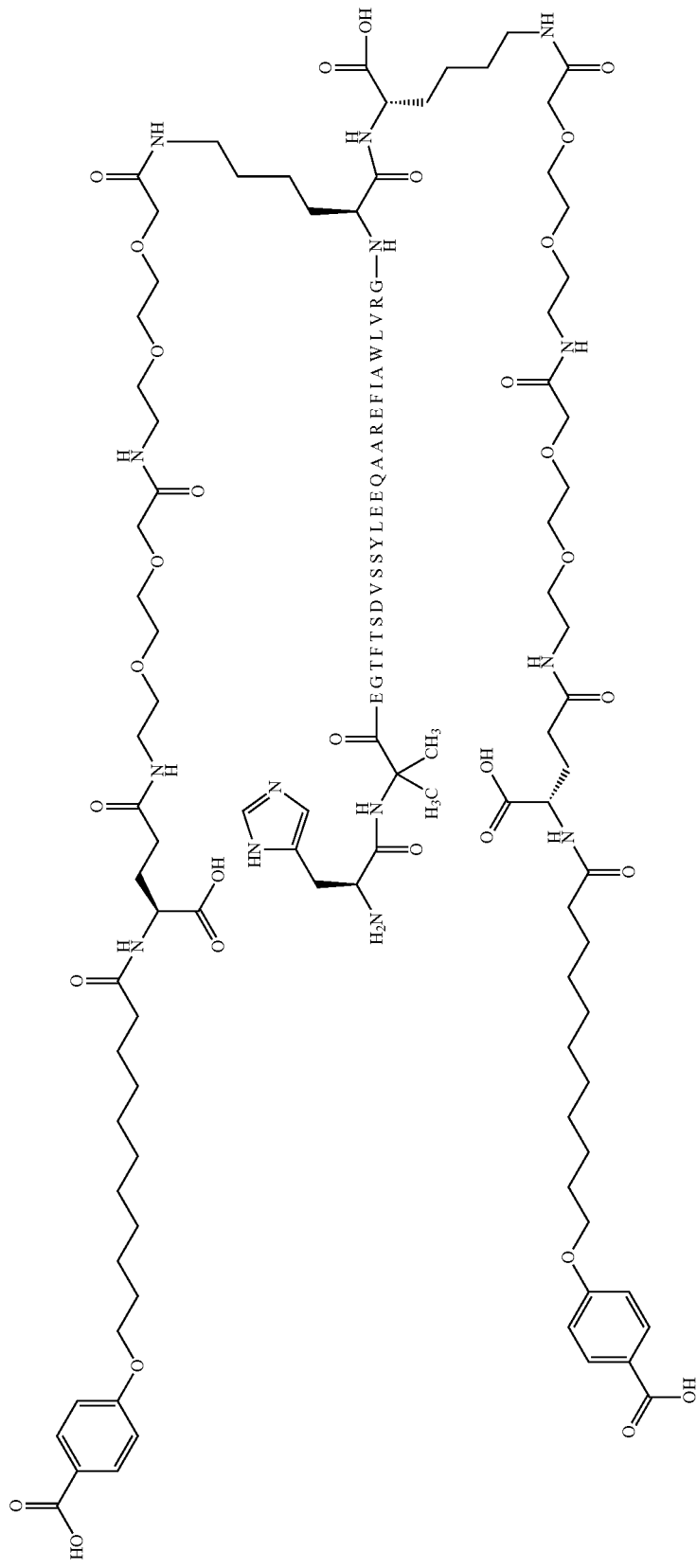

where the amino acid sequence is that of SEQ ID NO:2,
Chem. 22

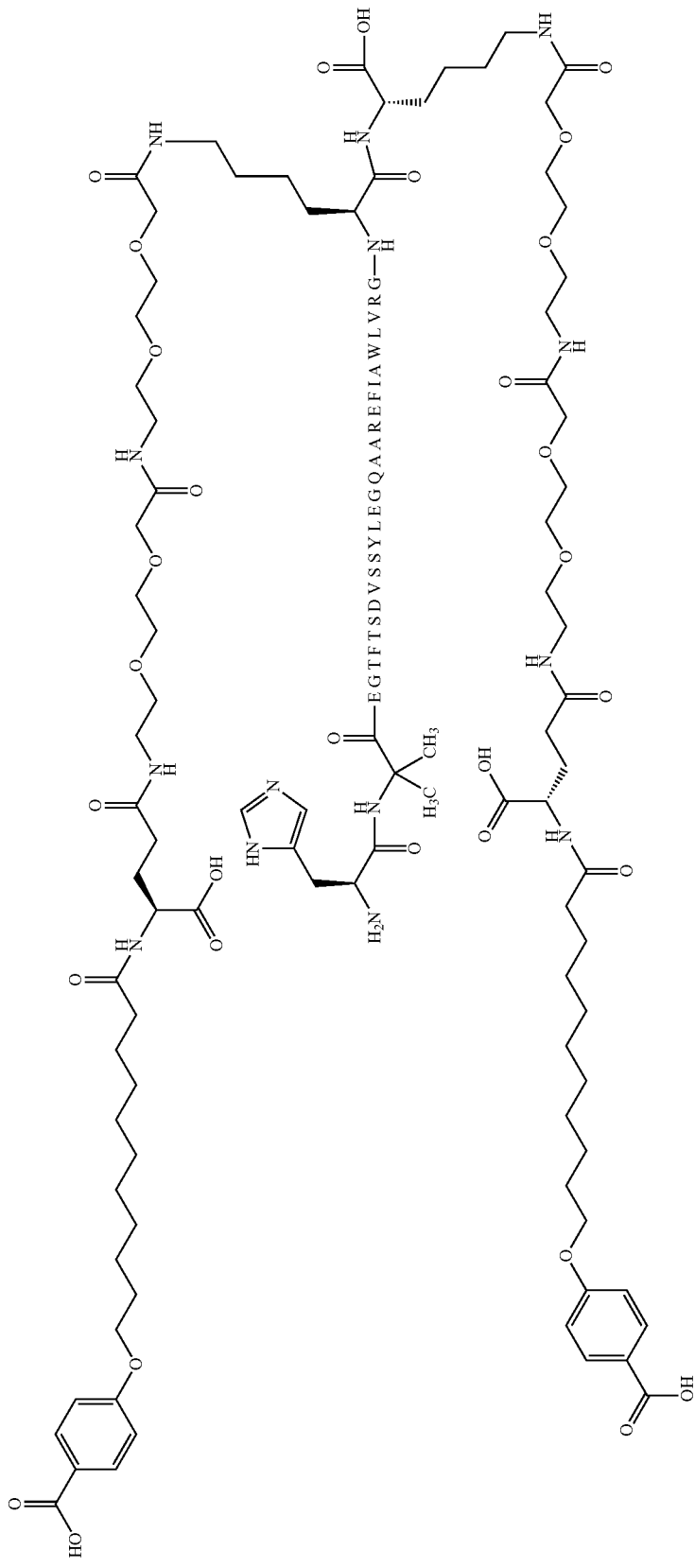

where the amino acid sequence is that of SEQ ID NO:3,
Chem. 23

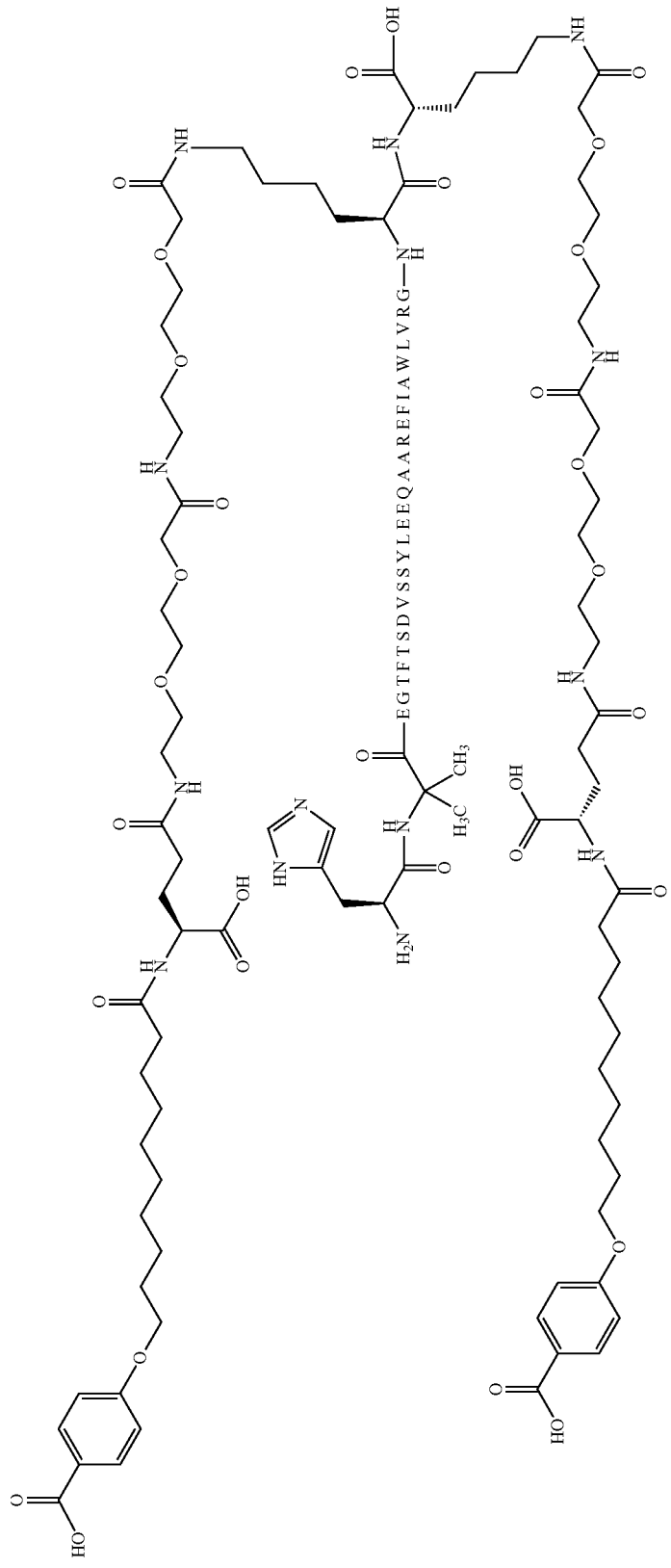

where the amino acid sequence is that of SEQ ID NO:2,
Chem. 24

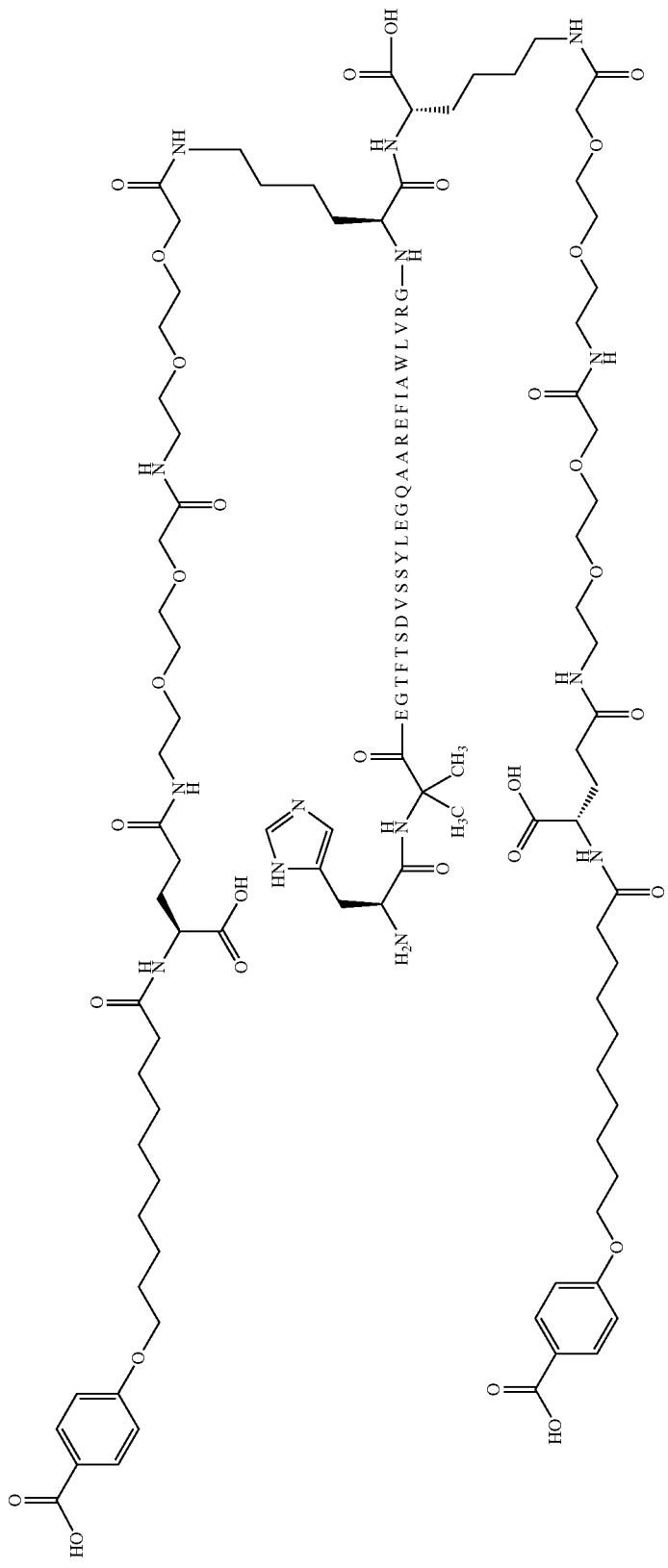

where the amino acid sequence is that of SEQ ID NO:3,
Chem. 25

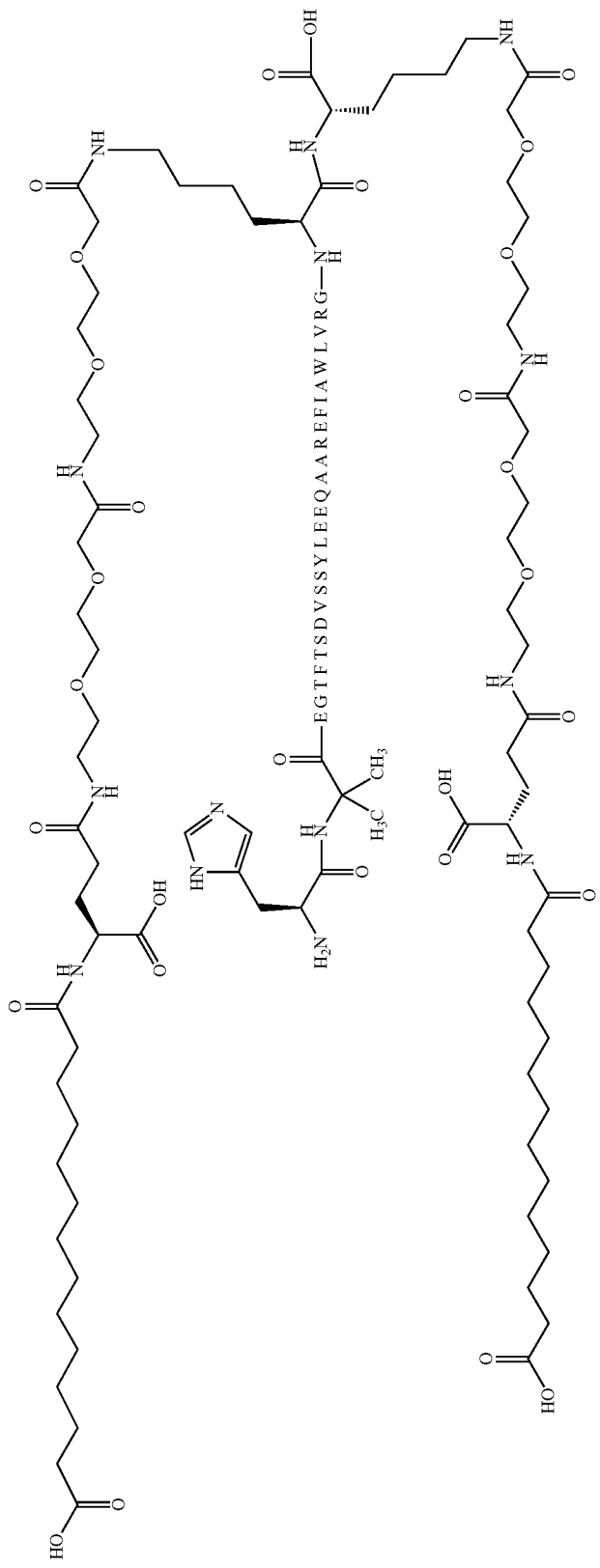

where the amino acid sequence is that of SEQ ID NO:2,
Chem. 26

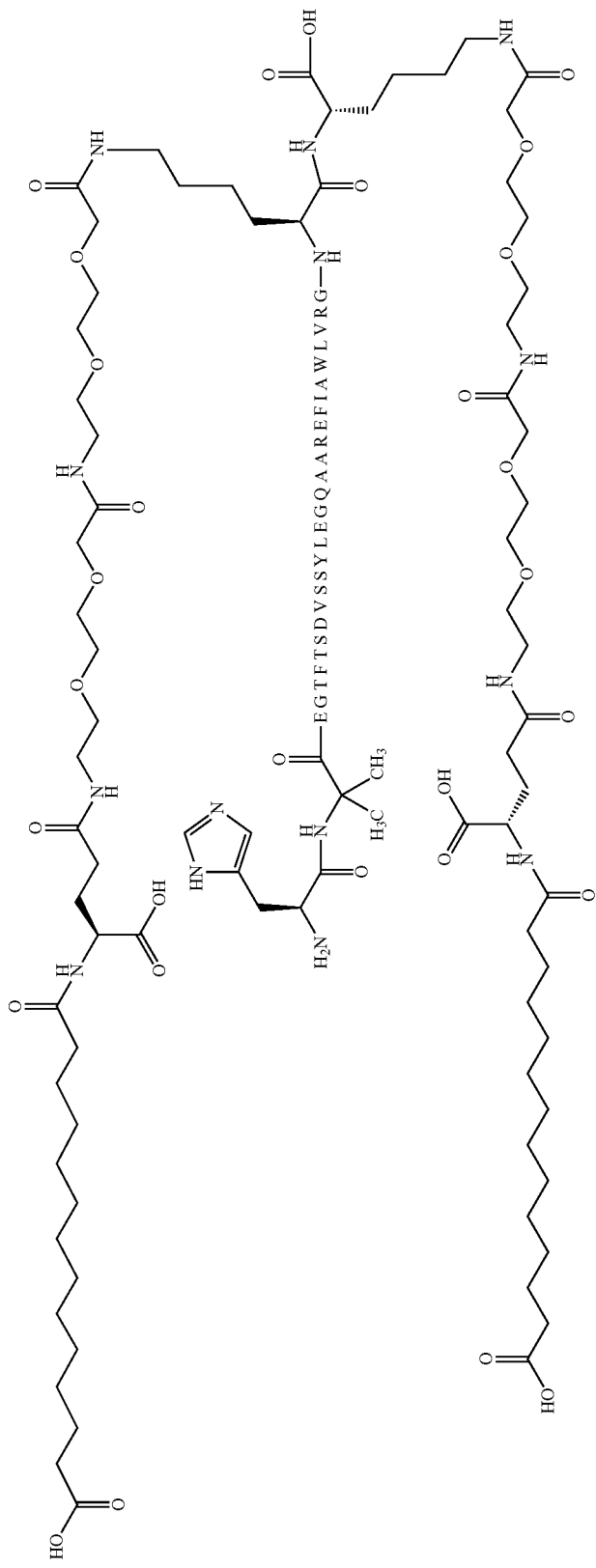

where the amino acid sequence is that of SEQ ID NO:3,
Chem. 27

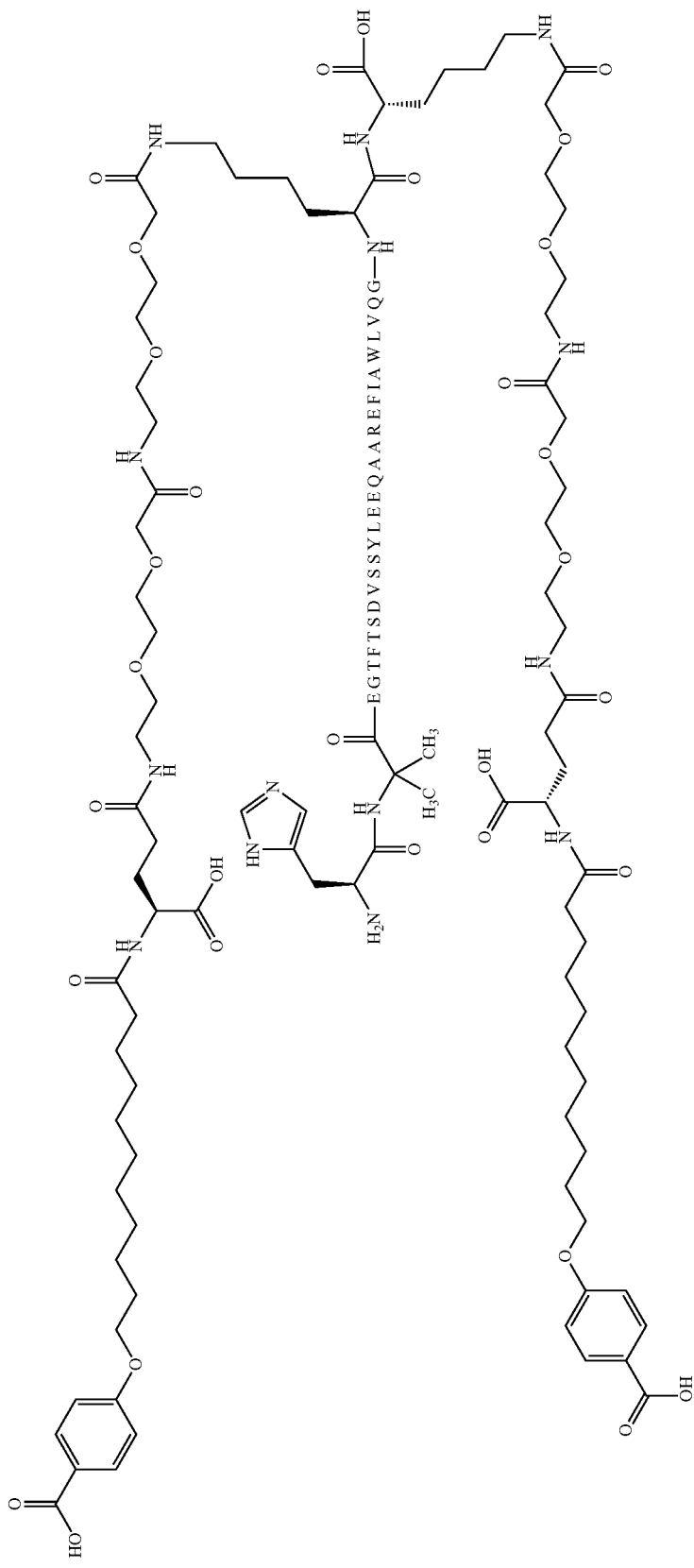

where the amino acid sequence is that of SEQ ID NO:4,
Chem. 28

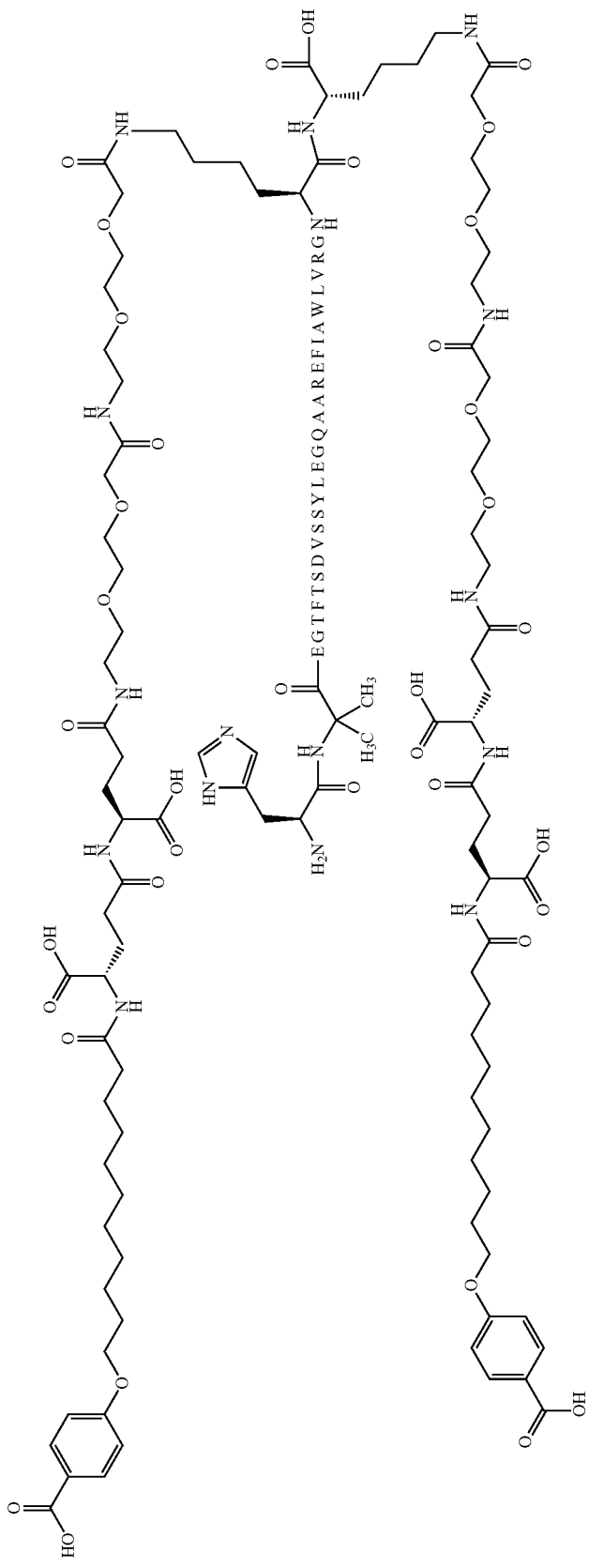

where the amino acid sequence is that of SEQ ID NO:3,
Chem. 29

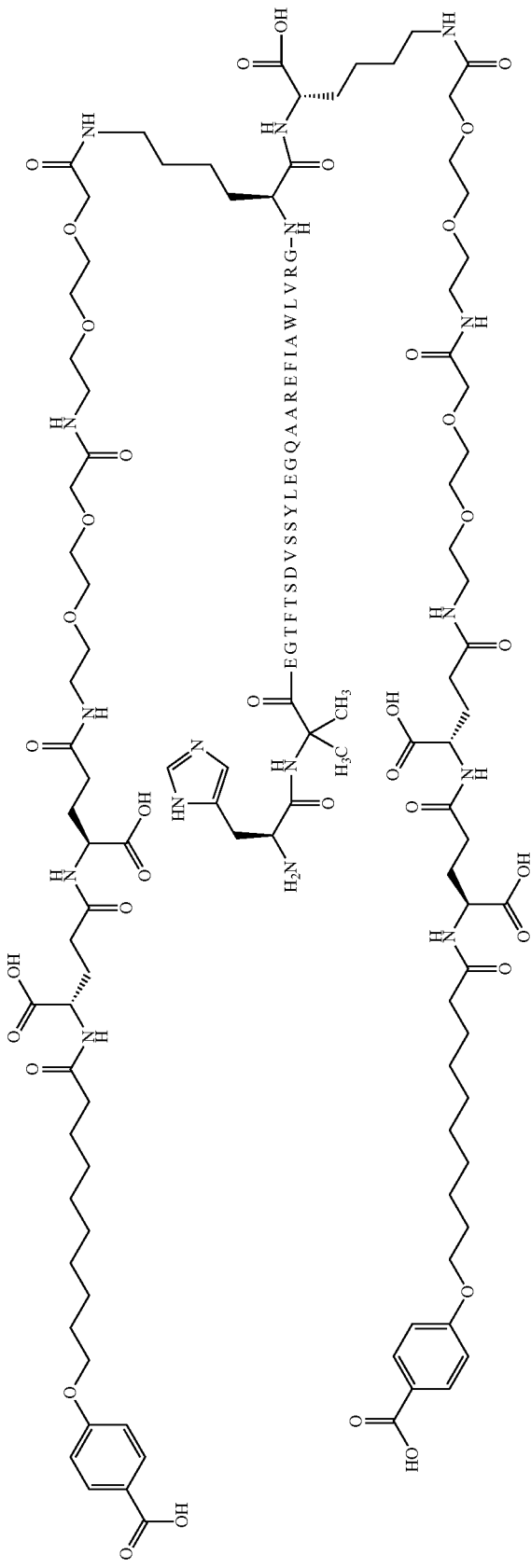

where the amino acid sequence is that of SEQ ID NO:3,
Chem. 30
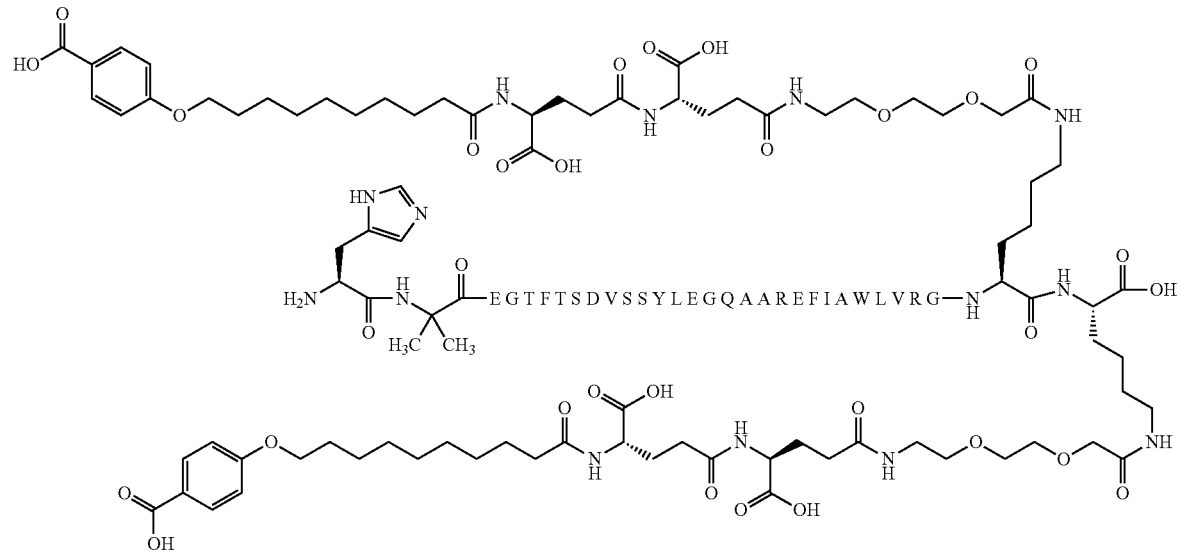
where the amino acid sequence is that of SEQ ID NO:3,
Chem. 31
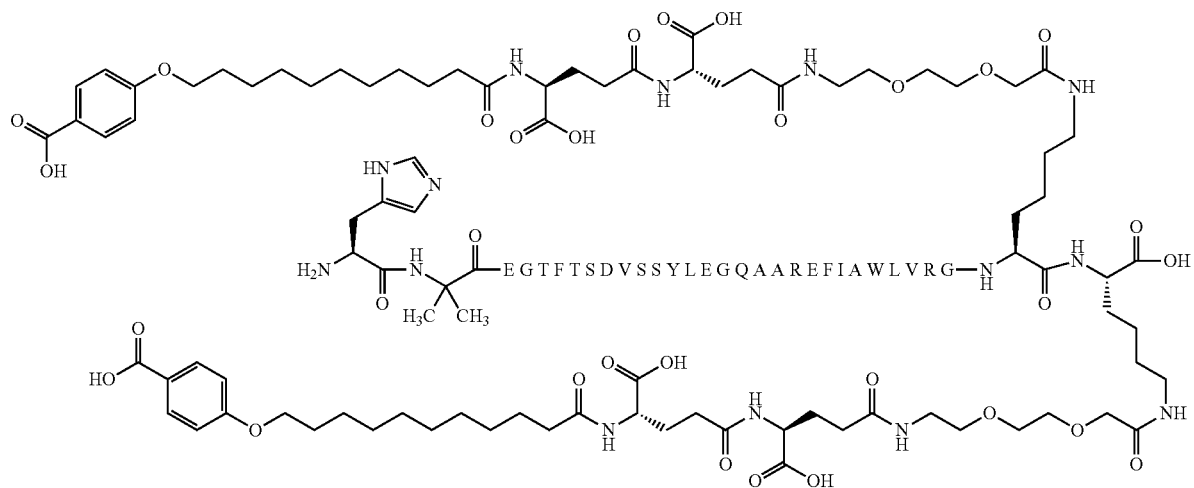

where the amino acid sequence is that of SEQ ID NO:3,
Chem. 32
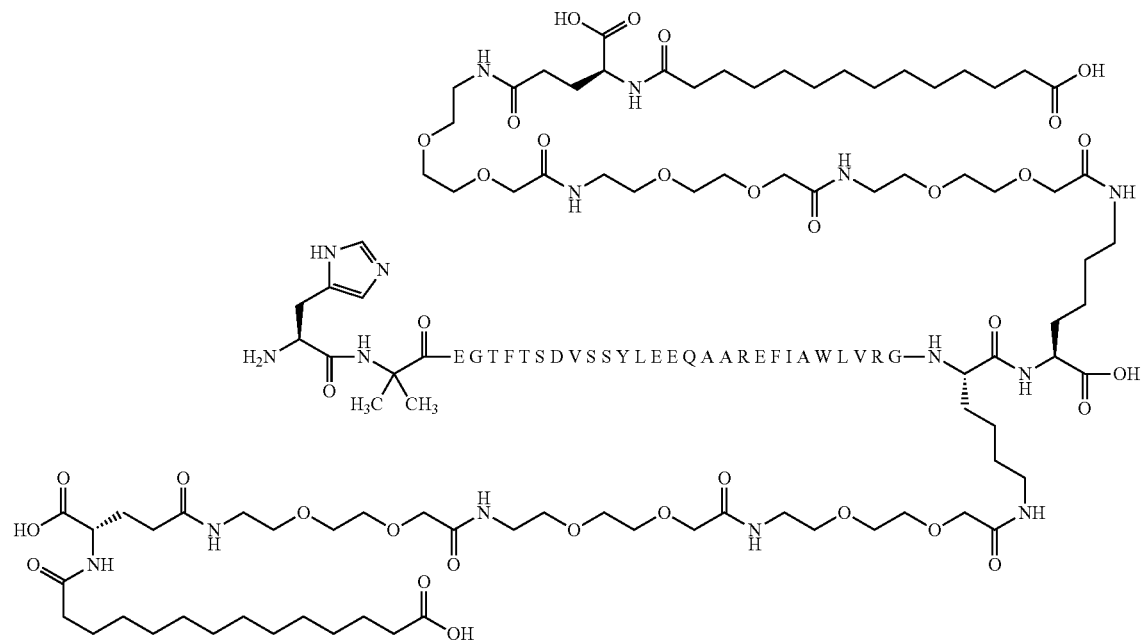
where the amino acid sequence is that of SEQ ID NO:2,
Chem. 33
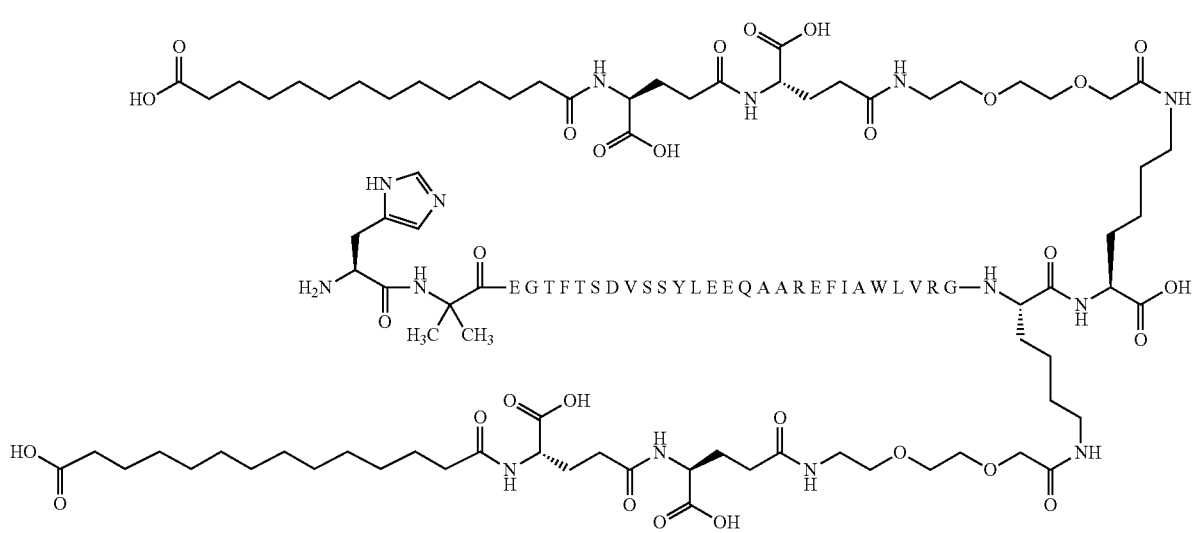
where the amino acid sequence is that of SEQ ID NO:2,
Chem. 34

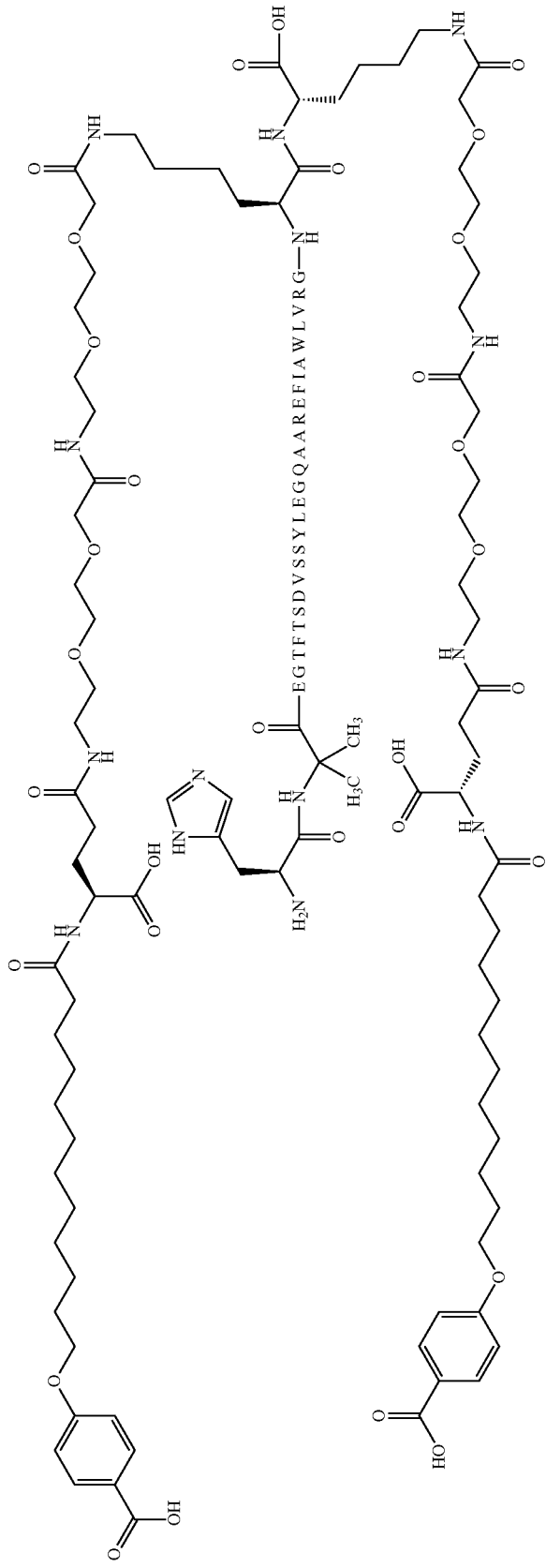

where the amino acid sequence is that of SEQ ID NO:3,
Chem. 35
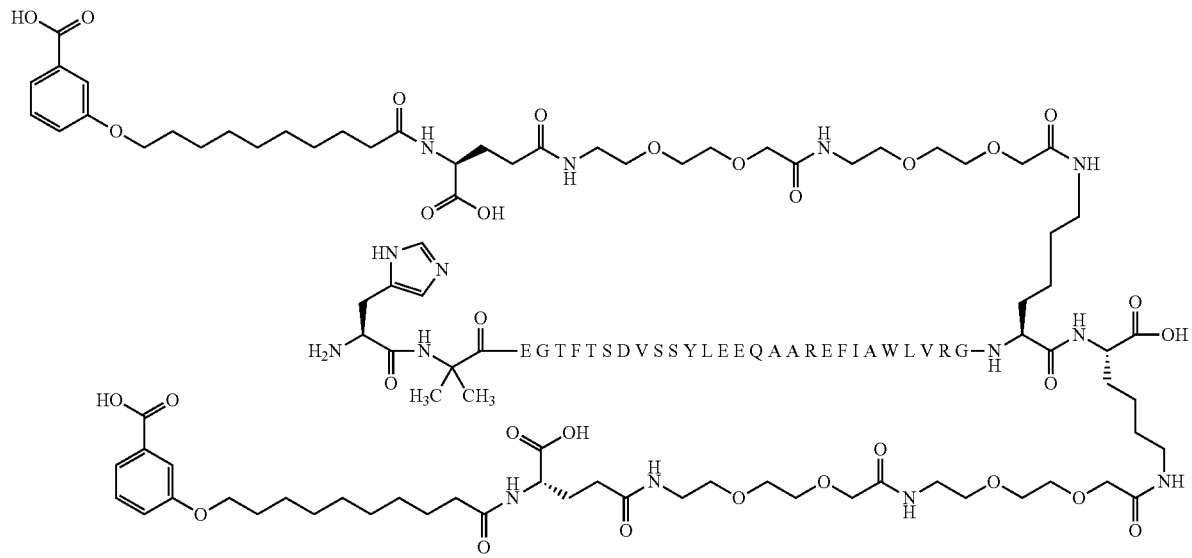
where the amino acid sequence is that of SEQ ID NO:2,
Chem. 36
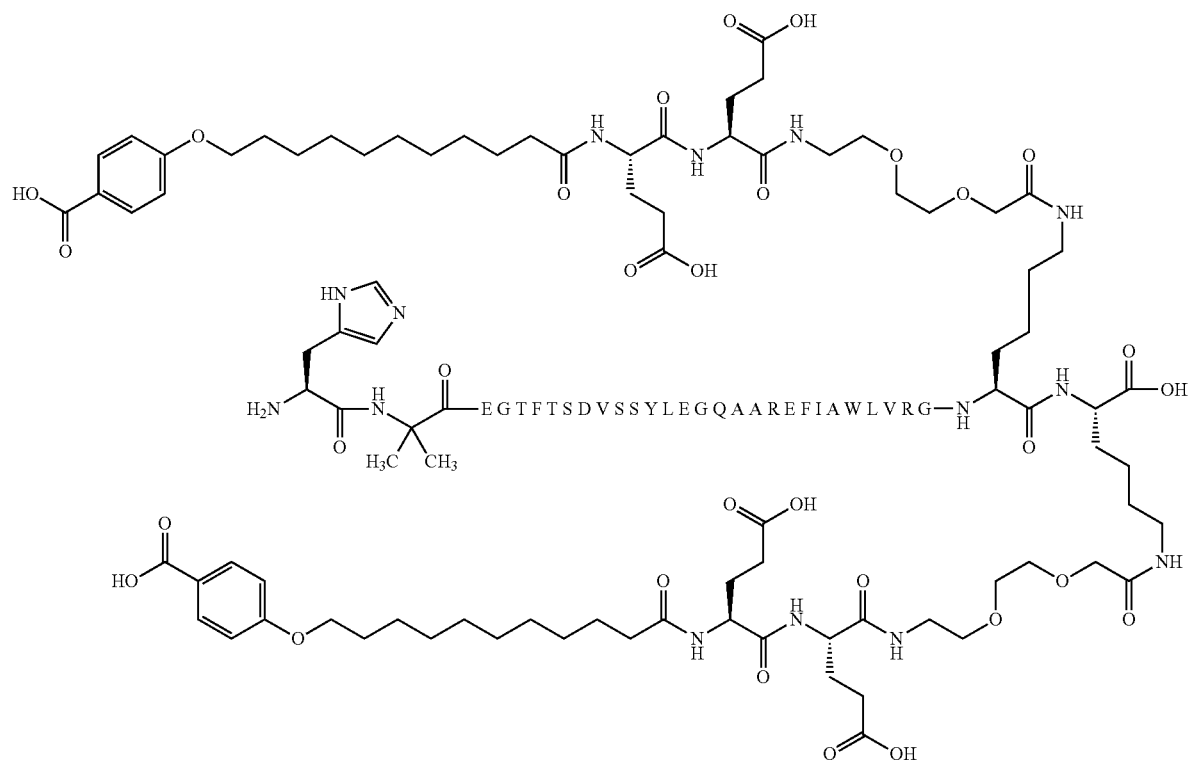
where the amino acid sequence is that of SEQ ID NO:3,
Chem. 37

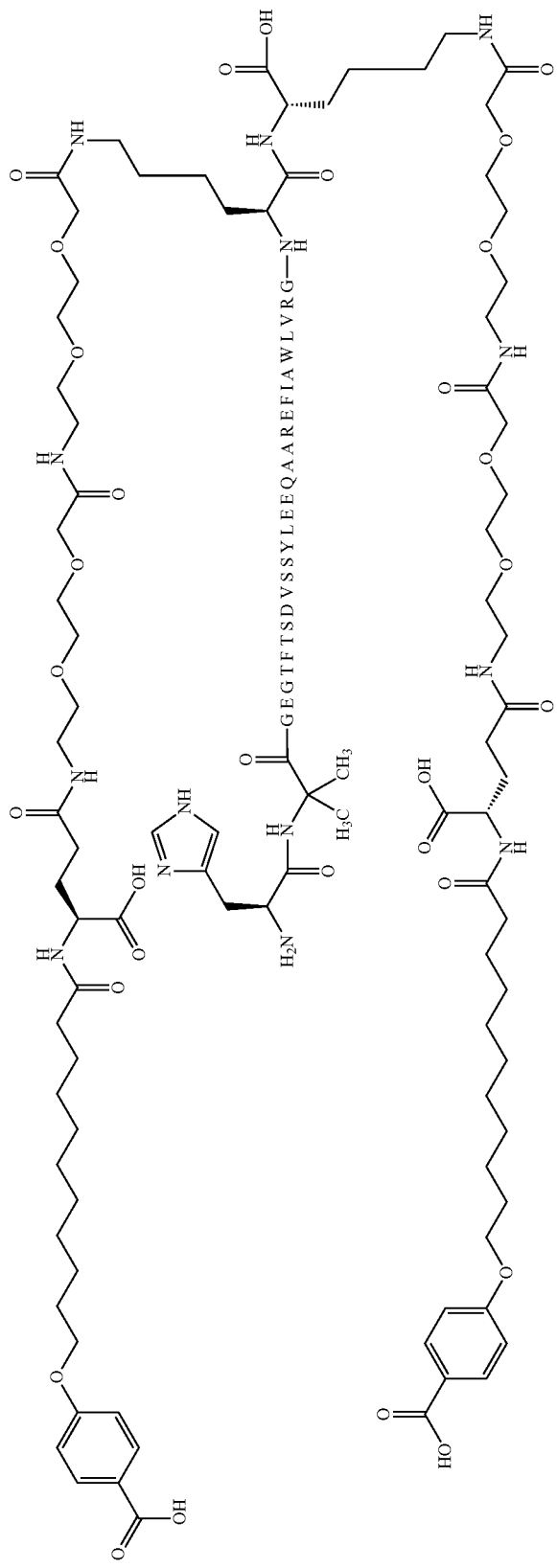

where the amino acid sequence is that of SEQ ID NO:5,
Chem. 38

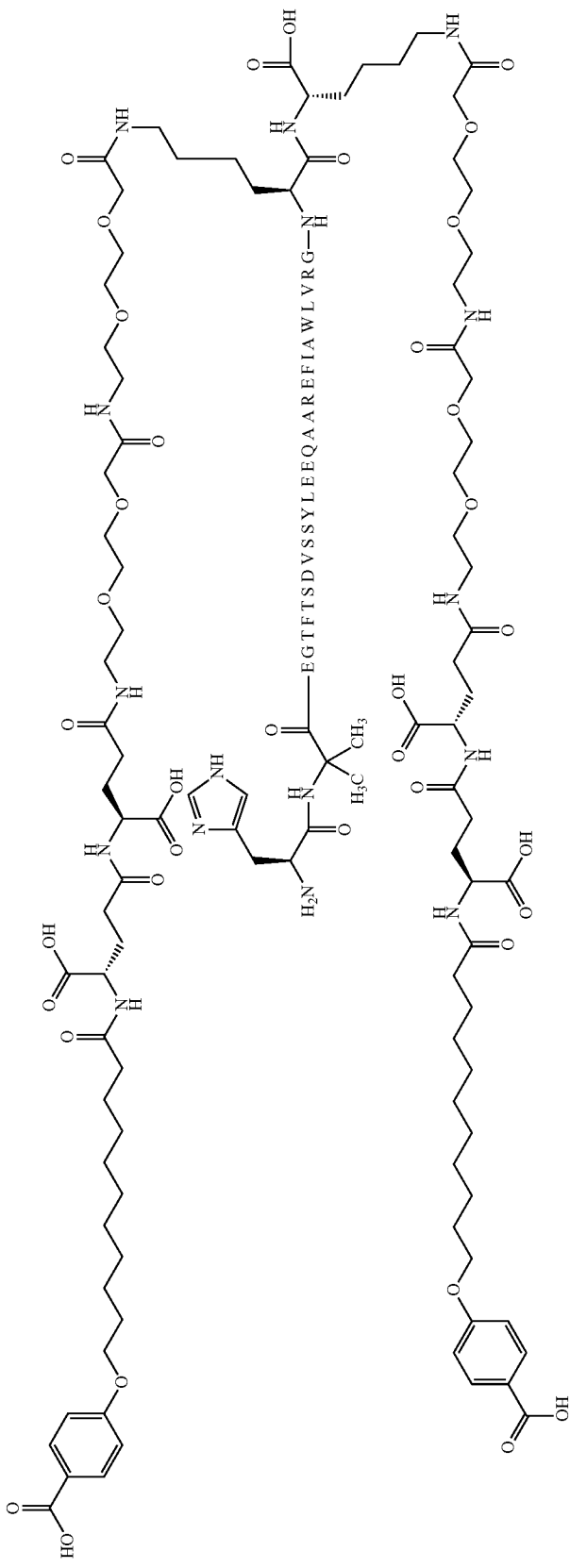

where the amino acid sequence is that of SEQ ID NO:2,
Chem. 39
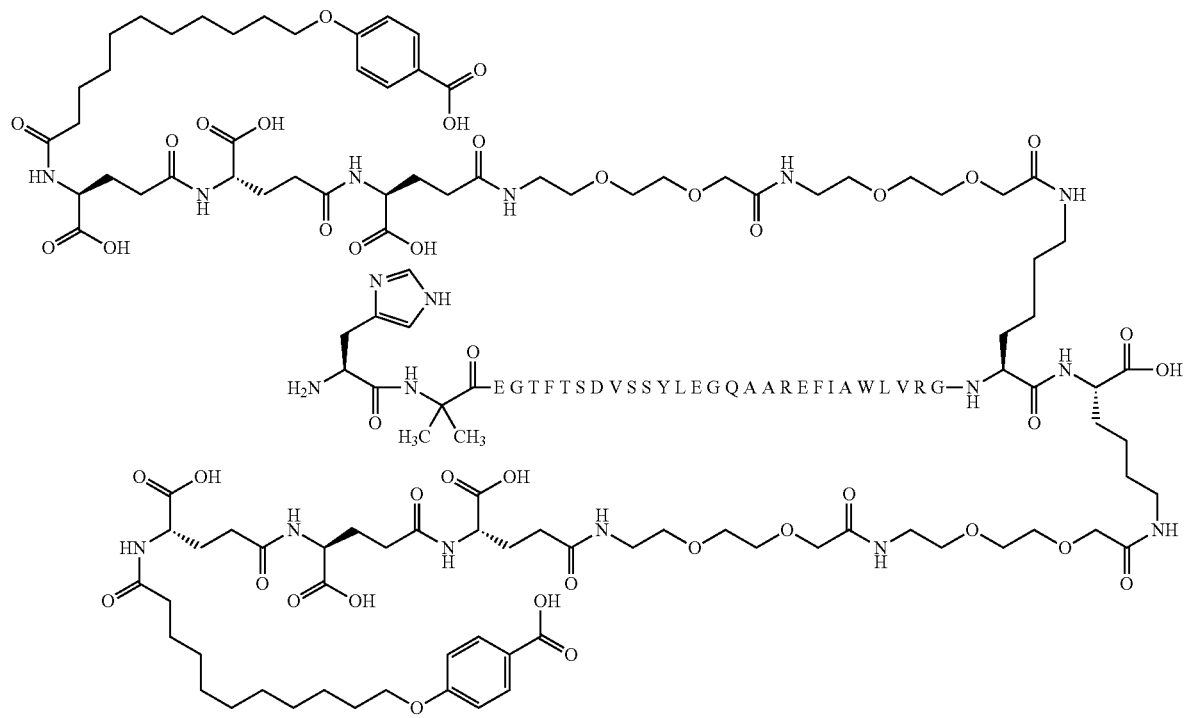
where the amino acid sequence is that of SEQ ID NO:3,
Chem. 40

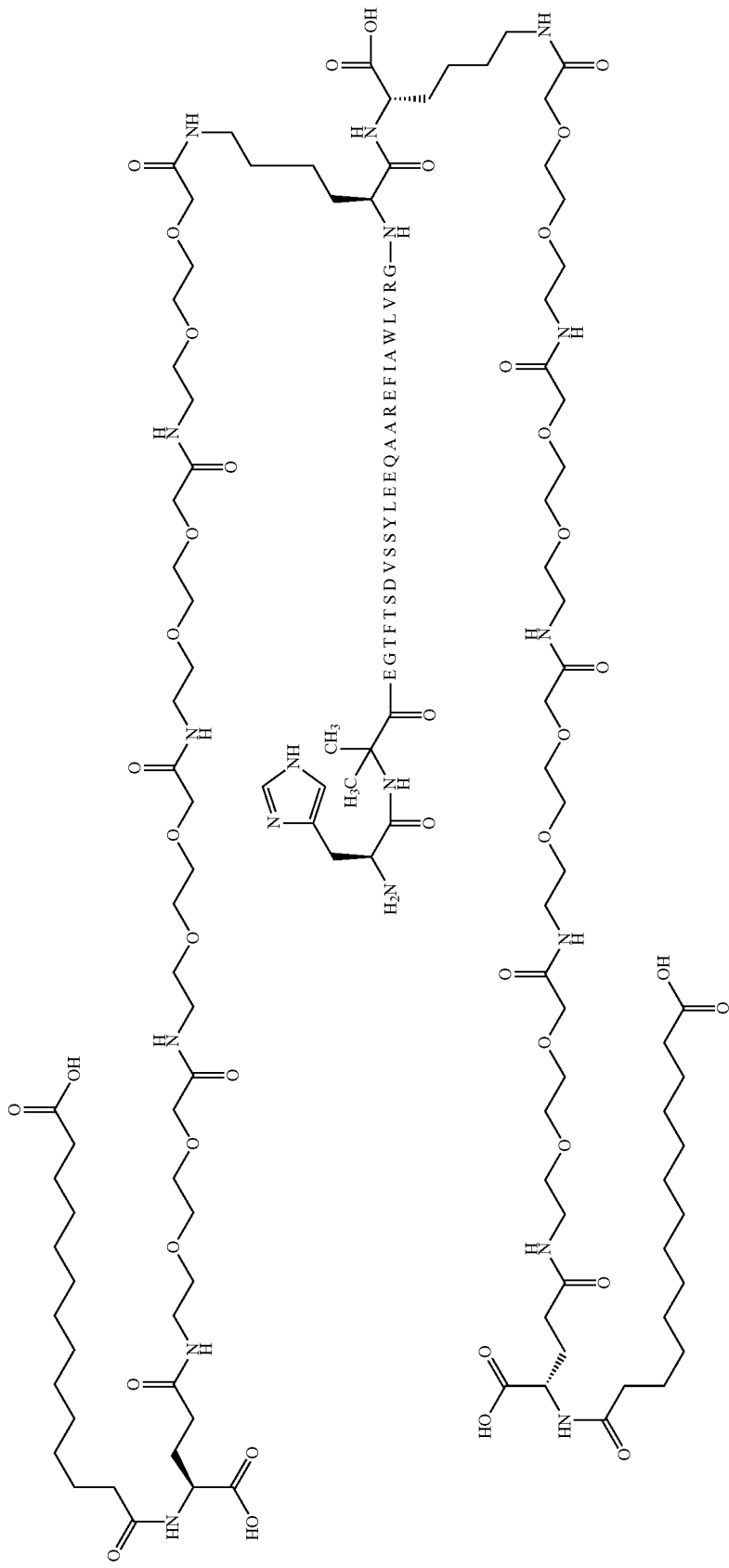

where the amino acid sequence is that of SEQ ID NO:2,
Chem. 41

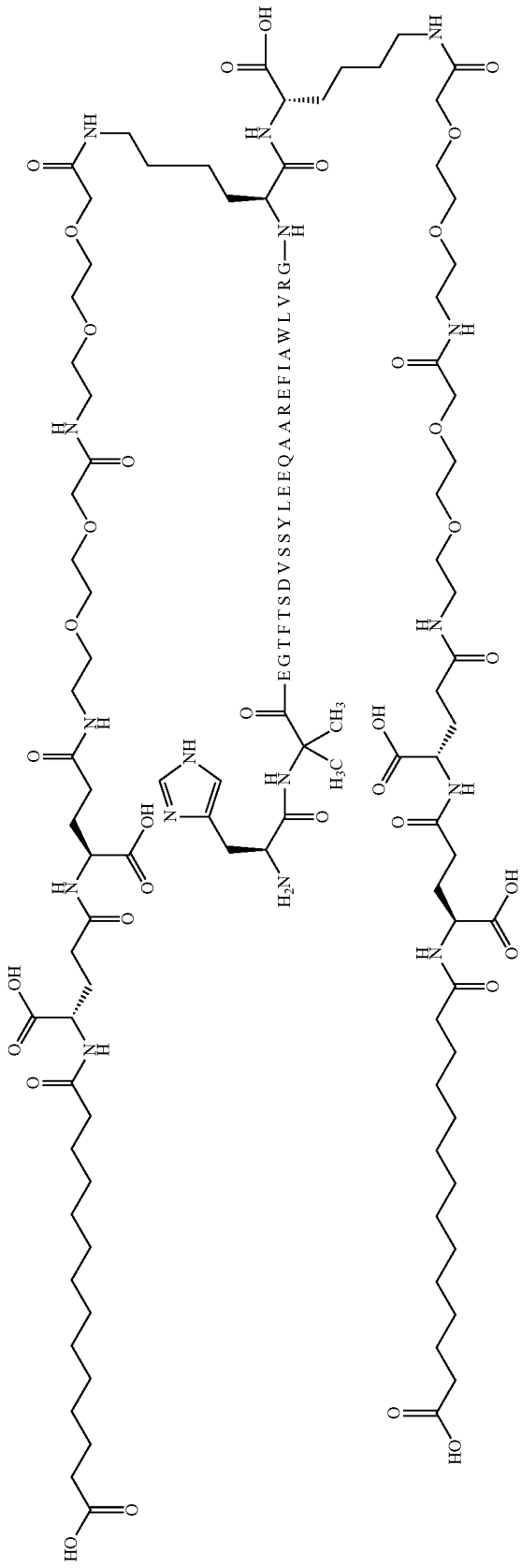

where the amino acid sequence is that of SEQ ID NO:2,
Chem. 42

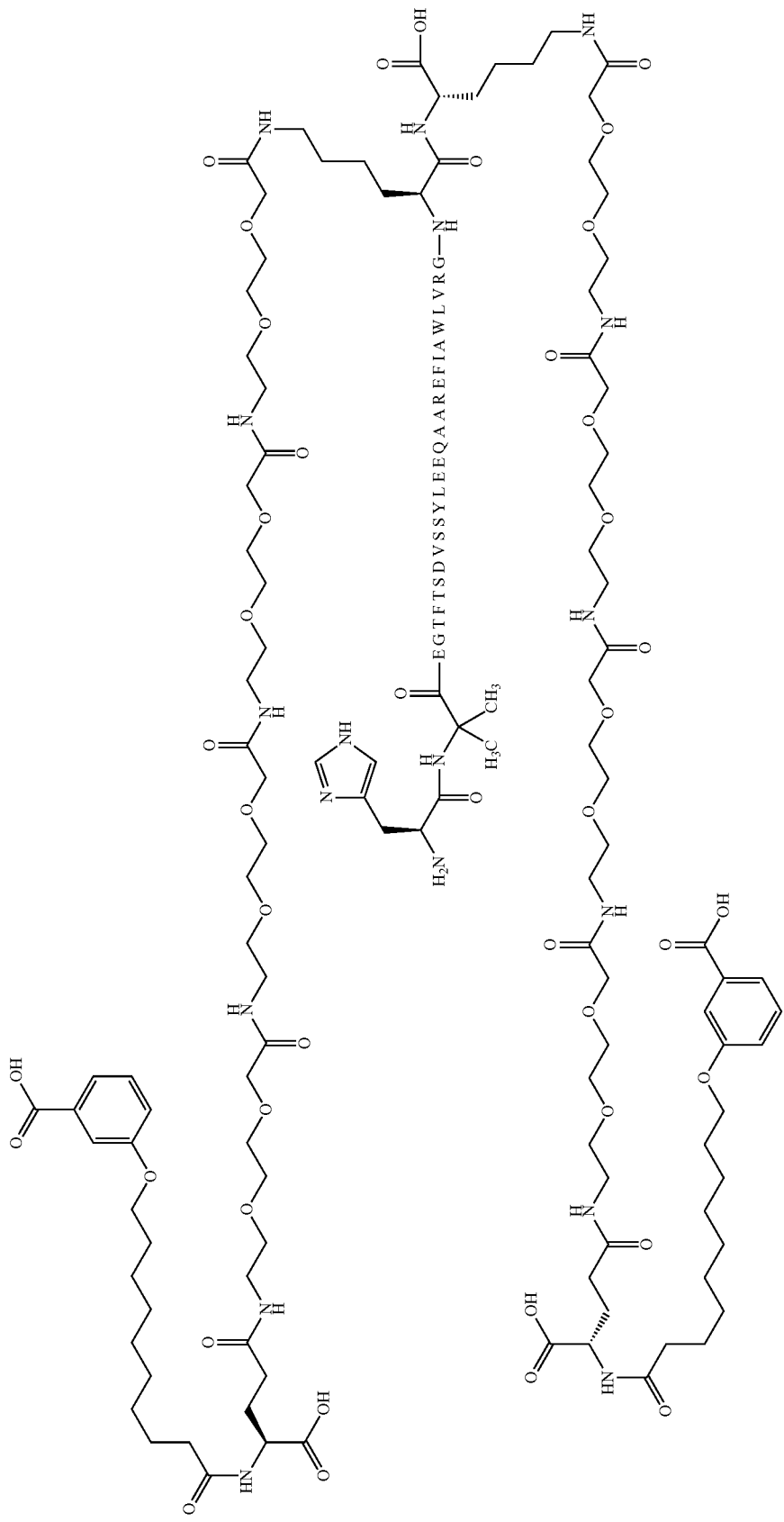

where the amino acid sequence is that of SEQ ID NO:2,
Chem. 43
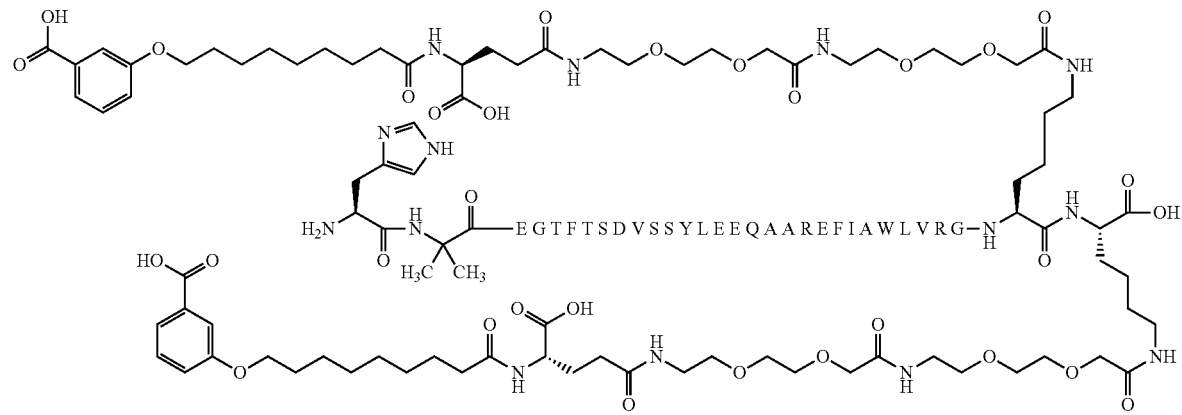
where the amino acid sequence is that of SEQ ID NO:2,
Chem. 44

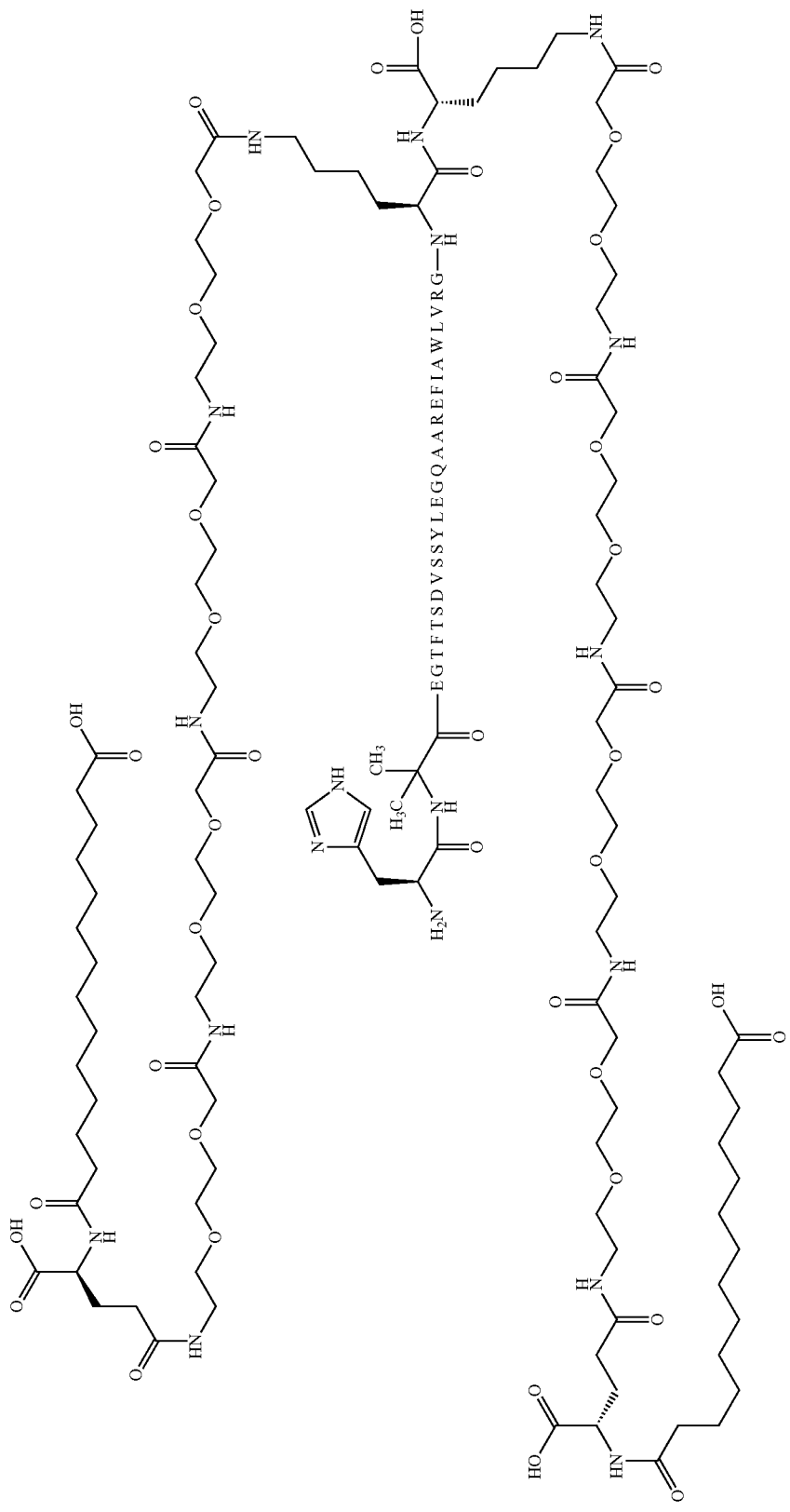

where the amino acid sequence is that of SEQ ID NO:3,
Chem. 45
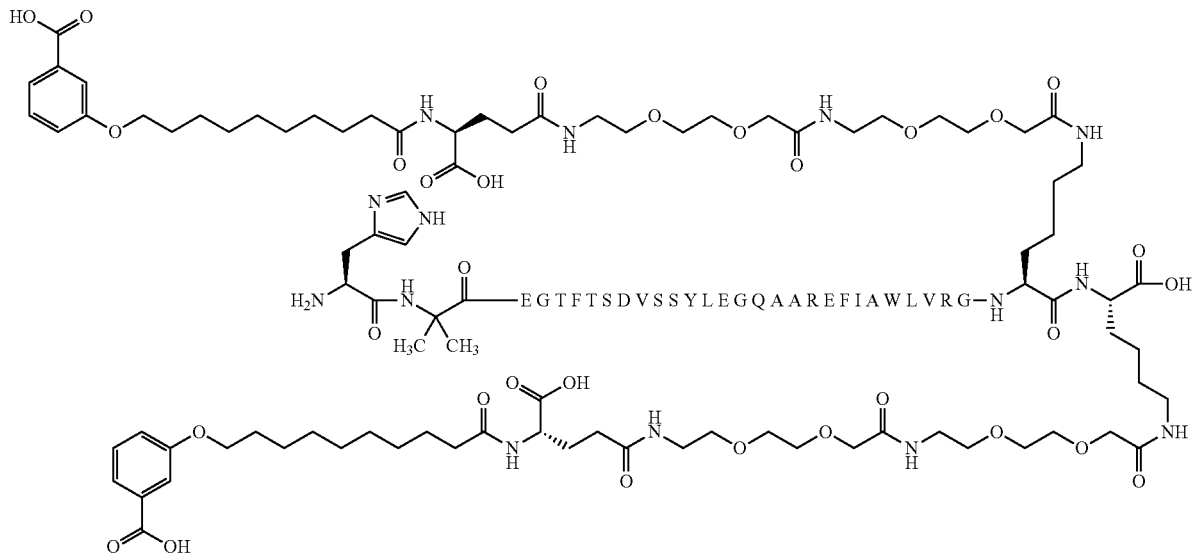
where the amino acid sequence is that of SEQ ID NO:3,
Chem. 46

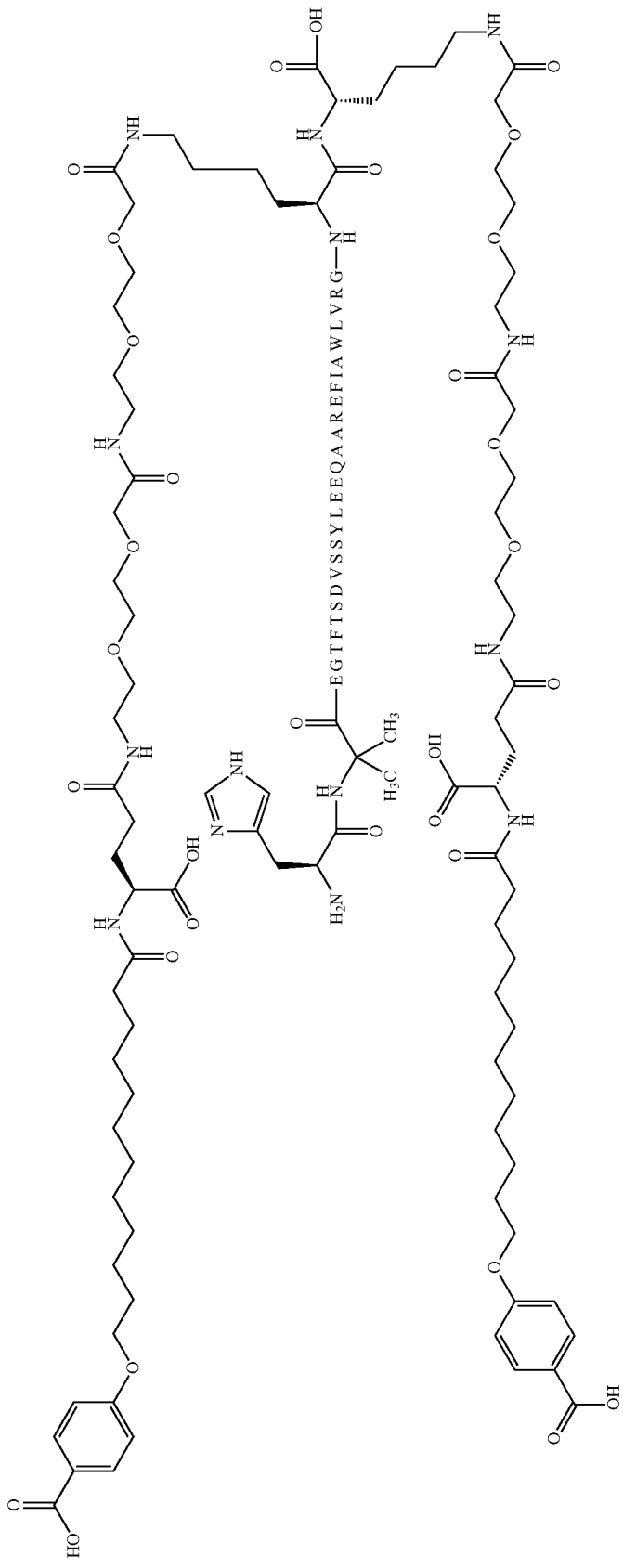

where the amino acid sequence is that of SEQ ID NO:2,
Chem. 47
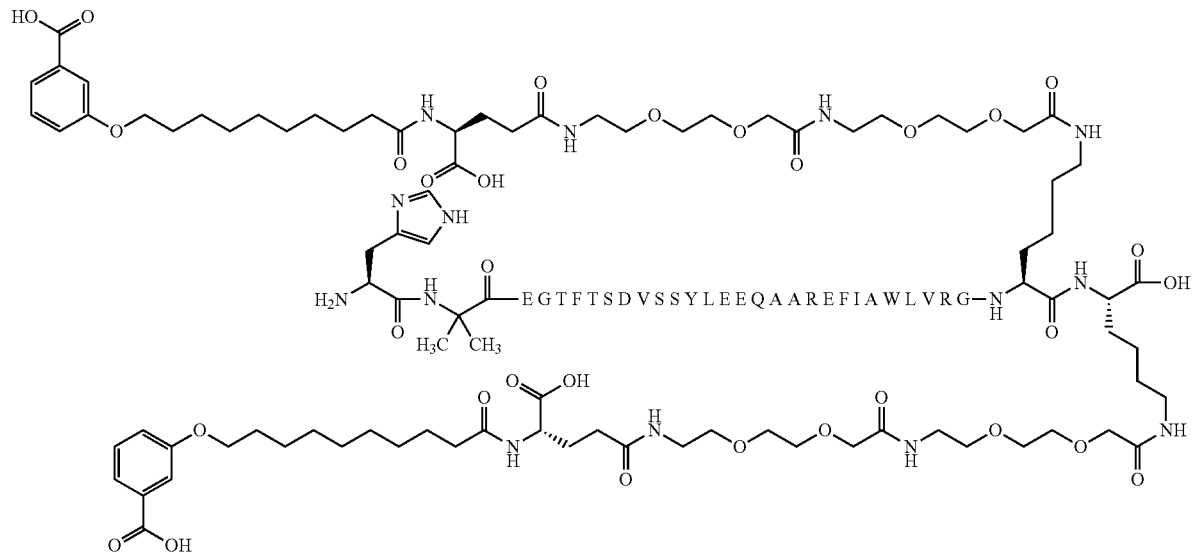
where the amino acid sequence is that of SEQ ID NO:6,
or
Chem. 48

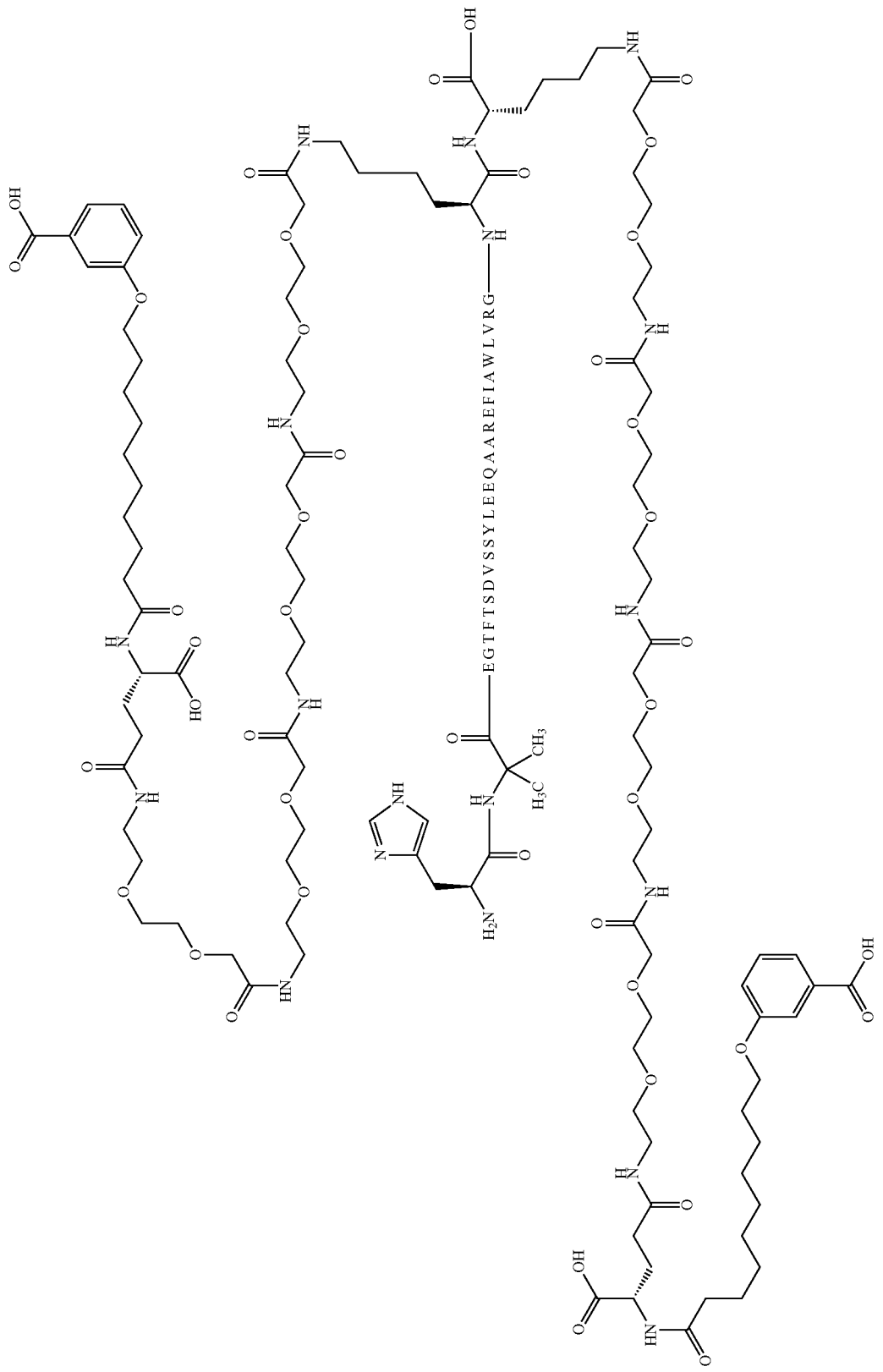

where the amino acid sequence is that of SEQ ID NO:6; or a pharmaceutically acceptable salt, amide, or ester thereof.

8. A peptide consisting of SEQ ID NO: 7 wherein amino acid position $Xaa_{25}$ is Trp.

9. A peptide consisting of SEQ ID NO: 7 wherein amino acid positions $Xaa_1$ and $Xaa_2$ are absent and amino acid position $Xaa_{25}$ is Trp.

10. A method for treating diabetes, eating disorders, cardiovascular diseases, gastrointestinal diseases, diabetic complications, critical illness, and/or polycystic ovary syndrome; and/or for improving lipid parameters, improving β-cell function, and/or for delaying diabetic disease progression—by administering a pharmaceutically active amount of a derivative according to claim 1.

11. A method for treating diabetes, eating disorders, cardiovascular diseases, gastrointestinal diseases, diabetic complications, critical illness, and/or polycystic ovary syndrome; and/or for improving lipid parameters, improving β-cell function, and/or for delaying diabetic disease progression—by administering a pharmaceutically active amount of a derivative according to claim 7.

* * * * *

UNITED STATES PATENT AND TRADEMARK OFFICE
CERTIFICATE OF CORRECTION

PATENT NO. : 10,689,429 B2
APPLICATION NO. : 15/301960
DATED : June 23, 2020
INVENTOR(S) : Lars Linderoth et al.

Page 1 of 1

It is certified that error appears in the above-identified patent and that said Letters Patent is hereby corrected as shown below:

In the Claims

At Column 147, Claim number 6, Line number 25, "$Xaa_{31}$ is Trp or His;" should read --$Xaa_{31}$ is Trp;--.

At Column 218, Claim number 7, Line number 15, "...EGTFTSDVSSYLEEQAAREFIAWLVRG..." should read --...EGTFTSDVSSYLEEQAAREFIEWLVRG...--.

Signed and Sealed this
First Day of December, 2020

Andrei Iancu
*Director of the United States Patent and Trademark Office*